United States Patent

[19]

Yamamoto et al.

[11] Patent Number: 5,962,438

[45] Date of Patent: Oct. 5, 1999

[54] ESTROGEN DERIVATIVE HAVING CARRIERS TO BONE

[75] Inventors: Michihiro Yamamoto, Nishinomiya; Akira Sasaki, Takarazuka; Takashi Katsumata, Sanda; Naomi Tsushima, Hirakata; Hideyuki Harada, Suita, all of Japan

[73] Assignee: Sumitomo Pharmaceuticals Company, Limited, Osaka, Japan

[21] Appl. No.: 08/945,124

[22] PCT Filed: Apr. 18, 1996

[86] PCT No.: PCT/JP96/01054

§ 371 Date: Oct. 17, 1997

§ 102(e) Date: Oct. 17, 1997

[87] PCT Pub. No.: WO96/33158

PCT Pub. Date: Oct. 24, 1996

[30] Foreign Application Priority Data

Apr. 21, 1995 [JP] Japan ................................ 7-120777

[51] Int. Cl.[6] ..................... A61K 31/675; A61K 31/665; A61K 31/66; C07F 9/6541
[52] U.S. Cl. ........................ 514/80; 514/100; 514/107; 548/113; 548/414; 549/220; 549/6; 558/158; 558/159; 562/12; 562/13
[58] Field of Search ............................. 514/80, 100, 107; 548/113, 414; 549/220; 558/158, 159; 562/12, 13

[56] References Cited

FOREIGN PATENT DOCUMENTS

| 0548884 | 6/1993 | European Pat. Off. . |
| 0561296 | 9/1993 | European Pat. Off. . |
| 4-352795 | 12/1992 | Japan ................. C07J 1/00 |
| 5-222073 | 8/1993 | Japan ................. C07F 9/38 |

OTHER PUBLICATIONS

Heiman, Daniel F. et al, Estrogen Receptor Based Imaging Agents. 1. Synthesis and Receptor Binding Affinity of Some Aromatic and D–Ring Halogenated Estrogens, Journal of Medicinal Chemistry, Sep. 1980, vol. 23, No. 9, pp. 994–1002.

Patent Abstracts of Japan, vol. 095, No. 002, Mar. 31, 1995.

*Primary Examiner*—Michael G. Ambrose
*Attorney, Agent, or Firm*—Sughrue, Mion, Zinn, Macpeak & Seas, PLLC

[57] ABSTRACT

A novel estrogen derivative represented by the formula:

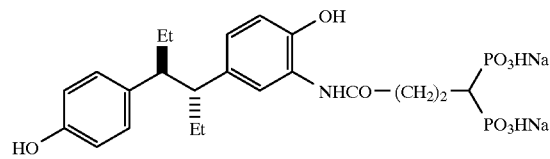

is useful for treating or preventing diseases caused by estrogen deficiency.

13 Claims, No Drawings

ESTROGEN DERIVATIVE HAVING CARRIERS TO BONE

This application is a 371 of PCT/JP96/01054 filed Apr. 18, 1996.

TECHNICAL FIELD

The present invention relates to novel estrogen derivatives having carriers to bone which are useful for treating or preventing diseases caused by estrogen deficiency, and pharmaceutically acceptable salts thereof.

BACKGROUND ART

Estrogens are steroid or non-steroid estrogenic hormones, and various substances including not only natural substances but also synthetic substances are known as estrogens (Environmental Health Perceptives, Vol. 61, pp. 97–110 (1985)). Natural human estrogen is 17β-estradiol produced mainly in ovary and this hormone plays an important role in the development of female secondary sexual character, the proliferation of endometrium, the control of sexual functions, the control of metabolism in bone, the control of lipid metabolism, etc. Therefore, when the estrogen in the body is deficient owing to aging or ovary malfunction, there are caused specific medical symptoms such as osteoporosis, menopausal disorders, lipid metabolism abnormality and vasomotor syndrome associated with menopause, atrophic vaginitis, kraurosis vulvae, premenstrual tension syndrome, female hypogonadism, etc. Estrogen supplementation therapy is applied to these diseases. The prophylactic effect of estrogen on fracture due to coronary cardiopathy or osteoporosis has recently been elucidated in postmenopausal women (Annals of Internal Medicine, Vol. 117, pp. 1038–1041 (1992)). Estrogen accelerates gonadotropin inhibition and is used also as a contraceptive in combination with progestogens (e.g. progesterone), other female sex hormones. However, since long-term administration of estrogen produces adverse side effects such as mastodynia, dysfunctional genital bleeding, corpulence, endometrial hyperplasia, endometrioma, mammary cancer, myocardial infarction, thromboembolism, cerebrovascular diseases, etc., a therapeutic agent having a more selective estrogen action is desired [American Journal of Medicine, Vol. 94, pp. 646–650 (1993)].

There have already been reported the following compounds obtained by combining each of various estrogens with a compound having a specific molecular structure which is considered to be rich in affinity for osseous tissue (a compound having affinity for bone) by a covalent bond through a spacer in order to incorporate the estrogen selectively into bone:

1) Compounds obtained by bonding a poly-(malonic acid) derivative as a compound having affinity for bone to the hydroxyl group of a 17β-estradiol derivative or the like by a carbamate linkage (Japanese Patent Unexamined Publication No. 2-36145).

2) Compounds obtained by bonding a bisphosphonic acid derivative as a compound having affinity for bone to the hydroxyl group of 17β-estradiol by an ester linkage or a carbamate linkage (Japanese Patent Application Kohyo No. 6-500777).

3) Compounds obtained by bonding a bisphosphonic acid derivative to the hydroxyl group of a steroid compound such as 17β-estradiol by a carbamate linkage, thiocarbamate linkage or carbonate linkage (Japanese Patent Unexamined Publication No. 4-352795).

4) Compounds obtained by bonding a bisphosphonic acid derivative to the hydroxyl group of a steroid compound such as 17β-estradiol by an ester linkage or a carbamate linkage (Japanese Patent Unexamined Publication No. 5-286993).

5) Specific compounds obtained by bonding a bisphosphonic acid derivative to the hydroxyl group of 17β-estradiol by an ester linkage (Japanese Patent Unexamined Publication No. 6-100576).

6) Compounds obtained by bonding a bisphosphonic acid derivative to the hydroxyl group of 17β-estradiol or the like by an ether linkage (Japanese Patent Unexamined Publication Nos. 5-230086 and 6-329697).

7) Compounds obtained by bonding a bisphosphonic acid derivative to the hydroxyl group of 17β-estradiol or the like by an ether linkage or a carbamate linkage (Japanese Patent Unexamined Publication No. 5-345791).

8) Compounds obtained by bonding a bisphosphonic acid derivative directly to the basic skeleton of an estrogen compound such as a hexestrol derivative or 2-phenylindole derivative through an alkylene group (Japanese Patent Unexamined Publication No. 5-222073).

Of the inventive compounds disclosed in these references, the compounds disclosed in 1) to 5) above are obtained by bonding a compound having affinity for bone to the hydroxyl group of an estrogen compound to form a so-called pro-drug type ester or carbamate, whose ester linkage or carbamate linkage is easily severed by metabolism in a living body. The estrogen compound released in the living body is expected to exhibit its effect in a local osseous tissue. The compounds disclosed in 6) and 7) above are obtained by bonding a compound having affinity for bone to the hydroxyl group of an estrogen compound to form an ether which is hardly decomposed by metabolism in a living body. Even if the whole ether molecule is transferred to an objective osseous tissue, it has a weakened effect as estrogen because at least one of the two important hydroxyl groups for exhibition of estrogen activity is blocked. Thus, it is considered that such compounds have inhibitory effect on bone resorption as so-called bisphosphonic acid derivatives. In addition, the compounds disclosed in 8) above are obtained by bonding a compound having affinity for bone directly to the basic skeleton of an estrogen compound through a spacer and hence retain the two important hydroxyl groups for exhibition of estrogen activity unlike the compounds disclosed in 1) to 7) above. However, the exhibition of estrogen action by such a bonding method has been not yet sufficient.

As compounds having affinity for bone, bisacylphosphonic acid derivatives [Pharmaceutical Research, Vol. 9, 143–148 (1992)], iminobismethylenebisphosphonic acid derivatives [Japanese Patent Unexamined Publication No. 6-298779] and tartronic acid derivatives [WO9409770 and WO9410127] are known as background art in addition to the above-mentioned poly(malonic acid) derivatives and bisphosphonic acid derivatives. However, no compound obtained by bonding any of such derivatives to estrogen is described in these references.

The present invention is intended to provide a therapeutic agent and a prophylactic agent, which contains as an active ingredient a novel estrogen derivative having a higher selectivity for osseous tissue than for other organs such as genital organs, etc. is highly effective against diseases due to estrogen deficiency by virtue of the enhancement or prolongation of the effect of the derivative by its accumulation in osseous tissue, and has less adverse side effect.

DISCLOSURE OF THE INVENTION

In order to solve the above problems, the present inventors conducted further earnest researches on a method for bonding an estrogen compound to a compound having affinity for bone, and consequently found that surprisingly, compounds obtained by introducing an amino group into the aromatic ring as basic skeleton of an estrogen compound and bonding the amino group to a compound having affinity for bone by —NH—CO— (amide) or —NH—SO$_2$— (sulfonamide) through any of various spacers are estrogen derivatives with affinity for bone which have a high selectivity for osseous tissue. Thus, the present invention has been accomplished.

That is, the present invention relates to compounds represented by the general formula (I):

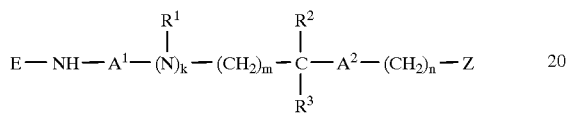

(I)

wherein A$^1$ is —CO— or —SO$_2$—; A$^2$ is a single bond, —S—, —O—, a group of the formula —NR$^4$— wherein R$^4$ is a hydrogen atom or an alkyl group of 1 to 6 carbon atoms, or a group of the formula —CO—NR$^4$— wherein R$^4$ is as defined above; R$^1$ is a hydrogen atom or an alkyl group of 1 to 6 carbon atoms; R$^2$ and R$^3$, which may be the same or different, are independently a hydrogen atom, an alkyl group of 1 to 6 carbon atoms, an alkenyl group of 3 to 6 carbon atoms, a cycloalkyl group of 3 to 7 carbon atoms, an aralkyl group, a substituted aralkyl group, a phenyl group or a substituted phenyl group, or R$^2$ and R$^3$, when taken together with the carbon atom to which they are bonded, form a saturated or unsaturated 3- to 7-membered alicyclic hydrocarbon group; k is 0 or 1 in the case of A$^1$ being —CO—, and k is 0 in the case of A$^2$ being —SO$_2$—; m and n are independently an integer of 0 to 5;

Z is a group represented by any of the following general formulas (IIa) to (IId):

(IIa)

wherein R$^5$ is a hydrogen atom, a halogen atom, a methyl group, a hydroxyl group or a protected hydroxyl group, and R$^6$, R$^7$, R$^8$ and R$^9$ are independently a hydrogen atom, an alkyl group of 1 to 6 carbon atoms, a haloalkyl group of 2 to 6 carbon atoms, an allyl group, a benzyl group or a group of the formula —CH$_2$—O—CO—R$^{10}$ wherein R$^{10}$ is an alkyl group of 1 to 6 carbon atoms,

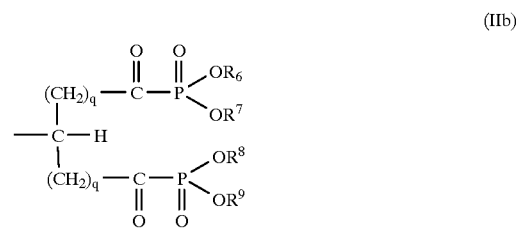

(IIb)

wherein R$^6$, R$^7$, R$^8$ and R$^9$ are as defined above, and q is 0 or 1,

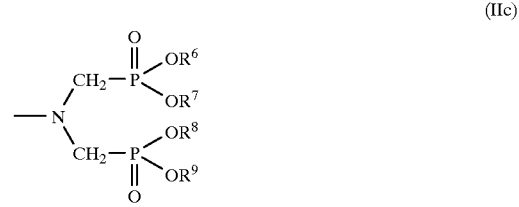

(IIc)

wherein R$^6$, R$^7$, R$^8$ and R$^9$ are as defined above, and

(IId)

wherein R$^6$ is as defined above, and R$^{11}$ is a hydroxyl group or a protected hydroxyl group;

and E is a group of the general formula (III):

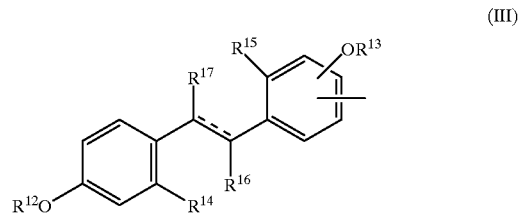

(III)

wherein R$^{12}$ and R$^{13}$, which may be the same or different, are independently a hydrogen atom, a hydroxyl-protecting group, a group of the formula —CO—NR$^{18}$R$^{19}$ wherein R$^{18}$ and R$^{19}$, which may be the same or different, are independently a hydrogen atom, an alkyl group of 1 to 10 carbon atoms, a hydroxyalkyl group of 2 to 6 carbon atoms, a haloalkyl group of 2 to 6 carbon atoms, a phenyl-substituted or unsubstituted carboxyalkyl group of 2 to 6 carbon atoms, a cycloalkyl group of 3 to 7 carbon atoms, an aralkyl group, a substituted aralkyl group, a phenyl group or a substituted phenyl group; a group of the formula —CO—R$^{20}$ wherein R$^{20}$ is an alkyl group of 1 to 19 carbon atoms, an alkenyl group of 3 to 19 carbon atoms, a cycloalkyl group of 3 to 7 carbon atoms, an alkyl group of 1 to 6 carbon atoms substituted by a cycloalkyl group of 3 to 7 carbon atoms, an aralkyl group, a substituted aralkyl group, a phenyl group, a substituted phenyl group, or a 5- or 6-membered heterocyclic group; or a group of the general formula (IV):

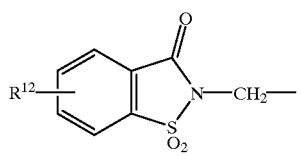
(IV)

wherein $R^{21}$ is a hydrogen atom, a halogen atom, an alkyl group of 1 to 6 carbon atoms, or an alkoxy group of 1 to 6 carbon atoms; $R^{14}$ and $R^{15}$, which may be the same or different, are independently a hydrogen atom, a halogen atom, a methyl group, a hydroxyl group or a protected hydroxyl group; $R^{16}$ is an alkyl group of 1 to 6 carbon atoms, a hydroxyalkyl group of 2 to 6 carbon atoms, a haloalkyl group of 2 to 6 carbon atoms, a phenyl group, or a phenyl group substituted by a hydroxyl group or a protected hydroxyl group; $R^{17}$ is an alkyl group of 1 to 6 carbon atoms, a hydroxyalkyl group of 2 to 6 carbon atoms, or a haloalkyl group of 2 to 6 carbon atoms; $R^{14}$ and $R^{16}$, when taken together, may form —O—, —CH$_2$— or —CH$_2$CH$_2$—, and $R^{15}$ and $R^{17}$, when taken together as —$R^{17}$—$R^{15}$—, may form —O—, —S—. —COO—, —OCO—, a group of the formula —NR$^{22}$— wherein $R^{22}$ is an alkyl group of 1 to 6 carbon atoms, a hydroxyalkyl group of 2 to 6 carbon atoms, or a haloalkyl group of 2 to 6 carbon atoms; a group of the formula —CHR$^{22}$—A$^3$— or a group of the formula —A$^3$—CHR$^{22}$— wherein $R^{22}$ is as defined above, and $A^3$ is a single bond, —O— or —CH$_2$—; and the combination of the broken line and solid line between the carbon atoms to which $R^{16}$ and $R^{17}$, respectively, are bonded represents a single bond or a double bond, or pharmaceutically acceptable salts thereof.

The present invention also relates to pharmaceutical compositions containing the above-mentioned compound or a pharmaceutically acceptable salt thereof.

The present invention further relates to pharmaceutical compositions for the treatment or prophylaxis of osteoporosis, menopausal disorders, lipid metabolism abnormality and vasomotor syndrome associated with menopause, atrophic vaginitis, kraurosis vulvae, premenstrual tension syndrome, female hypogonadism, or coronary cardiopathy in postmenopausal women or for contraception, which contains the above-mentioned compound or a pharmaceutically acceptable salt thereof as an active ingredient.

The present invention still further relates to the above-mentioned compounds or pharmaceutically acceptable salts thereof for use as an active ingredient of a pharmaceutical composition.

The present invention still further relates to use of the above-mentioned compounds or pharmaceutically acceptable salts thereof for the preparation of a pharmaceutical composition for the treatment or prophylaxis of osteoporosis, menopausal disorders, lipid metabolism abnormality and vasomotor syndrome associated with menopause, atrophic vaginitis, kraurosis vulvae, premenstrual tension syndrome, female hypogonadism, or coronary cardiopathy in postmenopausal women or for contraception.

The present invention still further relates to a method for treating or preventing osteoporosis, menopausal disorders, lipid metabolism abnormality and vasomotor syndrome associated with menopause, atrophic vaginitis, kraurosis vulvae, premenstrual tension syndrome, female hypogonadism, or coronary cardiopathy in postmenopausal women or for contraception, which comprises administering an effective amount of the above-mentioned compound or a pharmaceutically acceptable salt thereof to a human being.

BEST MODE FOR CARRYING OUT THE INVENTION

The details of the present invention are explained below.

In the above general formula (I), Z is, for example, a residue formed from a compound with affinity for bone of the formula $CH_3$—Z by removing the methyl group. Preferable specific examples of the compound with affinity for bone are ethane-1,1-bisphosphonic acid, 1-hydroxyethane-1,1-bisphosphonic acid, 2-methylmalonylbisphosphonic acid, 3-methylglutarylbisphosphonic acid, methyliminobis-methylenebisphosphonic acid, 2-methyltartronic acid, and derivatives thereof obtained by protecting the acid moieties. Especially preferable examples of the compound with affinity for bone are bisphosphonic acid derivatives in which Z is a group of the above general formula (IIa), $R^5$ is a hydrogen atom or a hydroxyl group, and $R^6$, $R^7$, $R^8$ and $R^9$ are independently a hydrogen atom, a propionyloxymethyl group, an isobutyryloxymethyl group or a pivaloyloxymethyl group.

E is the aromatic cyclic group of a compound having activity as estrogen and is preferably a group of the general formula (IIIa):

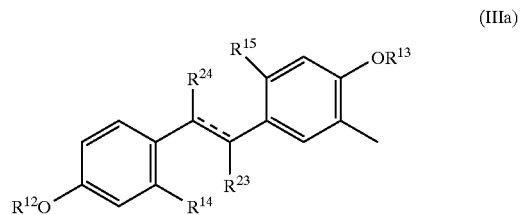
(IIIa)

wherein $R^{12}$, $R^{13}$, $R^{14}$ and $R^{15}$ are as defined above, $R^{23}$ and $R^{24}$, which may be the same or different, are independently an alkyl group of 1 to 6 carbon atoms, a hydroxyalkyl group of 2 to 6 carbon atoms, or a haloalkyl group of 2 to 6 carbon atoms, and the combination of the broken line and solid line between the carbon atoms to which $R^{23}$ and $R^{24}$, respectively, are bonded represents a single bond or a double bond, or a group of the general formula (IIIc):

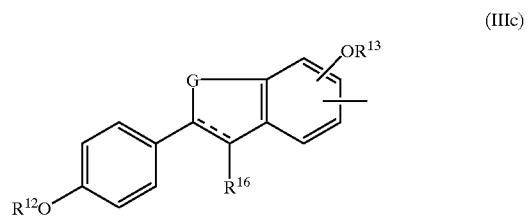
(IIIc)

wherein $R^{12}$, $R^{13}$ and $R^{16}$ are as defined above, G is —O—, —S—, —COO—, a group of the formula —NR$^{22}$— wherein $R^{22}$ is as defined above, or a group of the formula CHR$^{22}$—A$^3$— wherein $R^{22}$ and $A^3$ are as defined above, and the combination of the broken line and solid line between the carbon atom to which $R^{16}$ is bonded and the carbon atom adjacent thereto represents a single bond or a double bond.

E is especially preferably a group represented by the general formula (IIIb):

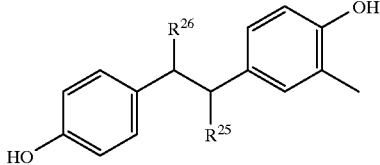

(IIIb)

wherein $R^{25}$ and $R^{26}$, which may be the same or different, are independently an alkyl group of 1 to 6 carbon atoms, or the general formula (IIId):

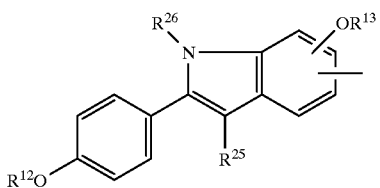

(IIId)

wherein $R^{12}$, $R^{13}$, $R^{25}$ and $R^{26}$ are as defined above.

Preferable specific examples of the estrogen compound are hexestrol, erythro 1-fluoro-3,4-bis(4-hydroxyphenyl) hexane, meso 2,3-bis(2,4-dihydroxyphenyl)hexane, meso 2,3-bis(4-hydroxy-2-methylphenyl)butane, diethylstilbestrol, 3,4-dihydro-6-hydroxy-2-(4-hydroxyphenyl)-1-phenylnaphthalene, 3-ethyl-6-hydroxy-2-(4-hydroxyphenyl)-1-methylindene (indenestrol), 1-ethyl-6-hydroxy-2-(4-hydroxyphenyl)-3-methylindole, 1,3-diethyl-6-hydroxy-2-(4-hydroxyphenyl)indole, 1,3-diethyl-5-hydroxy-2-(4-hydroxyphenyl)indole, 3-ethyl-5-hydroxy-2-(4-hydroxyphenyl)benzo[b]thiophene, 4-ethyl-3-(4-hydroxyphenyl)-2-methyl-2H-1-benzopyran-7-ol, 3-(4-hydroxyphenyl)-4-phenyl-2H-1-benzopyran-7-ol, 4-n-propyl-7-hydroxy-3-(4-hydroxyphenyl)-2H-1-benzopyran-2-one, cumestrol, and derivatives thereof obtained by protecting the hydroxyl group.

The estrogen derivative having affinity for bone of the present invention is characterized in that an amino group introduced into the aromatic ring of the above-mentioned estrogen compound is bonded to the compound having affinity for bone through a suitable spacer to form an amide or a sulfonamide.

In the general formula (I), $A^1$ is preferably —CO—. In the spacer portion, $A^2$ is preferably a single bond or a group of the formula —$NR^4$—, k is preferably 0 or 1, m is preferably an integer of 0 to 2, n is preferably an integer of 0 to 3, and $R^1$, $R^2$ and $R^3$ are preferably independently a hydrogen atom.

Especially preferable examples of the compound of the present invention are erythro 3-(3-(4,4-diphosphonobutyrylamino)-4-hydroxyphenyl)-4-(4-hydroxyphenyl)hexane

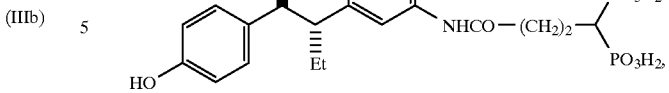

its pharmaceutically acceptable salts, erythro 3-(3-(5,5-diphosphonovalerylamino)-4-hydroxyphenyl)-4-(4-hydroxyphenyl)hexane

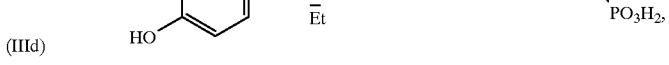

its pharmaceutically acceptable salts, erythro 3-(3-((diphosphonomethylamino)acetylamino)-4-hydroxyphenyl)-4-(4-hydroxyphenyl)hexane

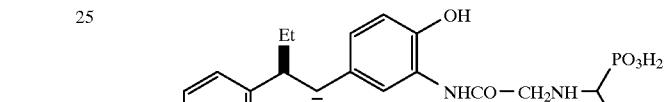

and its pharmaceutically acceptable salts.

In the present invention, the alkyl group of 1 to 6 carbon atoms includes linear or branched alkyl groups. Specific examples thereof are methyl, ethyl, n-propyl, 1-methylethyl, n-butyl, t-butyl, 1-methylpropyl, 2-methylpropyl, pentyl, 1,1-dimethylpropyl, 2,2-dimethylpropyl, 1-methylbutyl, 3-methylbutyl, hexyl, 2-methylpentyl, etc.

The alkenyl group of 3 to 6 carbon atoms include linear or branched alkenyl groups. Specific examples thereof are allyl, 2-butenyl, 3-butenyl, 2-methyl-2-propenyl, 2-pentenyl, 4-pentenyl, 3-methyl-2-butenyl, 2-hexenyl, etc.

Specific examples of the cycloalkyl group of 3 to 7 carbon atoms are cyclopropyl, cyclobutyl, cyclopentyl, cyclohexyl, cycloheptyl, etc.

The aralkyl group includes, for example, linear or branched alkyl groups of 1 to 4 carbon atoms substituted by an aryl group of 10 or less carbon atoms, such as phenyl group. Specific examples thereof are benzyl group, phenethyl group, phenylpropyl group, etc.

Specific examples of the halogen atom are fluorine atom, chlorine atom, bromine atom and iodine atom.

The alkoxy group of 1 to 6 carbon atoms includes linear or branched alkoxy groups. Specific examples thereof are methoxy, ethoxy, n-propoxy, iso-propoxy, n-butoxy, t-butoxy, 2-methylpropoxy, pentyloxy, hexyloxy, etc.

The substituted aralkyl group and the substituted phenyl group include substituted derivatives of the above-exemplified aralkyl groups and phenyl group, respectively, which have one or two substituents selected from the group consisting of halogen atoms (specific examples thereof are the same as those given above), alkyl groups of 1 to 6 carbon atoms (specific examples thereof are the same as those given above), alkoxy groups of 1 to 6 carbon atoms (specific examples thereof are the same as those given above), amino group, hydroxyl group and protected hydroxyl groups. Specific examples of the substituted aralkyl group and the substituted phenyl group are 4-chlorobenzyl, 2-fluorobenzyl, 4-fluorobenzyl, 2-methylbenzyl, 3-methoxybenzyl, 4-methoxybenzyl, 4-ethoxybenzyl, 3,4-dimethoxybenzyl, 2-hydroxybenzyl, 3-hydroxybenzyl, 4-hydroxybenzyl, 3,4-dihydroxybenzyl, 2-acetoxybenzyl, 4-methoxymethoxybenzyl, 3-triethylsilyloxybenzyl, 4-chlorophenyl, 2-fluorophenyl, 4-fluorophenyl, 4-bromophenyl, 2-methylphenyl, 4-methylphenyl, 3-methoxyphenyl, 4-methoxyphenyl, 4-ethoxyphenyl, 2-hydroxyphenyl, 3-hydroxyphenyl, 4-hydroxyphenyl, 3,4-dihydroxyphenyl, 2-aminophenyl, 2-acetoxyphenyl, 4-methoxymethoxyphenyl, 3-triethylsilyloxyphenyl, etc.

Specific examples of the saturated or unsaturated 3- to 7-membered alicyclic hydrocarbon group which $R^2$ and $R^3$ form when taken together with the carbon atom to which they are bonded are cyclopropylidene, cyclobutylidene, cyclopentylidene, 3-cyclopentenylidene, cyclohexylidene, 2,4-cyclohexadienylidene, cycloheptylidene, etc.

When any of $R^5$, $R^{11}$, $R^{14}$, $R^{15}$ and $R^{16}$ is a protected hydroxyl group, its hydroxyl-protecting group includes ether type protecting groups such as methyl, t-butyl, allyl, 3-methyl-2-butenyl, benzyl, triphenylmethyl, etc.; acetal type protecting groups such as methoxymethyl, tetrahydropyranyl, etc.; silyl ether type protecting groups such as trimethylsilyl, triethylsilyl, t-butyldimethylsilyl, etc.; ester type protecting groups such as acetyl, butanoyl, 2-methylpropanoyl, pivaloyl, hexanoyl, benzoyl, etc.; and carbonic ester type protecting groups such as t-butoxycarbonyl, 2,2,2-dichloroethoxycarbonyl, allyloxycarbonyl, benzyloxycarbonyl, 4-methoxybenzyloxycarbonyl, 4-nitrobenzyloxycarbonyl, etc.

When the substituent of the substituted aralkyl group or the substituted phenyl group is a protected hydroxyl group, its hydroxyl-protecting group includes the same protecting groups as those exemplified above.

The hydroxyl-protecting group for each of $R^{12}$ and $R^{13}$ includes ether type protecting groups such as methyl, t-butyl, allyl, 3-methyl-2-butenyl, benzyl, triphenylmethyl, etc.; acetal type protecting groups such as methoxymethyl, tetrahydropyranyl, etc.; silyl ether type protecting groups such as trimethylsilyl, triethylsilyl, t-butyldimethylsilyl, etc.; and carbonic ester type protecting groups such as t-butoxycarbonyl, 2,2,2-dichloroethoxycarbonyl, allyloxycarbonyl, benzyloxycarbonyl, 4-methoxybenzyloxycarbonyl, 4-nitrobenzyloxycarbonyl, etc.

The haloalkyl group of 2 to 6 carbon atoms includes linear or branched alkyl groups substituted by 1 to 5 halogen atoms (specific examples thereof are the same as those given above) which may be the same or different. Specific examples thereof are 2-chloroethyl, 2-bromoethyl, 2,2,2-trifluoroethyl, 2,2,3,3-tetrafluoropropyl, 2,2,3,3,3-pentafluoropropyl, 3-bromopropyl, 4-chlorobutyl, etc.

The hydroxyalkyl group of 2 to 6 carbon atoms includes linear or branched alkyl groups substituted by one or two hydroxyl groups. Specific examples thereof are 2-hydroxyethyl, 3-hydroxypropyl, 1-ethyl-2-hydroxyethyl, 2,3-dihydroxypropyl, 4-hydroxybutyl, 5-hydroxypentyl, 6-hydroxyhexyl, etc.

The alkyl group of 1 to 10 carbon atoms for each of $R^{18}$ and $R^{19}$ includes linear or branched alkyl groups. Specific examples thereof are heptyl, 1-ethylpentyl, 1-methylheptyl, octyl, 1,5-dimethylhexyl, 2-ethylhexyl, nonyl, decyl, etc. in addition to the specific examples of the above-mentioned alkyl group of 1 to 6 carbon atoms.

The phenyl-substituted or unsubstituted carboxyalkyl group of 2 to 7 carbon atoms for each of $R^{18}$ and $R^{19}$ includes linear or branched alkyl groups substituted by one or two carboxyl groups (in case of the phenyl-substituted carboxyalkyl group, the alkyl portion is substituted by phenyl group). Specific examples thereof are carboxymethyl, 1-carboxyethyl, 2-carboxyethyl, 3-carboxypropyl, 2-carboxy-1,1-dimethylethyl, 1,3-dicarboxypropyl, 5-carboxypentyl, 6-carboxyhexyl, 1-phenylcarboxymethyl, 1-carboxy-2-phenylethyl, etc.

The alkyl group of 1 to 19 carbon atoms for $R^{20}$ includes linear or branched alkyl groups. Specific examples thereof are undecyl, dodecyl, tridecyl, tetradecyl, pentadecyl, hexadecyl, heptadecyl, octadecyl, nonadecyl, etc. in addition to the specific examples of the above-mentioned alkyl groups.

The alkenyl group of 3 to 19 carbon atoms for $R^{20}$ includes linear or branched alkenyl groups. Specific examples thereof are 1-heptenyl, 2-octenyl, 1,3-octadienyl, 3-nonenyl, 1,3-nonadienyl, 9-decenyl, 8-tridecenyl, 8-pentadecenyl, 10-pentadecenyl, 8-heptadecenyl, 10-heptadecenyl, 8,11-heptadecadienyl, 8,11,14-heptadecatrienyl, 7,10,13-nonadecatrienyl, 4,7,10,13-nonadecatetraenyl, 4,7,10,13,16-nonadecapentaenyl, etc. in addition to the specific examples of the above-mentioned alkenyl group.

The 5- or 6-membered heterocyclic group for $R^{20}$ includes heterocyclic groups composed of 5 or 6 atoms in all, one or two of which are heteroatoms selected from the group consisting of nitrogen atom, oxygen atom and sulfur atom. Specific examples thereof are aromatic heterocyclic groups such as 2-furyl, 2-thienyl, 2-pyrrolyl, 1-imidazolyl, 2-thiazolyl, 2-pyridyl, 3-pyridyl, 4-pyridyl, etc.

As the pharmaceutically acceptable salt of the objective compound (I) of the present invention, there may be exemplified salts with inorganic bases, such as sodium salt, potassium salt, calcium salt, magnesium salt, ammonium salt, etc.; and salts with organic bases, such as triethylammonium salt, triethanolammonium salt, pyridinium salt, diisopropylammonium salt, etc. When the compound (I) has an amino group in the molecule, there may also be exemplified salts with inorganic acids, such as hydrochloride, hydrobromide, nitrate, sulfate, etc.; and salts with organic acids, such as acetate, propionate, trifluoroacetate, citrate, maleate, tartrate, methanesulfonate, benzenesulfanate, etc.

The present invention also includes solvates (e.g. hydrates) of the compounds described above.

The compound of the general formula (I) of the present invention may be produce, for example, by any of the processes described below or a well-known technique. First, there is explained below a production process thereof employed when $A^1$ is —CO— and Z is a group of the general formula (IIa).

Case 1. When k is 0.

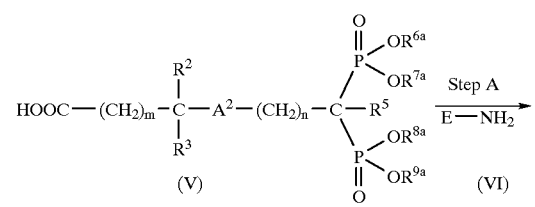

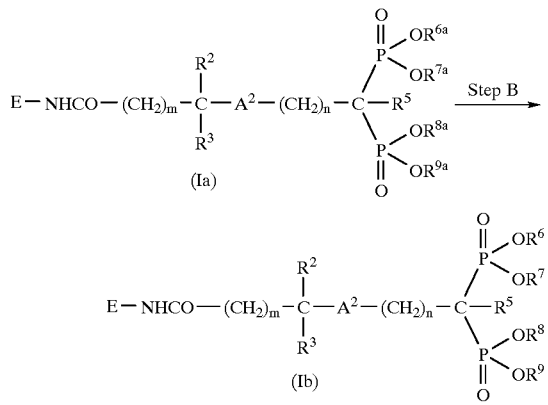

wherein E, $R^2$, $R^3$, $R^5$, $R^6$, $R^7$, $R^8$, $R^9$, $A^2$, m and n are as defined above, and $R^{6a}$, $R^{7a}$, $R^{8a}$ and $R^{9a}$ are independently an alkyl group of 1 to 6 carbon atoms, a haloalkyl group of 2 to 6 carbon atoms, an allyl group, a benzyl group or a group of the formula —$CH_2$—O—CO—$R^{10}$ (wherein $R^{10}$ is as defined above).

Step A

An amide compound of the general formula (Ia) may be obtained by reacting a compound of the general formula (V) with a carboxylic acid activating agent (e.g. dicyclohexylcarbodiimide, isobutyl chloroformate, N,N'-carbonyldiimidazole, thionyl chloride or oxalyl dichloride, etc) in a suitable solvent to activate the carboxyl group of the compound of the general formula (V), and then reacting the reaction product with a compound of the general formula (VI) in the presence of a suitable base. As the suitable solvent, any solvent may be used so long as it has no undesirable influence on the reaction. The suitable solvent includes halogenated hydrocarbon solvents such as methylene chloride, chloroform, carbon tetrachloride, 1,2-dichloroethane, etc.; halogenated aromatic hydrocarbon solvents such as monochlorobenzene, o-dichlorobenzene, etc.; ether solvents such as diethyl ether, tetrahydrofuran, dioxane, 1,2-dimethoxyethane, etc.; dimethylformamide; dimethyl sulfoxide; acetonitrile; hexamethylphosphoramide; and mixed solvents obtained by arbitrary combination of these solvents. Especially preferable examples thereof are methylene chloride, chloroform, tetrahydrofuran, dioxane, dimethylformamide and dimethyl sulfoxide. As the suitable base, there may be exemplified organic bases such as pyridine, collidine, 4-dimethylaminopyridine, triethylamine, N,N-diisopropyl-ethylamine, N-methylmorpholine, 1,8-diazabicyclo[5,4,0]-undec-7-ene (DBU), etc. Especially preferable examples thereof are 4-dimethylaminopyridine, triethylamine and N,N-diisopropylethylamine. It is preferable to activate the carboxyl group of the compound of the general formula (V) by adding the carboxylic acid activating agent in an amount of 1 to 2 equivalents per equivalent of the compound of the general formula (V), and then add the base and the compound of the general formula (VI) in amounts of 1 to 4 equivalents and 1 to 2 equivalents, respectively, per equivalent of the compound having the activated carboxyl group, to carry out the reaction. Although the reaction temperatures are not particularly limited, the reactions are carried out usually at −50° C. to 150° C., preferably −30° C. to 50° C.

A compound of the general formula (V) in which $R^5$ is a hydrogen atom, a halogen atom or a methyl group may be produced from, for example, a corresponding tetraalkyl methylenebisphosphonate or tetraalkyl ethenylidenebisphosphonate by the same process as a conventional technique (for instance, the process disclosed in Japanese Patent Unexamined Publication No. 5-222073, J. Organometal. Chem., 13, 199–207 (1968), or Synthesis, 661–662 (1991)). The tetraalkyl methylenebisphosphonate as starting compound may be synthesized by the process disclosed in the specification of U.S. Pat. No. 3,251,907 (Chem. Abstr., 65, 3908d (1966)) and Synth. Commun., 20, 1865–1867 (1990)). The tetraalkyl ethenylidenebisphosphonate as starting compound may be synthesized by the process described in J. Org. Chem., 51, 3488–3490 (1986). In addition, a compound of the general formula (V) in which $R^5$ is a hydroxyl group or a protected hydroxyl group may be produced from, for example, a corresponding carboxylic acid by the same process as a conventional technique (for instance, the process disclosed in Japanese Patent Unexamined Publication No. 6-135976).

The compound of the general formula (VI) may be produced via, for example, a corresponding nitro compound by a conventional technique (described in, for instance, J. Org. Chem., 38, 3525–3533 (1973)).

Step B

When $R^5$ is a protected hydroxyl group and each of $R^{12}$ and $R^{13}$ of E is a hydroxyl-protecting group in the compound of the general formula (Ia), deprotection is carried out if desired. The deprotection may be carried out by a conventional method, for example, the method described in Protective Groups in Organic Synthesis 2nd Edition, T. W. Greene and P. G. M. Wuts, John Wiley and Sons, Inc., 15–86, 145–162 (1991). When the bisphosphonic acid ester is then converted to a bisphosphonic acid by request, a compound of the general formula (Ib) in which at least one of $R^6$, $R^7$, $R^8$ and $R^9$ is hydrogen atom may be obtained, for example, by a process using a halosilane such as iodotrimethylsilane or bromotrimethylsilane, etc. (Aldrichimica Acta, 14, 267–274 (1981)) or a process using hydrochloric acid (J. Med. Chem., 30, 1426–1433 (1987)). When at least one of $R^{6a}$, $R^{7a}$, $R^{8a}$ and $R^{9a}$ is a benzyl group in the compound of the general formula (Ia), there may be practiced a process employing hydrogenolysis with a palladium catalyst such as metallic palladium or palladium hydroxide (for instance, the process disclosed in Japanese Patent Unexamined Publication No. 6-329697). When at least one of $R^{6a}$, $R^{7a}$, $R^{8a}$ and $R^{9a}$ is an allyl group, there may be practiced a process using a combination of a palladium catalyst (e.g. tetrakis(triphenylphosphine)palladium, etc.) and an allyl receptor (e.g. potassium 2-ethyl-hexanoate, pyrrolidine, aniline or dimedone, etc.). In this case, the hydroxyl-protecting group of $R^5$ and the hydroxyl-protecting groups for $R^{12}$ and $R^{13}$ may be removed at the same time if desired.

Case 2. When k is 0 and A2 is a single bond.

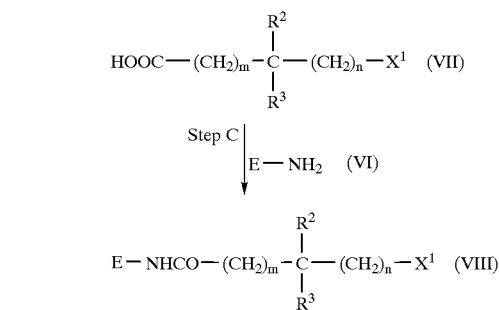

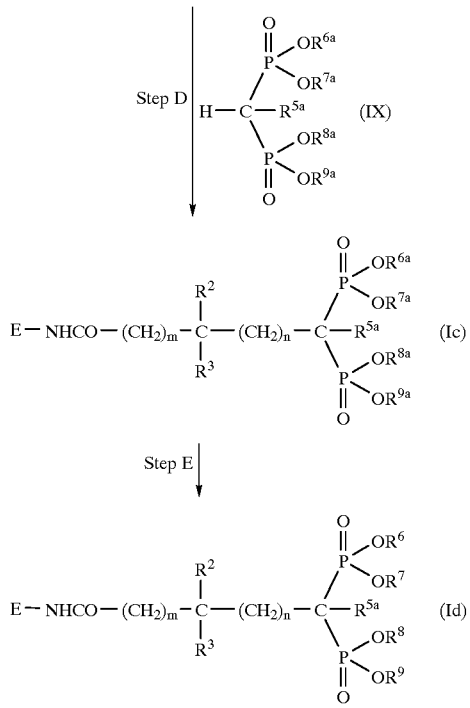

(wherein E, $R^2$, $R^3$, $R^6$, $R^7$, $R^8$, $R^9$, $R^{6a}$, $R^{7a}$, $R^{8a}$, $R^{9a}$, m and n are as defined above, $R^{5a}$ is a hydrogen atom or a methyl group, and $X^1$ is an acid residue, preferably a chlorine atom, a bromine atom, an iodine atom, a methanesulfonyloxy group or a 4-toluenesulfonyloxy group).

Step C

An amide compound of the general formula (VIII) may be obtained by reacting a compound of the general formula (VII) with a carboxylic acid activating agent (e.g. dicyclohexylcarbodiimide, isobutyl chloroformate, N,N'-carbonyldiimidazole, thionyl chloride or oxalyl dichloride, etc.) in a suitable solvent to activate the carboxyl group of the compound of the general formula (VII), and then reacting the reaction product with a compound of the general formula (VI) in the presence of a suitable base. This step may be carried out in the same manner as described in the above step A.

Step D

A compound of the general formula (Ic) may be obtained by reacting a methylenebisphosphonate derivative of the general formula (IX) in a suitable solvent in the presence of a suitable base by the same method as described in J. Organometal. Chem., 13, 199–207 (1968) to obtain a carbanion, and then reacting the carbanion with the compound of the general formula (VIII). As the suitable solvent, any solvent may be used so long as it has no undesirable influence on the reaction. The suitable solvent includes aromatic hydrocarbon solvents such as benzene, toluene, o-xylene, etc.; halogenated hydrocarbon solvents such as methylene chloride, chloroform, carbon tetrachloride, 1,2-dichloroethane, etc.; halogenated aromatic hydrocarbon solvents such as monochlorobenzene, o-dichlorobenzene, etc.; ether solvents such as diethyl ether, tetrahydrofuran, dioxane, 1,2-dimethoxyethane, etc.; dimethylformamide; dimethyl sulfoxide; acetonitrile; hexamethylphosphoramide; and mixed solvents obtained by arbitrary combination of these solvents. Especially preferable examples thereof are benzene, toluene, methylene chloride, chloroform, tetrahydrofuran, dioxane, dimethylformamide and dimethyl sulfoxide. As the suitable base, there may be exemplified sodium hydride, potassium hydride and potassium t-butoxide, etc. Especially preferable examples thereof are sodium hydride and potassium hydride. It is preferable to carry out the reactions by using the base and the compound of the general formula (VIII) in amounts of 1 to 4 equivalents and 1 to 2 equivalents, respectively, per equivalent of the compound of the general formula (IX). Although the reaction temperatures are not particularly limited, the reactions are carried out usually at −50° C. to 200° C., preferably −30° C. to 150° C.

The compound of the general formula (IX) may be produced by the same process as a conventional technique [for instance, the process disclosed in the specification of U.S. Pat. No. 3,251,907 (Chem. Abstr., 65, 3908d (1966)), Synth. Commun., 20, 1865–1867 (1990), and J. Organomental. Chem., 13, 199–207 (1968)].

Step E

When each of $R^{12}$ and $R^{13}$ of E is a hydroxyl-protecting group in the compound of the general formula (Ic), deprotection and then the conversion of the bisphosphonic acid ester to a bisphosphonic acid may, if desired, be carried out in the same manners, respectively, as described in the above step B.

Case 3. When k is 1.

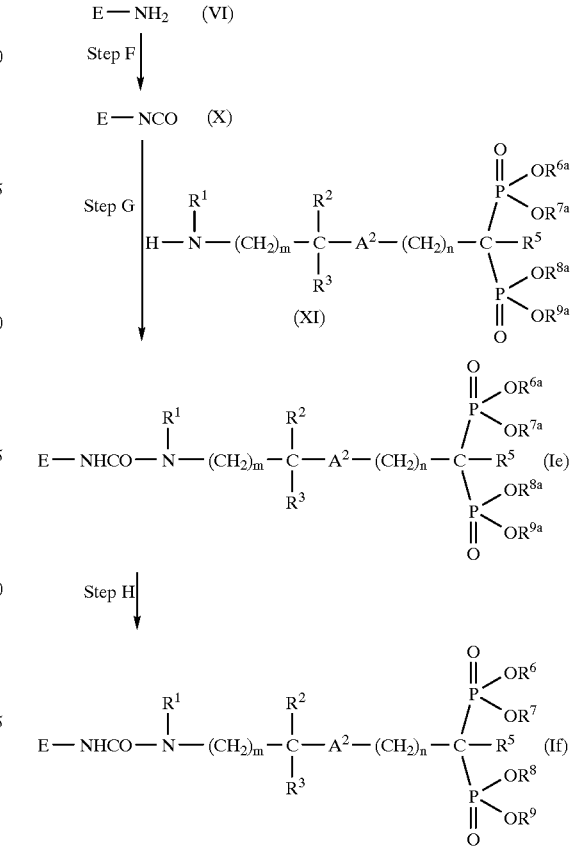

wherein E, $R^1$, $R^2$, $R^3$, $R^5$, $R^6$, $R^7$, $R^8$, $R^9$, $A^2$, $R^{6a}$, $R^{7a}$, $R^{8a}$, $R^{9a}$, m and n are as defined above.

Step F

An isocyanate compound of the general formula (X) may be obtained by reacting a compound of the general formula (VI) with phosgene or its analog (e.g. diphosgene, triphosgene or N,N'-carbonyldiimidazole, etc.) in a suitable solvent optionally in the presence of a suitable base. As the suitable solvent, any solvent may be used so long as it has no undesirable influence on the reaction. The suitable solvent includes halogenated hydrocarbon solvents such as methylene chloride, chloroform, carbon tetrachloride, 1,2-dichloroethane, etc.; halogenated aromatic hydrocarbon solvents such as monochlorobenzene, o-dichlorobenzene, etc.; ether solvents such as diethyl ether, tetrahydrofuran, dioxane, 1,2-dimethoxyethane, etc.; dimethylformamide; dimethyl sulfoxide; acetonitrile; hexamethylphosphoramide; and mixed solvents obtained by arbitrary combination of these solvents. Especially preferable examples thereof are methylene chloride, chloroform, carbon tetrachloride, 1,2-dichloroethane, monochlorobenzene and o-dichlorobenzene. As the suitable base, there may be exemplified organic bases such as pyridine, collidine, 4-dimethylaminopyridine, triethylamine, N,N-diisopropylethylamine, N-methylmorpholine, DBU, etc. Especially preferable examples thereof are pyridine, collidine, 4-dimethylaminopyridine, triethylamine and N,N-diisopropylethylamine. It is preferable to carry out the reaction by adding phosgene or its analog and the base in amounts of 1 to 4 equivalents and 0 to 4 equivalents, respectively, per equivalent of the compound of the general formula (VI). Although the reaction temperature is not particularly limited, the reaction is carried out usually at 0° C. to 150° C., preferably 10° C. to 120° C.

Step G

A compound of the general formula (Ie) may be obtained by reacting the compound of the general formula (X) with a compound of the general formula (XI) in a suitable solvent optionally in the presence of a suitable base. As the suitable solvent, any solvent may be used so long as it has no undesirable influence on the reaction. The suitable solvent includes halogenated hydrocarbon solvents such as methylene chloride, chloroform, carbon tetrachloride, 1,2-dichloroethane, etc.; halogenated aromatic hydrocarbon solvents such as monochlorobenzene, o-dichlorobenzene, etc.; ether solvents such as diethyl ether, tetrahydrofuran, dioxane, 1,2-dimethoxyethane, etc.; dimethylformamide; dimethyl sulfoxide; acetonitrile; hexamethylphosphoramide; and mixed solvents obtained by arbitrary combination of these solvents. Especially preferable examples thereof are methylene chloride, chloroform, tetrahydrofuran, dioxane, dimethylformamide and dimethyl sulfoxide. As the suitable base, there may be exemplified organic bases such as pyridine, collidine, 4-dimethylaminopyridine, triethylamine, N,N-diisopropylethylamine, N-methylmorpholine, DBU, etc. Especially preferable examples thereof are 4-dimethylaminopyridine, triethylamine and N,N-diisopropylethylamine. It is preferable to carry out the reaction by adding the compound of the general formula (XI) and the base in amounts of 1 to 4 equivalents and 0 to 4 equivalents, respectively, per equivalent of the compound of the general formula (X). Although the reaction temperature is not particularly limited, the reaction is carried out usually at −50° C. to 150° C., preferably −20° C. to 50° C.

A compound of the general formula (XI) in which $R^5$ is a hydrogen atom, a halogen atom or a methyl group may be produced from, for example, a corresponding tetraalkyl methylenebisphosphonate or tetraalkyl ethenylidenebisphosphonate by the same process as a conventional technique (for instance, the process disclosed in Japanese Patent Unexamined Publication No. 5-222073, J. Organometal. Chem., 13, 199–207 (1968), or Synthesis, 661–662 (1991)). The tetraalkyl methylenebisphosphonate as starting compound may be synthesized by the process disclosed in the specification of U.S. Pat. No. 3,251,907 (Chem. Abstr., 65, 3908d (1966)) and Synth. Commun., 20, 1865–1867 (1990)). The tetraalkyl ethenylidenebisphosphonate as starting compound may be synthesized by the process described in J. Org. Chem., 51, 3488–3490 (1986). In addition, a compound of the general formula (XI) in which $R^5$ is a hydroxyl group or a protected hydroxyl group may be produced from, for example, a corresponding carboxylic acid by the same process as a conventional technique (for instance, the process disclosed in Japanese Patent Unexamined Publication No. 6-135976).

Step H

When $R^5$ is a protected hydroxyl group and each of $R^{12}$ and $R^{13}$ of E is a hydroxyl-protecting group in the compound of the general formula (Ie), deprotection and then the conversion of the bisphosphonic acid ester to a bisphosphonic acid may, if desired, be carried out in the same manners, respectively, as described in the above step B.

Also when Z is a group of the general formula (IIb), (IIc) or (IId), a compound corresponding to the compound of the general formula (If) may be obtained through the same steps as steps F, G and H.

Case 4. When k is 0 and $A^2$ is a group of the formula —$NR^4$—.

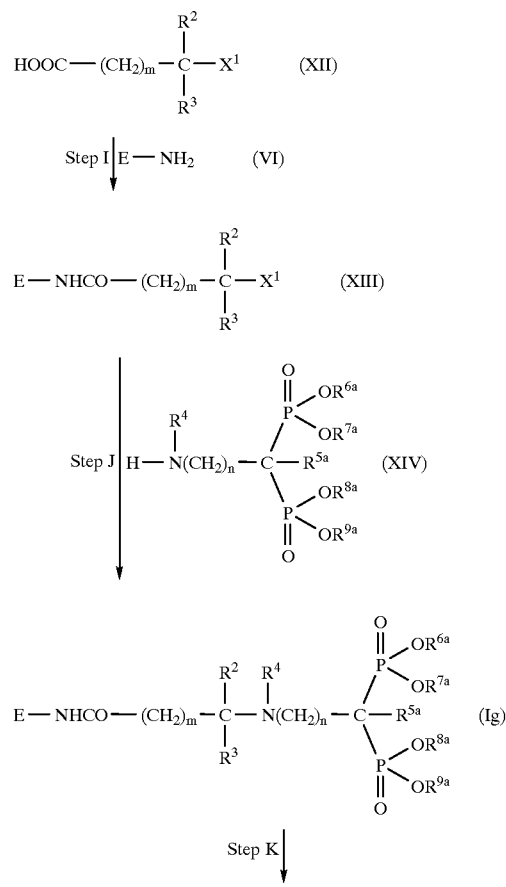

-continued

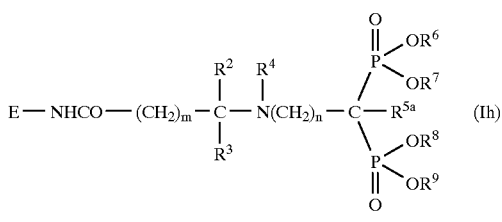

wherein E, $R^2$, $R^3$, $R^4$, $R^{5a}$, $R^6$, $R^7$, $R^8$, $R^9$, $R^{6a}$, $R^{7a}$, $R^{8a}$, $R^{9a}$, $X^1$, m and n are as defined above.

Step I

An amide compound of the general formula (XIII) may be obtained by reacting a compound of the general formula (XII) with a carboxylic acid activating agent (e.g. dicyclohexylcarbodiimide, isobutyl chloroformate, N,N'-carbonyldiimidazole, thionyl chloride or oxalyl dichloride, etc.) in a suitable solvent to activate the carboxyl group of the compound of the general formula (XII), and then reacting the reaction product with a compound of the general formula (VI) in the presence of a suitable base. This step may be carried out in the same manner as described in the above step A.

Step J

A compound of the general formula (Ig) may be obtained by reacting the compound of the general formula (XIII) with an aminoalkanebisphosphonic acid derivative of the general formula (XIV) in a suitable solvent optionally in the presence of a suitable base. As the suitable solvent, any solvent may be used so long as it has no undesirable influence on the reaction. The suitable solvent includes halogenated hydrocarbon solvents such as methylene chloride, chloroform, carbon tetrachloride, 1,2-dichloroethane, etc.; halogenated aromatic hydrocarbon solvents such as monochlorobenzene, o-dichlorobenzene, etc.; ether solvents such as diethyl ether, tetrahydrofuran, dioxane, 1,2-dimethoxyethane, etc.; dimethylformamide; dimethyl sulfoxide; acetonitrile; hexamethylphosphoramide; and mixed solvents obtained by arbitrary combination of these solvents. Especially preferable examples thereof are methylene chloride, chloroform, tetrahydrofuran, dioxane, dimethylformamide and dimethyl sulfoxide. As the suitable base, there may be exemplified organic bases such as pyridine, collidine, 4-dimethylaminopyridine, triethylamine, N,N-diisopropylethylamine, N-methylmorpholine, DBU, etc. Especially preferable examples thereof are 4-dimethylaminopyridine, triethylamine and N,N-diisopropylethylamine. It is preferable to carry out the reaction by adding the compound of the general formula (XIV) and the base in amounts of 1 to 4 equivalents and 0 to 4 equivalents, respectively, per equivalent of the compound of the general formula (XIII). Although the reaction temperature is not particularly limited, the reaction is carried out usually at −50° C. to 150° C., preferably −20° C. to 120° C.

The aminoalkanebisphosphonic acid derivative of the general formula (XIV) may be produced by the same process as a conventional technique.

Step K

When each of $R^{12}$ and $R^{13}$ of E is a hydroxyl-protecting group in the compound of the general formula (Ig), deprotection and then the conversion of the bisphosphonic acid ester to a bisphosphonic acid may, if desired, be carried out in the same manners, respectively, as described in the above step B.

Case 5. When k is 0 and $A^2$ is a group of the formula —CO—$NR^4$—.

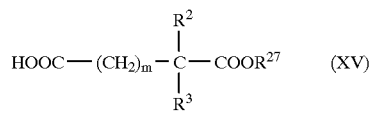

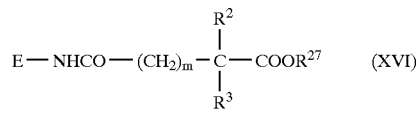

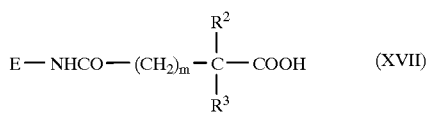

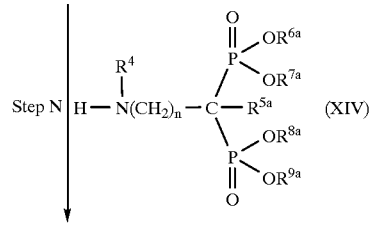

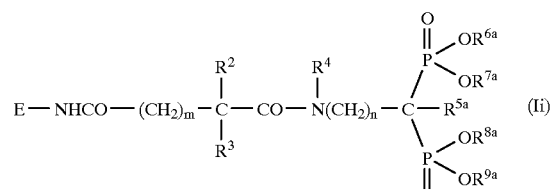

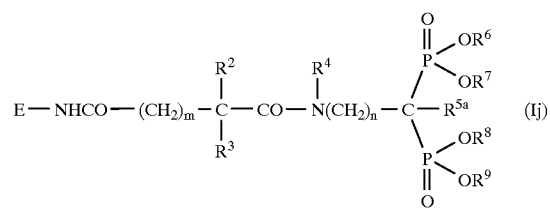

wherein E, $R^2$, $R^3$, $R^4$, $R^6$, $R^7$, $R^8$, $R^9$, $R^{5a}$, $R^{6a}$, $R^{7a}$, $R^{8a}$, $R^{9a}$, m and n are as defined above, and $R^{27}$ is a carboxyl-protecting group, specific examples of which are linear or branched alkyl groups of 1 to 6 carbon atoms, such as methyl, ethyl, isopropyl, t-butyl, etc.; unsubstituted or substituted benzyl groups such as benzyl, 4-methoxy-benzyl, 4-nitrobenzyl, etc.; and allyl group.

Step L

An amide compound of the general formula (XVI) may be obtained by reacting a compound of the general formula (XV) with a carboxylic acid activating agent (e.g. dicyclohexylcarbodiimide, isobutyl chloroformate, N,N'-carbonyldiimidazole, thionyl chloride or oxalyl dichloride, etc.) in a suitable solvent to activate the carboxyl group of the compound of the general formula (XV), and then reacting the reaction product with a compound of the general formula (VI) in the presence of a suitable base. This step may be carried out in the same manner as described in the above step A.

Step M

This step is a step of removing the carboxyl-protecting group $R^{27}$ of the compound of the general formula (XVI), and reaction conditions suitable for the carboxyl-protecting group $R^{27}$ may be employed in this step. The deprotection may be carried out by a conventional method, for example, the method described in Protective Groups in Organic Synthesis 2nd Edition, T. W. Greene and P. G. M. Wuts, John Wiley and Sons, Inc., 15–86, 224–276 (1991).

Step N

A compound of the general formula (Ii) may be obtained by reacting a compound of the general formula (XVII) with a carboxylic acid activating agent (e.g. dicyclohexylcarbodiimide, isobutyl chloroformate, N,N'-carbonyldiimidazole, thionyl chloride or oxalyl dichloride, etc.) in a suitable solvent to activate the carboxyl group of the compound of the general formula (XVII), and then reacting the reaction product with an aminoalkanebisphosphonic acid derivative of the general formula (XIV) in the presence of a suitable base. This step may be carried out in the same manner as described in the above step A.

Step O

When each of $R^{12}$ and $R^{13}$ of E is a hydroxyl-protecting group in the compound of the general formula (Ii), deprotection and then the conversion of the bisphosphonic acid ester to a bisphosphonic acid may, if desired, be carried out in the same manners, respectively, as described in the above step B.

Case 6. When k is 0, $A^2$ is a group of the formula $-NR^4-$, and n is 1.

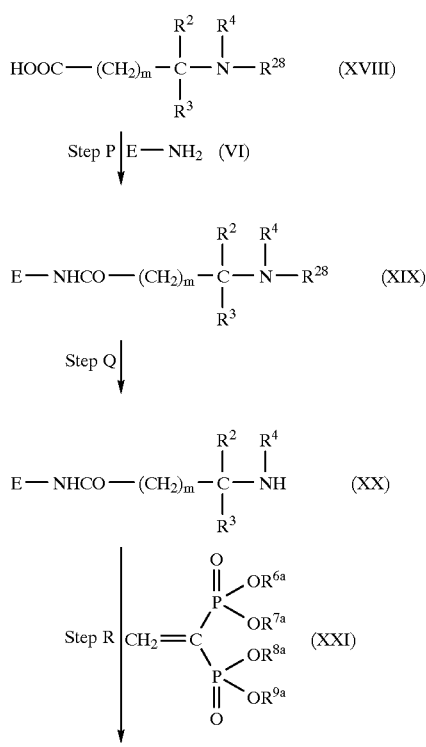

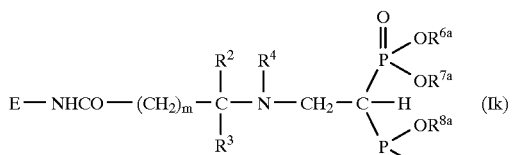

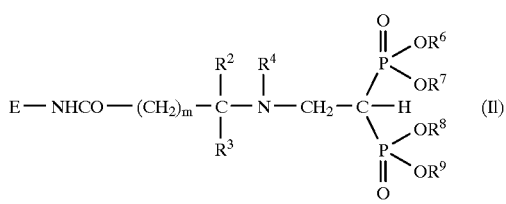

wherein E, $R^2$, $R^3$, $R^4$, $R^6$, $R^7$, $R^8$, $R^9$, $R^{6a}$, $R^{7a}$, $R^{8a}$, $R^{9a}$ and m are as defined above, and $R^{28}$ is an amino-protecting group, for example, a carbamate type protecting group such as t-butoxycarbonyl, 2,2,2-trichloroethoxycarbonyl, allyloxycarbonyl, benzyloxycarbonyl, 4-methoxybenzyloxycarbonyl or 4-nitrobenzyloxycarbonyl, or a trifluoroacetyl group.

Step P

An amide compound of the general formula (XIX) may be obtained by reacting a compound of the general formula (XVIII) with a carboxylic acid activating agent (e.g. dicyclohexylcarbodiimide, isobutyl chloroformate, N,N'-carbonyldiimidazole, thionyl chloride or oxalyl dichloride, etc.) in a suitable solvent to activate the carboxyl group of the compound of the general formula (XVIII), and then reacting the reaction product with a compound of the general formula (VI) in the presence of a suitable base. This step may be carried out in the same manner as described in the above step A.

Step Q

This step is a step of removing the amino-protecting group $R^{28}$ of the compound of the general formula (XIX), and reaction conditions suitable for the protecting group $R^{28}$ may be employed in this step. The deprotection may be carried out by a conventional method, for example, the method described in Protective Groups in Organic Synthesis 2nd Edition, T. W. Greene and P. G. M. Wuts, John Wiley and Sons, Inc., 15–86, 321–341 (1991).

Step R

A compound of the general formula (Ik) may be obtained by subjecting a compound of the general formula (XX) to Michael addition reaction with an ethenylidene-bisphosphonic acid derivative of the general formula (XXI) in a suitable solvent by the same method as described in J. Organometal. Chem., 346, 341–348 (1988). As the suitable solvent, any solvent may be used so long as it has no undesirable influence on the reaction. The suitable solvent includes halogenated hydrocarbon solvents such as methylene chloride, chloroform, carbon tetrachloride, 1,2-dichloroethane, etc.; halogenated aromatic hydrocarbon solvents such as monochlorobenzene, o-dichlorobenzene, etc.; ether solvents such as diethyl ether, tetrahydrofuran, dioxane, 1,2-dimethoxyethane, etc.; alcohol solvents such as methanol, ethanol, isopropanol, n-butanol, etc.; dimethylformamide; dimethyl sulfoxide; acetonitrile; hexamethylphosphoramide; and mixed solvents obtained by arbitrary combination of these solvents. Especially preferable examples thereof are methylene chloride, chloroform, tetrahydrofuran, dioxane, methanol, ethanol, isopropanol, dimethylformamide and dimethyl sulfoxide. It is preferable to carry out the reaction by using the compound of the general formula (XXI) in an amount of 1 to 2 equivalents per equivalent of the compound of the general formula (XX). Although the reaction temperature is not particularly limited, the reaction is carried out usually at −30° C. to 200° C., preferably 0° C. to 100° C.

The compound of the general formula (XXI) may be produced from, for example, a corresponding tetra-alkyl methylenebisphosphonate by the same process as a conventional technique (for instance, the process described in J. Org. Chem., 51, 3488–3490 (1986)).

Step S

When each of $R^{12}$ and $R^{13}$ of E is a hydroxyl-protecting group in the compound of the general formula (Ik), deprotection and then the conversion of the bisphosphonic acid ester to a bisphosphonic acid may, if desired, be carried out in the same manners, respectively, as described in the above step B.

Next, there is explained below a process for producing a compound of the general formula (I) in which $A^1$ is —$SO_2$—, Z is a group of the general formula (IIa), and k is 0.

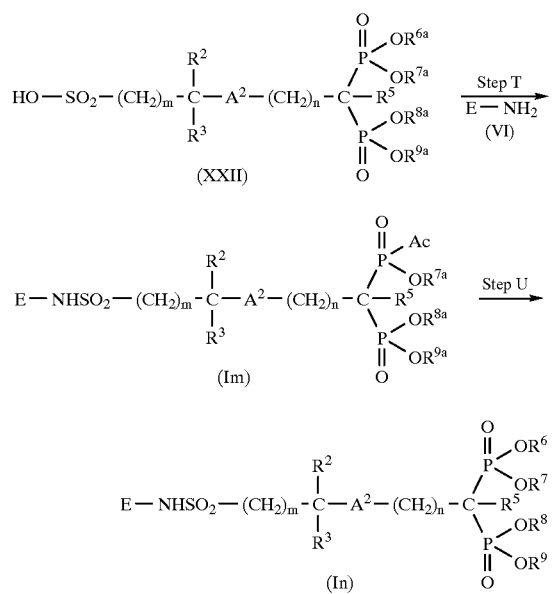

wherein E, $R^2$, $R^3$, $R^5$, $R^6$, $R^7$, $R^8$, $R^9$, $R^{6a}$, $R^{7a}$, $R^{8a}$, $R^{9a}$, $A^2$, m and n are as defined above.

Step T

A sulfonamide compound of the general formula (Im) may be obtained by treating a compound of the general formula (XXII) with a chlorinating agent such as phosphorus oxychloride, etc. to obtain a sulfonyl chloride, and then reacting the sulfonyl chloride with a compound of the general formula (VI) in a suitable solvent in the presence of a suitable base. As the suitable solvent, any solvent may be used so long as it has no undesirable influence on the reaction. The suitable solvent includes halogenated hydrocarbon solvents such as methylene chloride, chloroform, carbon tetrachloride, 1,2-dichloroethane, etc.; halogenated aromatic hydrocarbon solvents such as monochlorobenzene, o-dichlorobenzene, etc.; ether solvents such as diethyl ether, tetrahydrofuran, dioxane, 1,2-dimethoxyethane, etc.; dimethylformamide; dimethyl sulfoxide; acetonitrile; hexamethylphosphoramide; and mixed solvents obtained by arbitrary combination of these solvents. Especially preferable examples thereof are methylene chloride, chloroform, tetrahydrofuran, dioxane, dimethylformamide and dimethyl sulfoxide. As the suitable base, there may be exemplified organic bases such as pyridine, collidine, 4-dimethylaminopyridine, triethylamine, N,N-diisopropylethylamine, N-methylmorpholine, DBU, etc. Especially preferable examples thereof are 4-dimethylaminopyridine, triethylamine and N,N-diisopropylethylamine. It is preferable to convert the compound of the general formula (XXII) to the sulfonyl chloride by using the chlorinating agent in an amount of 1 to 4 equivalents per equivalent of the compound of the general formula (XXII), and then react the sulfonyl chloride with the compound of the general formula (VI) by adding the base and the compound of the general formula (VI) in amounts of 1 to 4 equivalents and 1 to 2 equivalents, respectively, per equivalent of the sulfonyl chloride. Although the reaction temperatures are not particularly limited, the reactions are carried out usually at −50° C. to 150° C., preferably −30° C. to 50° C.

Step U

When $R^5$ is a protected hydroxyl group and each of $R^{12}$ and $R^{13}$ of E is a hydroxyl-protecting group in the compound of the general formula (Im), deprotection and then the conversion of the bisphosphonic acid ester to a bisphosphonic acid may, if desired, be carried out in the same manners, respectively, as described in the above step B.

Also when $A^1$ is —$SO_2$—, Z is a group of the general formula (IIb), (IIc) or (IId) and k is 0, a compound corresponding to a compound of the general formula (In) may be synthesized through the same steps as step T and step U.

Next, there is explained below a process for producing a compound of the general formula (I) in which $A^1$ is —CO—, Z is a group of the general formula (IIb), (IIc) or (IId) and k is 0.

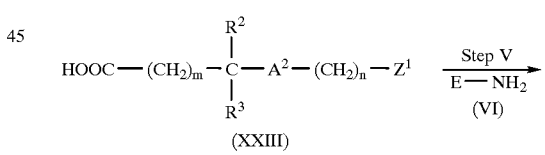

wherein E, $R^2$, $R^3$, $A^2$, m and n are as defined above, and $Z^1$ is a group of the general formula (IIb$^1$), (IIc$^1$) or (IId$^1$):

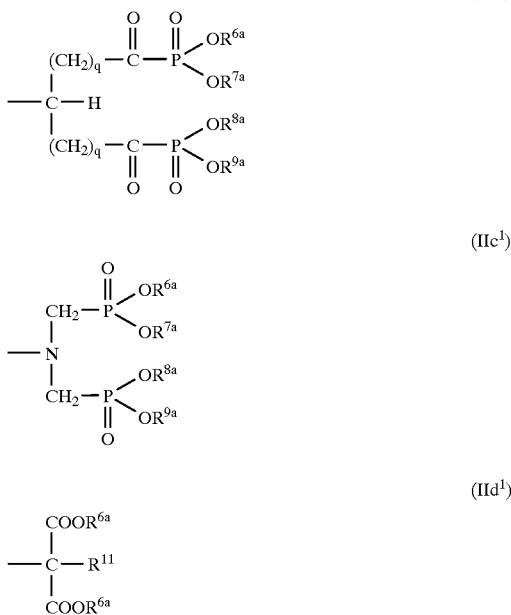

wherein $R^{6a}$, $R^{7a}$, $R^{8a}$, $R^{9a}$, $R^{11}$ and q are as defined above).

Step V

An amide compound of the general formula (Io) may be obtained by reacting a compound of the general formula (XXIII) with a carboxylic acid activating agent (e.g. dicyclohexylcarbodiimide, isobutyl chloroformate, N,N'-carbonyldiimidazole, thionyl chloride or oxalyl dichloride, etc.) in a suitable solvent to activate the carboxyl group of the compound of the general formula (XXIII), and then reacting the reaction product with a compound of the general formula (VI) in the presence of a suitable base. This step may be carried out in the same manner as described in the above step A.

A compound of the general formula (XXIII) in which $Z^1$ is a group of the general formula ($IIb^1$) may be produced from, for example, a corresponding malonic acid derivative or glutaric acid derivative by the same process as a conventional technique (for instance, the process described in Pharmaceutical Research, 9, 143–148 (1992)).

A compound of the general formula (XXIII) in which $Z^1$ is a group of the general formula ($IIc^1$) may be produced from, for example, a corresponding amine derivative by the same process as a conventional technique (for instance, the process disclosed in Japanese Patent Unexamined Publication No. 6-298779).

A compound of the general formula (XXIII) in which $Z^1$ is a group of the general formula ($IId^1$) may be produced from, for example, a corresponding malonic acid derivative or tartronic acid derivative by the same process as a conventional technique (for instance, the processes disclosed in WO9409770 and WO9410127).

Step W

When $R^{11}$ of Z is a protected hydroxyl group and each of $R^{12}$ and $R^{13}$ of E is a hydroxyl-protecting group in the compound of the general formula (Io), deprotection and then the conversion of the bisphosphonic acid ester to a bisphosphonic acid may, if desired, be carried out in the same manners, respectively, as described in the above step B.

The production processes comprising two to four of the above-mentioned steps A to W are detailed examples of processes for producing the compound of the general formula (I) of the present invention, but they do not limit a process for producing said compound, which includes starting materials, production procedures, reaction conditions, treatment conditions, etc.

In addition, each of some compounds (I) of the present invention has optical isomers due to at least one asymmetric carbon atom and stereoisomers. All of these isomers are represented by a single formula for convenience, but this formula is not intended to limit the scope of the present invention and the present invention includes all of these isomers and mixtures of the isomers.

Further, the compound of the present invention may be an anhydrous form or a solvate such as a hydrate, etc.

When used for preventing or treating osteoporosis, in particular, postmenopausal osteoporosis, the compound (I) or pharmaceutically acceptable salt thereof of the present invention may be administered as a pharmaceutical composition orally or parenterally (for example, by intravenous, subcutaneous or intramuscular injection, locally, intrarectally, percutaneously, or through nose). Compositions for the oral administration include, for example, tablets, capsules, pills, granules, powders, solutions and suspensions, etc. Compositions for the parenteral administration include, for example, aqueous or oily preparations for injection, ointments, creams, lotions, aerosols, suppositories and patches, etc. These pharmaceutical compositions are prepared by conventional techniques and may contain non-toxic and inactive carriers or excipients conventionally used in the field of formulation.

Although the dose is varied depending on the conditions (e.g. age and body weight, etc.) of a patient, symptom and administration route, the pharmaceutical composition is administered to an adult usually in a dose of 0.5 to 500 mg (in terms of the active ingredient of the present invention) per day in one to three portions on consecutive days or periodically or intermittently.

Specific examples of compounds included in the present invention are the following compounds. These compounds, however, are for exemplification, and the present invention is not limited thereto.

Erythro 3-(3-(4,4-diphosphonobutyrylamino)-4-hydroxyphenyl)-4-(4-hydroxyphenyl)hexane, Erythro 3-(3-(4,4-diphosphonobutyrylamino)-4-hexanoyloxyphenyl)-4-(4-hexanoyloxyphenyl)hexane, Erythro 3-(3-(4,4-diphosphonobutyrylamino)-4-heptanoyloxyphenyl)-4-(4-heptanoyloxyphenyl)hexane, Erythro 4-(3-cyclopentylpropionyloxyphenyl)-3-(4-cyclopentylpropionyloxy-3-(4,4-diphosphonobutyrylamino)phenyl)hexane, Erythro 3-(3-(4,4-diphosphonobutyrylamino)-4-linoleoyloxyphenyl)-4-(4-linoleoyloxyphenyl)hexane, Erythro 3-(3-(4,4-diphosphonobutyrylamino)-4-stearoyloxyphenyl)-4-(4-stearoyloxyphenyl)hexane, Erythro 3-(3-(4,4-diphosphonobutyrylamino)-4-eicosapentaenoyloxyphenyl)-4-(4-eicosapentaenoyloxyphenyl)hexane, Erythro 4-(3-cyclopentylpropionyloxyphenyl)-3-(3-(4,4-diphosphonobutyrylamino)-4-hydroxyphenyl)hexane, Erythro 3-(3-(4,4-diphosphonobutyrylamino)-4-hydroxyphenyl)-4-(4-linoleoyloxyphenyl)hexane, Erythro 3-(3-(4,4-diphosphonobutyrylamino)-4-saccharinylmethyloxyphenyl)-4-(4-saccharinylmethyloxyphenyl)hexane, Erythro 3-(3-(4,4-bis(dipivaloyloxymethoxyphosphinoyl)butyrylamino)-4-hexanoyloxyphenyl)-4-(4-hexanoyloxyphenyl)hexane, Erythro 3-(3-(4,4-bis(dipivaloyloxymethoxyphosphinoyl) butyrylamino)-4-saccharinylmethyloxyphenyl)-4-(4-saccharinylmethyloxyphenyl)hexane, Erythro 3-(3-(4,4-bis(dipivaloyloxymethoxyphosphinoyl) butyrylamino)-4-(N,N-dihexylamino)carbonyloxyphenyl)-4-(4-(N,N-dihexylamino)carbonyloxyphenyl)hexane, Erythro 1-acetoxy-3-(3-(4,4-diphosphonobutyrylamino)-4-acetoxyphenyl)-4-(4-acetoxyphenyl)hexane, Erythro 3-(3-(4,4-diphosphonobutyrylamino)-4-hydroxyphenyl)-1-fluoro-4-(4-hydroxyphenyl)hexane, Erythro 3-(3-(5,5-diphosphonovalerylamino)-4-(1-imidazolylcarbonyloxy)phenyl)-4-(4-(1-imidazolylcarbonyloxy)phenyl)hexane, Erythro 3-(3-(5,5-bis(dipivaloyloxymethoxyphosphinoyl) valerylamino)-4-benzoyloxyphenyl)-4-(4-benzoyloxyphenyl)hexane, Erythro 3-(3-(5,5-diphosphonovalerylamino)-4-hydroxyphenyl)-4-(4-hydroxyphenyl)hexane, Erythro 3-(3-(4,4-diphosphono-4-hydroxybutyrylamino)-4-hydroxyphenyl)-4-(4-hydroxyphenyl)hexane, Erythro 3-(3-(5,5-diphosphono-5-hydroxyvalerylamino)-4-hydroxyphenyl)-4-(4-hydroxyphenyl)hexane, Erythro 3-(3-(5,5-bis(dipivaloyloxymethoxyphosphinoyl)-5-hydroxyvalerylamino)-4-hexanoyloxyphenyl)-4-(4-hexanoyloxyphenyl)hexane, Erythro 3-(3-(N-(3,3-diphosphono-3-hydroxypropyl)-N-methylglycylamino)-4-hydroxyphenyl)-4-(4-hydroxyphenyl)hexane, Erythro 3-(3-((3-diphosphonomethylamino-3,3-dimethylpropionyl)amino)-4-hydroxyphenyl)-4-(4-hydroxyphenyl)hexane, Erythro 3-(3-(3-diphosphonomethylaminopropionylamino)-4-hydroxyphenyl)-4-(4-hydroxyphenyl)hexane, Erythro 3-(3-((2,2-diphosphonoethoxy)acetylamino)-4-hydroxyphenyl)-4-(4-hydroxyphenyl)hexane, Erythro 3-(3-(N-(3,3-diphosphonopropyl)-N-methyl) aminocarbonylamino-4-hydroxyphenyl)-4-(4-hydroxyphenyl)hexane, Erythro 3-(3-(2,2-diphosphonoethyl) aminocarbonylamino-4-hydroxyphenyl)-4-(4-hydroxyphenyl)hexane, Erythro 3-(3-(3,3-diphosphonopropylsulfonylamino)-4-hydroxyphenyl)-4-(4-hydroxyphenyl)hexane, Erythro 3-(4-acetoxy-2-methylphenyl)-4-(4-acetoxy-3-(3,3-diphosphonopropylsulfonylamino)-2-methylphenyl) hexane, Erythro 3-(3-(4,4-diphosphonobutylsulfonylamino)-4-hydroxyphenyl)-4-(4-hydroxyphenyl)hexane, Erythro 3-(3-(4,4-diphosphonobutylsulfonylamino)-4-oleoyloxyphenyl)-4-(4-oleoyloxyphenyl)hexane, Erythro 3-(3-(3,3-bis(dipivaloyloxymethoxyphosphinoyl) propylsulfonylamino)-4-hydroxyphenyl)-4-(4-hydroxyphenyl)hexane, Erythro 3-(3-(4,4-bis(phosphonocarbonylmethyl) butyrylamino)-4-pivaloyloxyphenyl)-4-(4-pivaloyloxyphenyl)hexane, Erythro 3-(3-(3,3-bis(phosphonocarbonyl) propionylamino)-4-hydroxyphenyl)-4-(4-hydroxyphenyl) hexane, Erythro 3-(3-(4,4-bis(phosphonocarbonyl)butyrylamino)-4-hydroxyphenyl)-4-(4-hydroxyphenyl)hexane, Erythro 3-(3-(3,3-bis(phosphonocarbonylmethyl) propionylamino)-4-hydroxyphenyl)-4-(4-hydroxyphenyl) hexane, Erythro 3-(3-(N,N-bis(phosphonomethyl)glycylamino)-4-hydroxyphenyl)-4-(4-hydroxyphenyl)hexane, Erythro 3-(3-(3,3-dicarboxy-3-hydroxypropionylamino)-4-hydroxyphenyl)-4-(4-hydroxyphenyl)hexane, Erythro 4-(2,4-dihydroxyphenyl)-3-(2,4-dihydroxy-3-(4,4-diphosphonobutyrylamino)phenyl)hexane, (E)-3-(3-(4,4-Diphosphonobutyrylamino)-4-hydroxyphenyl)-4-(4-hydroxyphenyl)-3-hexene, (E)-3-(4-Crotonoyloxy-3-(4,4-diphosphonobutyrylamino)phenyl)-4-(4-crotonoyloxyphenyl)-3-hexene, (E)-3-(3-(3,3-Diphosphonopropionylamino)-4-p-toluoyloxyphenyl)-4-(4-p-toluoyloxyphenyl)-3-hexene, 1-Ethyl-5-(4,4-diphosphonobutyrylamino)-6-hydroxy-2-(4-hydroxyphenyl)-3-methylindole, 1,3-Diethyl-6-(4,4-diphosphonobutyrylamino)-5-hydroxy-2-(4-hydroxyphenyl)indole, 1-Ethyl-5-(5,5-diphosphono-5-hydroxyvalerylamino)-6-hydroxy-2-(4-hydroxyphenyl)-3-methylindole, 1-Ethyl-5-(N-diphosphonomethylglycyl)amino-6-hydroxy-2-(4-hydroxyphenyl)-3-methylindole, 5-(4,4-Bis(dipivaloyloxymethoxyphosphinoyl) butyrylamino)-1-ethyl-6-hexanoyloxy-2-(4-hexanoyloxyphenyl)-3-methylindole, 5-(4,4-Bis(dipivaloyloxymethoxyphosphinoyl)butyrylamino)-1-ethyl-6-heptanoyloxy-2-(4-heptanoyloxyphenyl)-3-methylindole, 5-(4,4-Diphosphono-4-hydroxybutyrylamino)-1-ethyl-3-methyl-2-(4-stearoyloxyphenyl)-6-stearoyloxyindole, 5-(N-(2,2-Diphosphonoethyl)glycylamino)-1-ethyl-6-hexanoyloxy-2-(4-(1-imidazolylcarbonyloxy)phenyl)-3-methylindole, 6-(1-Carboxy-2-phenylethyl)aminocarbonyloxy-2-(4-(1-carboxy-2-phenylethyl)aminocarbonyloxyphenyl)-5-(4,4-diphosphonobutyrylamino)-1-ethyl-3-methylindole, 5-(4,4-Bis(dipivaloyloxymethoxyphosphinoyl) butyrylamino)-6-(N,N-dihexylamino)carbonyloxy-2-(4-(N,N-dihexylamino)carbonyloxyphenyl)-1-ethyl-3-methylindole, 5-(4,4-Bis(dipivaloyloxymethoxyphosphinoyl) butyrylamino)-1-ethyl-2-(4-N-p-ethoxyphenyl-N-methylamino)carbonyloxyphenyl-6-hydroxy-3-methylindole, 1,3-Diethyl-6-(4,4-diphosphonobutyrylamino)-2-(4-saccharinylmethyloxyphenyl)-5-saccharinylmethyloxyindole, 5-(4,4-Diphosphonovalerylamino)-1-ethyl-2-(4-oleoyloxyphenyl)-6-oleoyloxy-3-(2,2,2-trifluoroethyl) indole, 5-(4,4-Diphosphonobutyrylamino)-1-ethyl-3-isopropyl-2-(4-pivaloyloxyphenyl)-6-pivaloyloxyindole, 3,4-Dihydro-7-(4,4-diphosphonobutyrylamino)-6-hydroxy-2-(4-hydroxyphenyl)-1-phenylnaphthalene, 5-(4,4-Diphosphonobutyrylamino)-3-ethyl-6-hydroxy-2-(4-hydroxyphenyl)-1-methylindene, 6-(4,4-Diphosphonobutyrylamino)-3-ethyl-5-hydroxy-2-(4-hydroxyphenyl)benzo[b]thiophene, 6-(4,4-Diphosphonobutyrylamino)-4-ethyl-3-(4-hydroxyphenyl)-2-methyl-2H-1-benzopyran-7-ol, 6-(4,4-Bis(dipivaloyloxymethoxyphosphinoyl) butyrylamino)-4-ethyl-3-(4-hexanoyloxyphenyl)-2-methyl-2H-1-benzopyran-7-ol, 6-(4,4-Diphosphonobutyrylamino)-3-(4-hydroxyphenyl)-4-phenyl-2H-1-benzopyran-7-ol, 6-(4,4-Diphosphonobutyrylamino)-7-hydroxy-3-(4-hydroxyphenyl)-4-n-propyl-2H-1-benzopyran-2-one, The present invention is more concretely illustrated below with reference to examples and reference examples but is, of course, not limited by them. The abbreviations used in the following examples and reference examples have the following meanings:

Bn: benzyl group,
Et: ethyl group,
i-Pr: isopropyl group,
Me: methyl group,
MOM: methoxymethyl group,
PNB: p-nitrobenzyl group,
TBS: t-butyldimethylsilyl group,
TMS: trimethylsilyl group,
Tr: triphenylmethyl group,
br.: broad,
sh.: shoulder.

EXAMPLE 1

Erythro 3-(3-(4,4-bis(diisopropoxyphosphinoyl)butyrylamino)-4-t-butyldimethylsilyloxyphenyl)-4-(4-t-butyldimethylsilyloxyphenyl)hexane

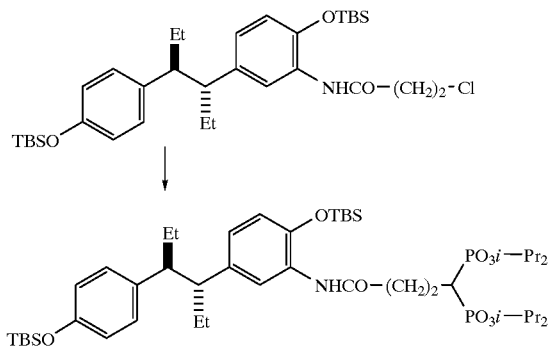

In a nitrogen stream, 60% sodium hydride (26 mg) was suspended in toluene (1 ml), and tetraisopropyl methylenebisphosphonate (277 mg) was added dropwise thereto. The resulting mixture was stirred at room temperature for 10 minutes, followed by adding thereto a solution in toluene of the erythro 3-(3-(3-chloropropionylamino)-4-t-butyldimethylsilyloxyphenyl)-4-(4-t-butyldimethylsilyloxyphenyl)hexane (200 mg) obtained by the process described in Reference Example 2, and the mixture thus obtained was stirred with heating at 100° C. for 1 hour. Water was added thereto, followed by extraction with ethyl acetate, and the organic layer was washed with a saturated aqueous sodium chloride solution, dried over anhydrous magnesium sulfate and then concentrated under reduced pressure. The residue was collected and then purified by a thin-layer chromatography (methanol:chloroform=3:97) to obtain erythro 3-(3-(4,4-bis(diisopropoxyphosphinoyl)butyrylamino)-4-t-butyldimethylsilyloxyphenyl)-4-(4-t-butyldimethylsilyloxyphenyl)hexane (155 mg, yield 55%).

$^1$H-NMR (CDCl$_3$) δ: ppm; 0.20 (6H, s), 0.28 (6H, s), 0.50 (3H, t, J=7.3 Hz), 0.51 (3H, t, J=7.3 Hz), 0.99 (9H, s), 1.04 (9H, s), 1.1–1.5 (28H, m), 2.2–2.6 (5H, m), 2.7–2.8 (2H, m), 4.7–4.9 (4H, m), 6.6–6.8 (4H, m), 7.00 (2H, d, J=8.6 Hz), 7.75 (1H, s), 8.25 (1H, d, J=2.0 Hz).

EXAMPLE 2

Erythro 3-(3-(4,4-bis(diisopropoxyphosphinoyl)butyrylamino)-4-hydroxyphenyl-4-(4-hydroxyphenyl hexane

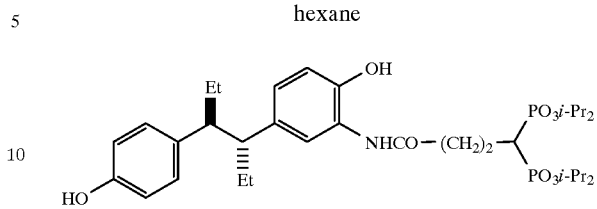

Under a nitrogen atmosphere, erythro 3-(3-(4,4-bis(diisopropoxyphosphinoyl)butyrylamino)-4-t-butyldimethylsilyloxyphenyl)-4-(4-t-butyldimethylsilyloxyphenyl)hexane (1.43 g) obtained by the process described in Example 1 was dissolved in acetonitrile (5 ml), and a mixed solution of a 46% aqueous hydrofluoric acid solution (1 ml), water (9 ml) and acetonitrile (90 ml) was added thereto. After standing at room temperature for 2 days, the solvent was distilled off under reduced pressure and a saturated aqueous sodium hydrogencarbonate solution was added to the residue, followed by two runs of extraction with ethyl acetate. The organic layer was washed with a saturated aqueous sodium chloride solution, dried over anhydrous magnesium sulfate and then concentrated under reduced pressure. The residue was purified by a silica gel column chromatography (methanol:methylene chloride=0:100 to 3:97) to obtain erythro 3-(3-(4,4-bis(diisopropoxyphosphinoyl)butyrylamino)-4-hydroxyphenyl)-4-(4-hydroxyphenyl)hexane (0.833 g, yield 78%).

$^1$H-NMR (CDCl$_3$) δ: ppm; 0.50 (3H, t, J=7.3 Hz), 0.56 (3H, t, J=7.3 Hz), 1.1–1.5 (28H, m), 2.2–2.5 (5H, m), 2.83 (2t, t, J=6.9 Hz), 4.6–4.9 (4H, m), 6.68 (1H, s), 6.8–7.0 (6H, m), 8.16 (1H, s), 9.09 (1H, s), 9.25 (1H, s).

EXAMPLE 3

Erythro 3-(3-(4,4-diphosphonobutyrylamino)-4-hydroxyphenyl)-4-(4-hydroxyphenyl)hexane disodium salt

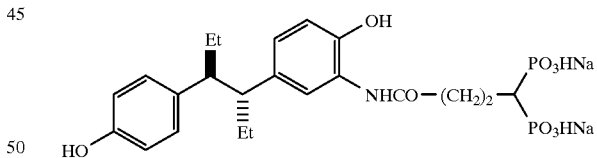

Under a nitrogen atmosphere, erythro 3-(3-(4,4-bis(diisopropoxyphosphinoyl)butyrylamino)-4-hydroxyphenyl)-4-(4-hydroxyphenyl)hexane (0.35 g) obtained by the process described in Example 2 was dissolved in acetonitrile (3 ml), followed by adding dropwise thereto bromotrimethylsilane (0.675 ml), and the resulting mixture was maintained at room temperature for 23 hours and then at 50–55° C. for 3 hours. The solvent and the like were distilled off under reduced pressure, and then water and sodium hydrogencarbonate (130 mg) were added to the residue and the resulting mixture was stirred at room temperature for 20 minutes. After purification by a column chromatography (eluent; acetonitrile:water=5:95 to 10:90) using Diaion CHP-20P gel (mfd. by Mitsubishi Kasei Corp.), the acetonitrile was distilled off under reduced pressure at 50° C. or lower and the residue was freeze-dry and then dried under reduced pressure at 60° C. to obtain erythro 3-(3-(4,4-diphosphonobutyrylamino)-4-hydroxyphenyl)-4-(4-hydroxyphenyl)hexane disodium salt (88 mg, yield 31%).

$^1$H-NMR (D$_2$O) δ: ppm; 0.3–0.5 (6H, m), 1.0–1.4 (4H, m), 1.6–1.9 (1H, m), 1.9–2.2 (2H, m), 2.3–2.5 (2H, m), 2.5–2.7 (2H, m), 6.75 (2H, d, J=8.3 Hz), 6.81 (1H, d, J=8.3 Hz), 6.94 (1H, dd, J=2.0 Hz and 8.3 Hz), 7.05 (2H, d, J=8.6 Hz), 7.11 (1H, d, J=1.7 Hz).

IR (KBr):cm$^{-1}$; 3263 (br.), 1641, 1614, 1546, 1515, 1454, 1252, 1158, 1123, 1076, 884, 835, 713.

EXAMPLE 4

Erythro 3-(3-(3,3-bis(diisopropoxyphosphinoyl)propionylamino)-4-methoxymethyoxyphenyl)-4-(4-methoxymethoxyphenyl)hexane

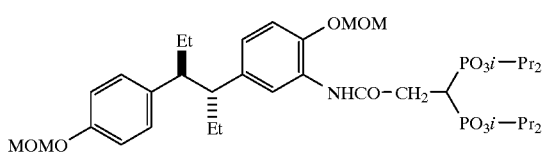

Under a nitrogen atmosphere, erythro 3-(3-amino-4-methoxymethoxyphenyl)-4-(4-methoxymethoxyphenyl)hexane (3.08 g) obtained by the process described in Reference Example 4, triethylamine (2.6 ml) and 3,3-bis(diisopropoxyphosphinoyl)propionic acid (3.2 g) were dissolved in dry methylene chloride (15 ml), and the resulting solution was cooled to 0–5° C. Bis(2-oxo-3-oxazolidinyl)phosphinyl chloride (2.02 g) was added thereto and the resulting mixture was slowly heated to room temperature and stirred overnight. Water was added to the reaction mixture to effect separation, and the organic layer was dried over anhydrous magnesium sulfate and concentrated under reduced pressure. The residue was purified by a silica gel column chromatography (methanol:methylene chloride=5:95 to 10:90) to obtain erythro 3-(3-(3,3-bis(diisopropoxyphosphinoyl)propionylamino)-4-methoxymethoxyphenyl)-4-(4-methoxymethoxyphenyl)hexane (4.92 g, yield 85%).

$^1$H-NMR (CDCl$_3$) δ: ppm; 0.46–0.52 (6H, m), 1.17–1.39 (28H, m), 2.44–2.52(2H, m), 2.89 (2H, dt, J=6.3 Hz and 15.8 Hz), 3.09–3.31 (1H, m), 3.51 (3H, s), 3.54 (3H, s), 4.72–4.90 (4H, m), 5.18 (2H, s), 5.24 (2H, s), 6.81 (1H, dd, J=2.1 Hz and 8.4 Hz), 6.96–7.01 (2H, m), 7.05–7.12 (3H, m), 7.98 (1H, s), 8.36 (1H, d, J=2.0 Hz).

EXAMPLE 5

Erythro 3-(3-(3,3-diphosphonopropionylamino)-4-hydroxyphenyl)-4-(4-hydroxyphenyl)hexane disodium salt

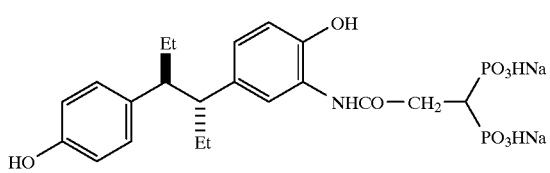

Erythro 3-(3-(3,3-diphosphonopropionylamino)-4-hydroxyphenyl)-4-(4-hydroxyphenyl)hexane disodium salt (2.6 g, yield 79%) was obtained in the same manner as in Example 3 except for using erythro 3-(3-(4,4-bis(diisopropoxyphosphinoyl)propionylamino)-4-methoxymethoxyphenyl)-4-(4-methoxymethoxyphenyl)hexane (4.92 g) obtained by the process described in Example 4.

$^1$H-NMR (D$_2$O) δ: ppm; 0.44 (3H, t, J=7.3 Hz), 0.45 (3H, t, J=7.1 Hz), 1.1–1.4 (4H, m), 2.3–2.6 (3H, m), 2.6–2.9 (2H, m), 6.7–7.1 (7H, m).

EXAMPLE 6

Erythro 3-(3-(4,4-bis(diethoxyphosphinoyl)butyrylamino)-4-methoxymethoxyphenyl)-4-(4-methoxymethoxyphenyl)hexane

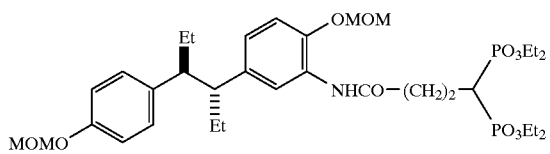

Erythro 3-(3-(4,4-bis(diethoxyphosphinoyl)butyrylamino)-4-methoxymethoxyphenyl)-4-(4-methoxymethoxyphenyl)hexane (7.48 g, yield 98%) was obtained in the same manner as in Example 4 except for using erythro 3-(3-amino-4-methoxymethoxyphenyl)-4-(4-methoxymethoxyphenyl)hexane (4.0 g) obtained by the process described in Reference Example 4 and 4,4-bis(diethoxyphosphinoyl)butyric acid (1 equivalent per equivalent of the former) obtained by the process described in Reference Example $^1$H-NMR (CDCl$_3$) δ: ppm; 0.51 (3H, t, J=7.3 Hz), 0.52 (3H, t, J=7.3 Hz), 1.22–1.39 (16H, m), 2.27–2.67 (5H, m), 2.82 (2H, t, J=7.6 Hz), 3.51 (3H, s), 3.53 (3H, s), 4.15–4.27 (8H, m), 5.18 (2H, s), 5.22 (2H, s), 6.81 (1H, dd, J=2.0 and 8.3 Hz), 6.97–7.11 (5H, m), 7.98 (1H, s), 8.27 (1H, s).

EXAMPLE 7

Erythro 3-(3-(4,4-bis(diethoxyphosphinoyl)butyrylamino)-4-hydroxyphenyl)-4-(4-hydroxyphenyl)hexane

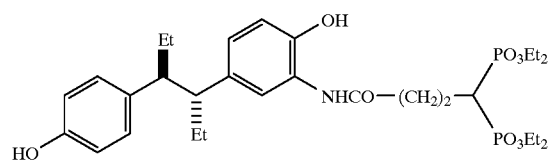

Under a nitrogen atmosphere, Erythro 3-(3-(4,4-bis(diethoxyphosphinoyl)butyrylamino)-4-methoxymethoxyphenyl)-4-(4-methoxymethoxyphenyl)hexane (7.48 g) obtained by the process described in Example 6 was dissolved in methanol (160 ml), and the solution was cooled to 0–5° C. After 6N hydrochloric acid (16 ml) was added thereto, the resulting mixture was slowly heated to room temperature and stirred overnight. Chloroform and a saturated aqueous sodium chloride solution were added to the reaction mixture, and the reaction product was extracted three times, and then the extract solution was dried over anhydrous magnesium sulfate and concentrated under reduced pressure. The residue was purified by a silica gel column chromatography (acetone:chloroform=0:100 to 50:50) to obtain erythro 3-(3-(4,4-bis(diethoxyphosphinoyl)butyrylamino)-4-hydroxyphenyl)-4-(4-hydroxyphenyl)hexane (5.20 g, yield 77%).

$^1$H-NMR (CDCl$_3$) δ: ppm; 0.54 (3H, t, J=7.3 Hz), 0.58 (3H, t, J=7.3 Hz), 1.1–1.6 (16H, m), 2.2–2.7 (5H, m), 2.82 (2H, t, J=6.9 Hz), 4.1–4.3 (8H, m), 6.59 (1H, d, J=1.3 Hz), 6.84 (2H, d, J=8.6 Hz), 6.9–7.0 (4H, m), 7.83 (1H, s), 8.96 (1H, s), 9.15 (1H, s).

EXAMPLE 8

Erythro 3-(3-(4,4-diphosphonobutyrylamino)-4-hydroxyphenyl)-4-(4-hydroxyphenyl)hexane disodium salt

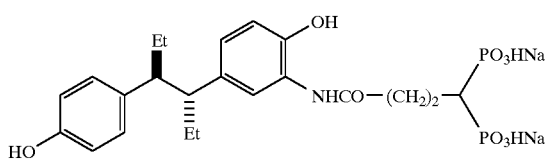

Under a nitrogen atmosphere, erythro 3-(3-(4,4-bis(diethoxyphosphinoyl)butyrylamino)-4-hydroxyphenyl)-4-(4-hydroxyphenyl)hexane (4.02 g) obtained by the process described in Example 7 was dissolved in acetonitrile (42 ml), followed by adding dropwise thereto bromotrimethylsilane (9.4 ml). Thereafter, erythro 3-(3-(4,4-diphosphonobutyrylamino)-4-hydroxyphenyl)-4-(4-hydroxyphenyl)hexane disodium salt (2.62 g, yield 73%) was obtained in the same manner as in Example 3 except for carrying out purification by a column chromatography using Diaion HP-21 gel (mfd. by Mitsubishi Kasei Corp.). Its spectrum data were the same as those obtained in Example 3.

EXAMPLE 9

Erythro 3-(3-(5,5-bis(diisopropoxyphosphinoyl)valerylamino)-4-methoxymethoxyphenyl)-4-(4-methoxymethoxyphenl)hexane

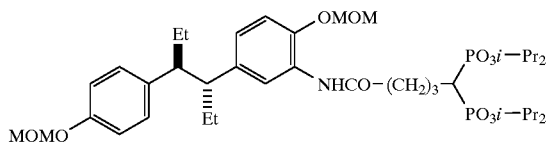

Under a nitrogen atmosphere, erythro 3-(3-amino-4-methoxymethoxyphenyl)-4-(4-methoxymethoxyphenyl)hexane (989 mg) obtained by the process described in Reference Example 4, triethylamine (0.846 ml) and the 5,5-bis(diisopropoxyphosphinoyl)valeric acid (1.0 g) obtained in Reference Example 7 were dissolved in dry methylene chloride (14 ml), and the resulting solution was cooled to 0–5° C. Bis(2-oxo-3-oxazolidinyl)phosphinyl chloride (0.67 g) was added to the solution and thereafter erythro 3-(3-(5,5-bis(diisopropoxyphosphinoyl)valerylamino)-4-methoxymethoxyphenyl)- 4-(4-methoxymethoxyphenyl)hexane (1.51 g, yield 73%) was obtained in the same manner as in Example 4.

$^1$H-NMR (CDCl$_3$) δ: ppm; 0.4–0.6 (6H, m), 1.2–1.4 (28H, m), 1.9–2.15 (4H, m), 2.15–2.6 (5H, m), 3.51 (3H, s), 3.53 (3H, s), 4.7–4.9 (4H, m), 5.18 (2H, s), 5.23 (2H, s), 6.75–7.15 (6H, m), 7.88 (1H, s), 8.31 (1H, s).

EXAMPLE 10

Erythro 3-(3-(5,5-diphosphonovalerylamino)-4-hydroxyphenyl)-4-(4-hydroxyphenyl)hexane disodium salt

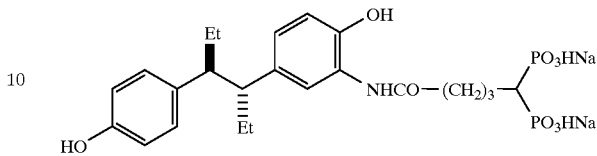

Erythro 3-(3-(5,5-diphosphonovalerylamino)-4-hydroxyphenyl)-4-(4-hydroxyphenyl)hexane disodium salt (0.63 g, yield 59%) was obtained in the same manner as in Example 3 except for using erythro 3-(3-(5,5-bis(diisopropoxyphosphinoyl)valerylamino)-4-methoxymethoxyphenyl-4-(4-methoxymethoxyphenyl)hexane (1.46 g) obtained by the process described in Example 9.

$^1$H-NMR (D$_2$O) δ: ppm; 0.43 (6H, t, J=7.3 Hz), 1.1–1.4 (4H, m), 1.6–1.9 (5H, m), 2.3–2.5 (4H, m), 6.74 (2H, d, J=8.6 Hz), 6.79 (1H, d, J=8.3 Hz), 6.88 (1H, br.d, J=8.6 Hz), 7.02 (2H, d, J=8.6 Hz), 7.08 (1H, br.s).

EXAMPLE 11

Erythro 3-(3-(6,6-bis(diisopropoxyphosphinoyl)hexanoylamino)-4-methoxymethoxyphenyl)-4-(4-methoxymethoxyphenyl)hexane

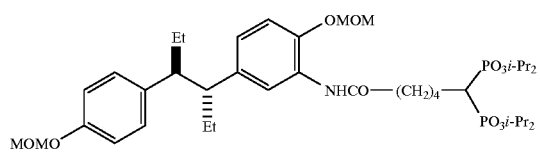

Erythro 3-(3-(6,6-bis(diisopropoxyphosphinoyl)hexanoylamino)-4-methoxymethoxyphenyl)-4-(4-methoxymethoxyphenyl)hexane (1.32 g, yield 63%) was obtained in the same manner as in Example 4 except for using erythro 3-(3-amino-4-methoxymethoxyphenyl)-4-(4-methoxymethoxyphenyl)hexane (1.0 g) obtained by the process described in Reference Example 4 and 6,6-bis(diisopropoxyphosphinoyl)hexanoic acid (1 equivalent per equivalent of the former) obtained by the process described in Reference Example 12.

$^1$H-NMR (CDCl$_3$) δ: ppm; 0.51 (3H, t, J=7.4 Hz), 0.52 (3H, t, J=7.3 Hz), 1.2–1.5 (28H, m), 1.55–2.3 (7H, m), 2.4–2.6 (4H, m), 3.51 (3H, s), 3.53 (3H, s), 4.7–4.9 (4H, m), 5.18 (2H, s), 5.24 (2H, s), 6.80 (1H, dd, J=2.0 Hz and 8.6 Hz), 6.9–7.15 (5H, m), 7.81 (1H, s), 8.31 (1H, d, J=2.0 Hz).

EXAMPLE 12

Erythro 3-(3-(6,6-diphosphonohexanoylamino)-4-hydroxyphenyl)-4-(4-hydroxyphenyl)hexane disodium salt

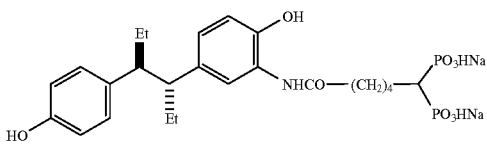

Erythro 3-(3-(6,6-diphosphonohexanoylamino)-4-hydroxyphenyl)-4-(4-hydroxyphenyl)hexane disodium salt (0.475 g, yield 49%) was obtained in the same manner as in Example 5 except for using erythro 3-(3-(6,6-bis(diisopropoxyphosphinoyl)hexanoylamino)-4-methoxymethoxyphenyl)-4-(4-methoxymethoxyphenyl)hexane (1.32 g) obtained by the process described in Example 11.

$^1$H-NMR (D$_2$O) δ: ppm; 0.2–0.4 (6H, m), 0.9–1.3 (4H, m), 1.4–1.9 (7H, m), 2.2–2.4 (4H, m), 6.6–6.9 (6H, m), 7.06 (1H, s).

EXAMPLE 13

Erythro 3-(3-(4,4-bis(dimethoxyphosphinoyl)-4-trimethylsilyloxybutyrylamino)-4-methoxymethoxyphenyl)-4-(4-methoxymethoxyphenyl)hexane

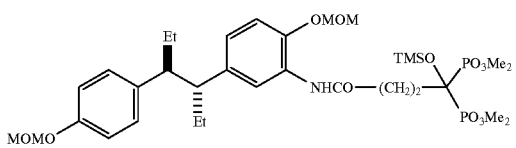

Erythro 3-(3-(4,4-bis(dimethoxyphosphinoyl)-4-trimethylsilyloxybutyrylamino)-4-methoxymethoxyphenyl)-4-(4-methoxymethoxyphenyl)hexane (778 mg, yield 69%) was obtained in the same manner as in Example 4 except for using erythro 3-(3-amino-4-methoxymethoxyphenyl)-4-(4-methoxymethoxyphenyl)hexane (560 mg) obtained by the process described in Reference Example 4 and 4,4-bis(dimethoxyphosphinoyl)-4-trimethylsilyloxybutyric acid (1 equivalent per equivalent of the former) obtained by the process described in Reference Example 15.

$^1$H-NMR (CDCl$_3$) δ: ppm; 0.27 (9H, s), 0.50 (3H, t, J=7.3 Hz), 0.51 (3H, t, J=7.3 Hz), 1.2–1.5 (4H, m), 2.4–2.9 (6H, m), 3.51 (3H, s), 3.54 (3H, s), 3.8–4.0 (12H, m), 5.18 (2H, s), 5.24 (2H, s), 6.80 (1H, dd, J=2.0 Hz and 8.3 Hz), 6.90–7.05 (2H, m), 7.05–7.15 (3H, m), 7.92 (1H, br.s), 8.30 (1H, d, J=2.0 Hz).

EXAMPLE 14

Erythro 3-(3-(4,4-diphosphono-4-hydroxybutyrylamino)-4-hydroxyphenyl)-4-(4-hydroxyphenyl hexane

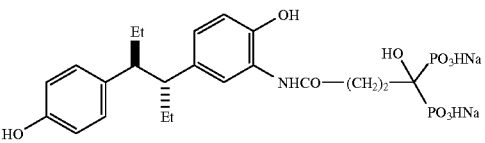

Under a nitrogen atmosphere, erythro 3-(3-(4,4-bis(dimethoxyphosphinoyl)-4-trimethylsilyloxybutyrylamino)-4-methoxymethoxyphenyl)-4-(4-methoxymethoxyphenyl)hexane (708 mg) obtained by the process described in Example 13 was dissolved in dry methylene chloride (9.5 ml), followed by adding dropwise thereto bromotrimethylsilane (2.33 g). Thereafter erythro 3-(3-(4,4-diphosphono-4-hydroxybutyrylamino)-4-hydroxyphenyl)-4-(4-hydroxyphenyl)hexane disodium salt (56 mg, yield 15 10%) was obtained in the same manner as in Example 8.

$^1$H-NMR (D$_2$O) δ: ppm; 0.47 (6H, br.t, J=7.1 Hz), 1.1–1.5 (4H, m), 2.1–3.0 (6H, m), 6.80 (2H, d, J=8.3 Hz), 6.87 (1H, d, J=8.3 Hz), 7.0–7.1 (1H, m), 7.1–7.2 (3H, m).

EXAMPLE 15

Erythro 3-(3-(4,4-bis(diisopropoxyphosphinoyl) butyrylamino)-4-dimethylcarbamoyloxyphenyl)-4-(4-dimethylcarbamoyloxyphenyl)hexane

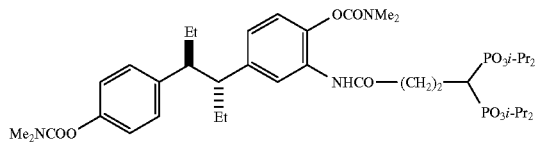

Erythro 3-(3-(4,4-bis(diisopropoxyphosphinoyl) butyrylamino)-4-dimethylcarbamoyloxyphenyl)-4-(4-dimethylcarbamoyloxyphenyl)hexane (1.79 g, yield 79%) was obtained in the same manner as in Example 4 except for using erythro 3-(3-amino-4-dimethylcarbamoyloxyphenyl)-4-(4-dimethylcarbamoyloxyphenyl)hexane (1.17 g) obtained by the process described in Reference Example 17 and 4,4-bis(diisopropoxyphosphinoyl)butyric acid (1 equivalent per equivalent of the former) obtained by the process described in Reference Example 8, in a nitrogen stream.

$^1$H-NMR (CDCl$_3$) δ: ppm; 0.52 (3H, t, J=7.1 Hz), 0.53 (3H, t, J=7.1 Hz), 1.2–1.5 (28H, m), 2.2–2.5 (3H, m), 2.5–2.65 (2H, m), 2.76 (2H, t, J=7.3 Hz), 3.02 (3H, s), 3.04 (3H, s), 3.10 (3H, s), 3.16 (3H, s), 4.7–4.9 (4H, in), 6.85–7.25 (6H, m), 8.04 (1H, s), 8.09 (1H, s).

IR (neat): cm$^{-1}$; 3440 (br.), 3330 (br.), 1733, 1725 (sh.), 1384, 1220, 1178, 990, 730.

EXAMPLE 16

Erythro 3-(3-(4,4-diphosphonobutyrylamino)-4-dimethylcarbamoyloxyphenyl)-4-(4-dimethylcarbamoyloxyphenyl)hexane disodium salt

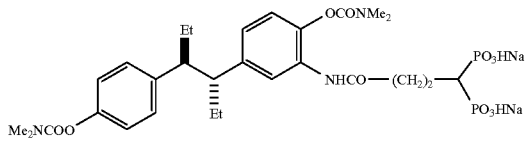

Erythro 3-(3-(4,4-diphosphonobutyrylamino)-4-dimethylcarbamoyloxyphenyl)-4-(4-dimethylcarbamoyloxyphenyl)hexane disodium salt (547 mg, yield 53%) was obtained in the same manner as in Example 3 except for using erythro 3-(3-(4,4-bis(diisopropoxyphosphinoyl)butyrylamino)-4-dimethylcarbamoyloxyphenyl)-4-(4-dimethylcarbamoyloxyphenyl)hexane (1.22 g) obtained by the process described in Example 15.

$^1$H-NMR ($D_2O$) δ: ppm; 0.3–0.5 (6H, m), 1.1–1.4 (4H, m), 1.6–1.9 (1H, m), 1.9–2.2 (2H, m), 2.5–2.7 (4H, m), 2.88 (3H, s), 2.89 (3H, s), 3.02 (6H, s), 6.9–7.2 (7H, m).

IR (KBr): cm$^{-1}$; 3400 (br.), 1720, 1393, 1218, 1180.

EXAMPLE 17

Erythro 3-(3-(1-(2,2-diphosphonoethylamino)-1-cyclohexylcarbonylamino)-4-hydroxyphenyl)-4-(4-hydroxyphenyl)hexane trifluoroacetate Under a nitrogen atmosphere, erythro 3-(3-(1-amino-1-cyclohexylcarbonylamino)-4-hydroxyphenyl)-4-(4-hydroxyphenyl)hexane (373 mg) obtained by the process described in Reference Example 20 and tetraethyl ethenylidenebisphosphonate (271 mg) were dissolved in methanol (2 ml), and the resulting solution was stirred at 20° C. for 2 hours, at 40° C. for 4 hours, and then under reflux for 6 hours. The reaction solution was concentrated under reduced pressure and the residue was dissolved in acetonitrile (6.8 ml), followed by adding dropwise thereto trimethylsilyl bromide (1.2 ml). Thereafter, erythro 3-(3-(1-(2,2-diphosphonoethylamino)-1-cyclohexylcarbonylamino)-4-hydroxyphenyl)-4-(4-hydroxyphenyl)hexane trifluoroacetate (39 mg, yield 7%) was obtained in the same manner as in Example 3 except for carrying out purification by a high-performance reversed phase column chromatography (the mobile phase: acetonitrile diluted with a 0.1% aqueous trifluoroacetic acid solution).

$^1$H-NMR ($CD_3OD$) δ: ppm; 0.42 (3H, t, J=7.1 Hz), 0.43 (3H, t, J=7.3 Hz), 1.08–1.34 (4H, m), 1.44–2.36 (15H, m), 6.7–6.9 (4H, m), 7.11 (1H, d, J=2.0 Hz), 7.42 (1H, s), 7.73 (1H, s).

EXAMPLE 18

Erythro 3-(3-(4,4-bis(diethoxyphosphinoyl)-2-methylbutyrylamino)-4-methoxymethoxyphenyl)-4-(4-methoxymethoxyphenyl)hexane

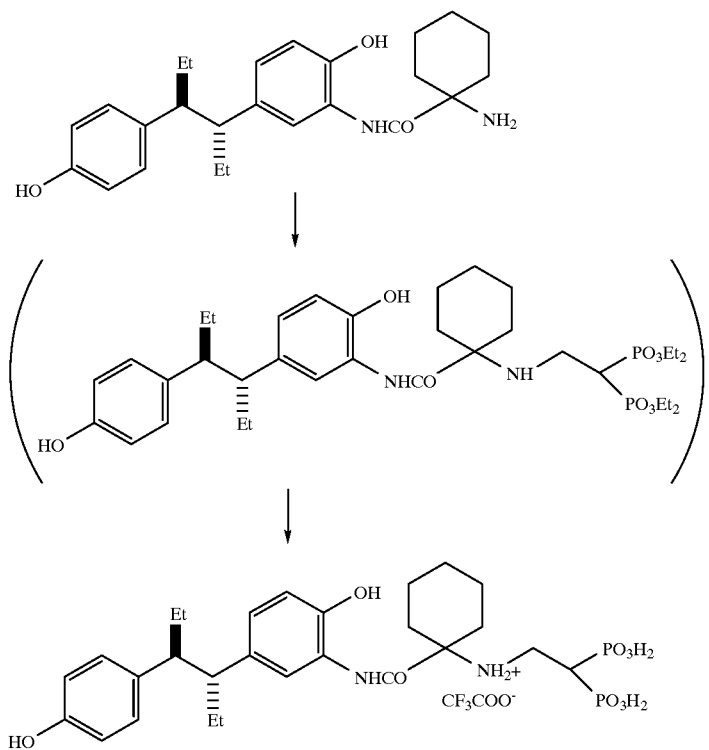

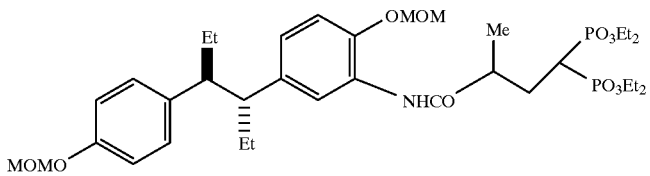

Erythro 3-(3-(4,4-bis(diethoxyphosphinoyl)-2-methylbutyrylamino)-4-methoxymethoxyphenyl)-4-(4-methoxymethoxyphenyl)hexane (0.98 g, yield 57%) was obtained in the same manner as in Example 4 except for using erythro 3-(3-amino-4-methoxymethoxyphenyl)-4-(4-methoxymethoxyphenyl)hexane (0.87 g) obtained by the process described in Reference Example 4 and 4,4-bis(diethoxyphosphinoyl)-2-methylbutyric acid (1 equivalent per equivalent of the former) obtained by the process described in Reference Example 23.

$^1$H-NMR (CDCl$_3$) δ: ppm; 0.51 (3H, t, J=7.3 Hz), 0.52 (3H, t, J=7.3 Hz), 1.25–1.39 (19H, m), 1.91–2.12 (1H, m), 2.22–2.67 (4H, m), 2.99–3.10 (1H, m), 3.51 (3H, s), 3.53 (3H, s), 4.1–4.3 (8H, m), 5.18 (2H, s), 5.22 (2H, s), 6.81 (1H, dd, J=2.0 Hz and 8.3 Hz), 6.9–7.15 (5H, m), 8.2–8.35 (2H, m).

IR (neat): cm$^{-1}$; 3427 (br.), 1688, 1596, 1531, 1510, 1480, 1434, 1154, 835, 805, 754.

EXAMPLE 19
Erythro 3-(3-(4,4-bis(diethoxyphosphinoyl)-2-methylbutyrylamino)-4-hydroxyphenyl)-4-(4-hydroxyphenyl)hexane

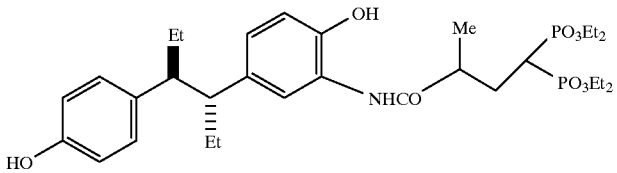

Erythro 3-(3-(4,4-bis(diethoxyphosphinoyl)-2-methylbutyrylamino)-4-hydroxyphenyl)-4-(4-hydroxyphenyl)hexane (0.66 g, yield 77%) was obtained in the same manner as in Example 7 except for using erythro 3-(3-(4,4-bis(diethoxyphosphinoyl)-2-methylbutyrylamino)-4-methoxymethoxyphenyl)-4-(4-methoxymethoxyphenyl)hexane (0.98 g) obtained by the process described in Example 18.

$^1$H-NMR (CDCl$_3$) δ: ppm; 0.5–0.7 (6H, m), 1.24–1.56 (21H, m), 1.9–2.6 (3H, m), 3.05–3.20 (1H, m), 4.0–4.3 (8H, m), 6.41 (1H, s), 6.70–7.02 (7H, m), 9.0–9.2 (2H, m).

EXAMPLE 20
Erythro 3-(3-(4,4-diphosphono-2-methylbutyrylamino-4-hydroxyphenyl)-4-(4-hydroxyphenyl)hexane disodium salt

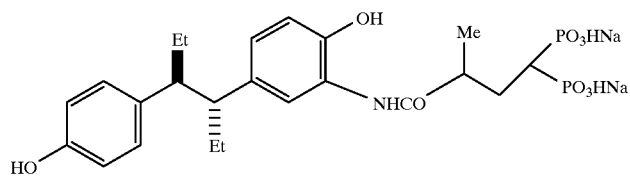

Erythro 3-(3-(4,4-diphosphono-2-methylbutyrylamino)-4-hydroxyphenyl)-4-(4-hydroxyphenyl)hexane disodium salt (169 mg, yield 29%) was obtained in the same manner as in Example 8 except for using erythro 3-(3-(4,4-bis(diethoxyphosphinoyl)-2-methylbutyrylamino)-4-hydroxyphenyl)-4-(4-hydroxyphenyl)hexane (0.66 g) obtained by the process described in Example 19.

$^1$H-NMR (D$_2$O) δ: ppm; 0.40–0.55 (6H, m), 1.12–1.45 (7H, m), 1.75–2.25 (3H, m), 2.46–2.59 (2H, m), 2.99–3.14 (1H, m), 6.77–7.56 (7H, m).

IR (KBr): cm$^{-1}$; 3208 (br.), 1652, 1615, 1515, 1173, 1082, 878.

EXAMPLE 21
Erythro 3-(3-(((bis(dimethoxyphosphinoyl)methylamino)carbonyl)acetylamino)-4-methoxymethoxyphenyl)-4-(4-methoxymethoxyphenyl)hexane

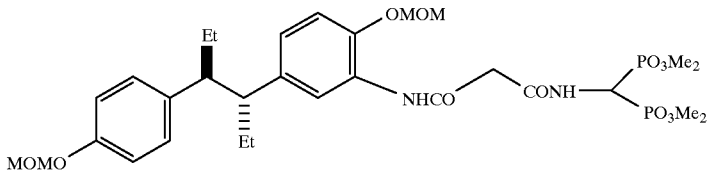

Erythro 3-(3-(((bis(dimethoxyphosphinoyl)methylamino)carbonyl)acetylamino)-4-methoxymethoxyphenyl)-4-(4-methoxymethoxyphenyl)hexane (0.14 g, yield 20%) was obtained in the same manner as in Example 4 except for using erythro 3-(3-carboxyacetylamino-4-methoxymethoxyphenyl)-4-(4-methoxymethoxyphenyl)hexane (0.46 g) obtained by the process described in Reference Example 25 and tetramethyl aminomethylenebisphosphonate (1 equivalent per equivalent of the former).

$^1$H-NMR (CDCl$_3$) δ: ppm; 0.51 (6H, t, J=7.3 Hz), 1.18–1.44 (4H, m), 2.43–2.54 (2H, m), 3.22 (1H, t, J=21.6 Hz), 3.50 (2H, s), 3.51 (3H, s), 3.55 (3H, s), 3.80–3.92 (12H, m), 5.18 (2H, s), 5.24 (2H, s), 6.85 (1H, dd, J=2.3 Hz and 8.4 Hz), 6.93–7.03 (2H, m), 7.03–7.14 (3H, m), 7.60–7.70 (1H, m), 8.23 (1H, d, J=1.7 Hz), 9.07 (1H, br.s).

EXAMPLE 22

Erythro 3-(3-(((bis(dimethoxyphosphinoyl)methylamino)carbonyl)acetylamino)-4-hydroxyphenyl)-4-(4-hydroxyphenyl)hexane

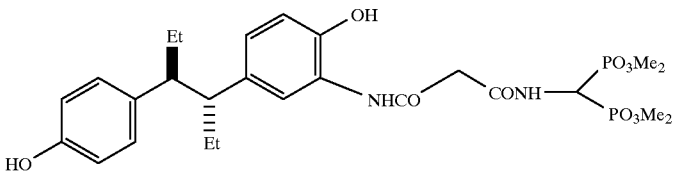

Erythro 3-(3-(((bis(dimethoxyphosphinoyl)methylamino)carbonyl)acetylamino)-4-hydroxyphenyl)-4-(4-hydroxyphenyl)hexane (0.16 g, yield 76%) was obtained in the same manner as in Example 7 except for using erythro 3-(3-(((bis(dimethoxyphosphinoyl)methylamino)carbonyl)acetylamino)-4-methoxymethoxyphenyl)-4-(4-methoxymethoxyphenyl)hexane (0.24 g) obtained by the process described in Example 21.

$^1$H-NMR (CDCl$_3$:CD$_3$OD=approximately 9:1) δ: ppm; 0.52 (6H, t, J=7.3 Hz), 1.17–1.47 (4H, m), 2.38–2.46 (2H, m), 3.51 (2H, s), 3.80–3.88 (12H, m), 5.16 (1H, t, J=22.4 Hz), 6.74–7.01 (6H, m), 7.34 (1H, br.s).

EXAMPLE 23

Erythro 3-(3-(((diphosphonomethylamino)carbonyl)acetylamino)-4-hydroxyphenyl)-4-(4-hydroxyphenyl)hexane disodium salt Erythro 3-(3-(((diphosphonomethylamino)carbonyl)acetylamino)-4-hydroxyphenyl)-4-(4-hydroxyphenyl)hexane disodium salt (73 mg, yield 46%) was obtained in the same manner as in Example 8 except for using erythro 3-(3-(((bis(dimethoxyphosphinoyl)methylamino)carbonyl)acetylamino)-4-hydroxyphenyl)-4-(4-hydroxyphenyl)hexane (0.16 g) obtained by the process described in Example 22.

$^1$H-NMR (D$_2$O) δ: ppm; 0.40 (3H, t, J=7.6 Hz), 0.42 (3H, t, J=7.3 Hz), 1.09–1.36 (4H, m), 1.87 (2H, s), 2.37–2.52 (2H, m), 4.18 (1H, t, J=18.8 Hz), 6.68–6.81 (3H, m), 6.87–6.94 (1H, m), 7.03 (2H, d, J=8.6 Hz), 7.21 (1H, d, J=2.0 Hz).

IR (KBr): cm$^{-1}$; 3378 (br.), 1664, 1627, 1365 (br.), 1120 (br.), 955, 834, 708.

EXAMPLE 24

Erythro 3-(3-((bis(dimethoxyphosphinoyl)methylamino)acetylamino)-4-methoxymethoxyphenyl)-4-(4-methoxymethoxyphenyl)hexane

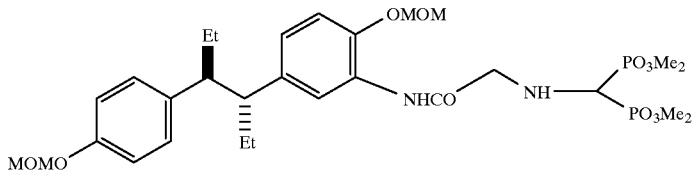

Under a nitrogen atmosphere, a solution in acetonitrile (17 ml) of erythro 3-(3-bromoacetylamino-4-methoxymethoxyphenyl)-4-(4-methoxymethoxyphenyl)hexane (0.82 g) obtained by the process described in Reference Example 26 was added dropwise to a solution of tetramethyl aminomethylenebisphosphonate (0.41 g) and diisopropylethylamine (0.28 ml) in acetonitrile (17 ml) under reflux over a period of 0.5 hour. After stirring under reflux for 4 hours, the reaction mixture was concentrated under reduced pressure and the residue was purified by a silica gel column chromatography (n-hexane:ethyl acetate =2:1 and then methylene chloride methanol =20:1) to obtain erythro 3-(3-((bis(dimethoxyphosphinoyl)methylamino)acetylamino)-4-methoxymethoxyphenyl)-4-(4-methoxymethoxyphenyl)hexane (0.156 g, yield 14%) (containing diisopropylethylamine as an impurity).

$^1$H-NMR (CDCl$_3$) δ: ppm; 0.51 (3H, t, J=7.3 Hz), 0.52 (3H, t, J=7.3 Hz), 1.18–1.45 (4H, m), 2.44–2.54 (2H, m), 3.43 (1H, t, J=21.4 Hz), 3.51 (3H, s), 3.53 (3H, s), 3.71 (2H, s), 3.84–3.92 (12H, m), 5.18 (2H, s), 5.23 (2H, s), 6.84 (1H, dd, J=2.1 Hz and 8.4 Hz), 6.95–7.02 (2H, m), 7.04–7.13 (3H, m), 8.26 (1H, d, J=2.0 Hz), 9.32 (1H, s).

EXAMPLE 25

Erythro 3-(3-((diphosphonomethylamino)acetylamino)-4-hydroxyphenyl)-4-(4-hydroxyphenyl hexane monosodium.monodiisopropylethylamine salt

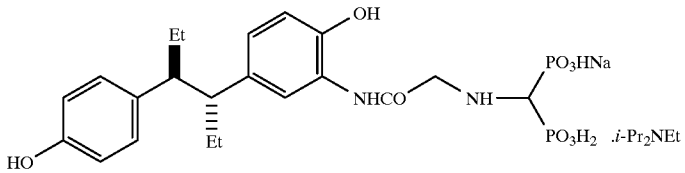

Erythro 3-(3-((diphosphonomethylamino)acetylamino)-4-hydroxyphenyl)-4-(4-hydroxyphenyl)hexane monosodium.monodiisopropylethylamine salt (71 mg, yield 18%) was obtained in the same manner as in Example 5 except for using erythro 3-(3-((bis(dimethoxyphosphinoyl)methylamino)acetylamino)-4-methoxymethoxyphenyl)-4-(4-methoxymethoxyphenyl)hexane (0.4 g) (containing diisopropylethylamine as an impurity) obtained by the process described in Example 24.

$^1$H-NMR (D$_2$O) δ: ppm (except for signals due to diisopropylethylamine) 0.30–0.49 (6H, m), 2.34–2.54 (2H, m), 6.65–7.39 (7H, m).

IR (KBr): cm$^{-1}$; 3357 (br.), 1677, 1612, 1514, 897, 834.

EXAMPLE 26

Erythro 3-(3-((3,3-bis(dimethoxyphosphinoyl)-3-hydroxypropylamino)carbonylamino)-4-methoxymethoxyphenyl)-4-(4-methoxymethoxyphenyl)hexane

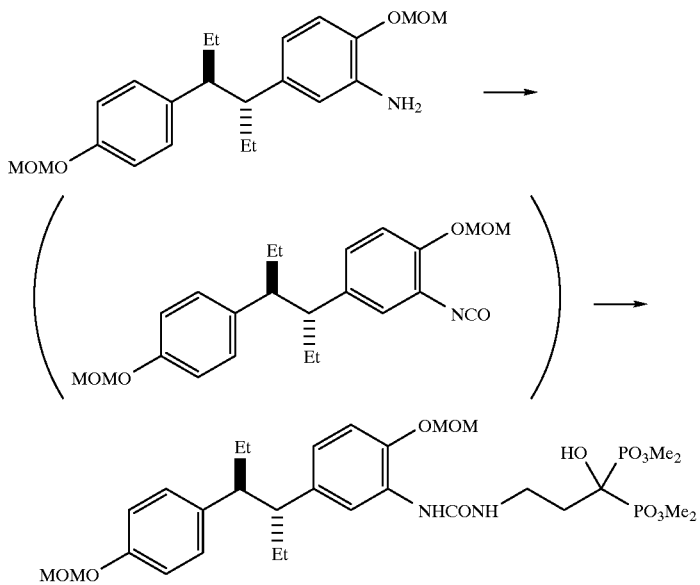

Under a nitrogen atmosphere, erythro 3-(3-amino-4-methoxymethoxyphenyl)-4-(4-methoxymethoxyphenyl)hexane (0.747 g) obtained by the process described in Reference Example 4, triphosgene (0.199 g) and triethylamine (0.202 g) were suspended in dry carbon tetrachloride (8 ml), and the resulting suspension was stirred at 70° C. for 2 hours. The reaction mixture was concentrated under reduced pressure and the residue was dissolved in dry methylene chloride (5 ml), and then the resulting solution was cooled to 0–5° C., followed by adding thereto a solution in dry methylene chloride (10 ml) of 3,3-bis(dimethoxyphosphinoyl)-3-hydroxypropylamine (2 mmol) obtained by the process described in Reference Example 28. Then, a solution of triethylamine (0.202 g) in dry methylene chloride (1 ml) was added thereto, and the resulting solution was heated to room temperature and allowed to stand overnight. The reaction solution was poured into ice water and extracted twice with ethyl acetate, and the organic layer was washed successively with diluted hydrochloric acid, a saturated aqueous sodium chloride solution, a saturated aqueous sodium hydrogencarbonate solution and a saturated aqueous sodium chloride solution, dried over anhydrous magnesium sulfate, and then concentrated under reduced pressure. The residue was purified by a silica gel column chromatography (chloroform:acetone=90:10 to 80:20) to obtain erythro 3-(3-((3,3-bis(dimethoxyphosphinoyl)-3-hydroxypropylamino)carbonylamino)-4-methoxymethoxyphenyl)-4-(4-methoxymethoxyphenyl)hexane (0.43 g, yield 31%).

$^1$H-NMR (CDCl$_3$) δ: ppm; 0.50 (3H, t, J=7.6 Hz), 0.53 (3H, t, J=6.9 Hz), 1.15–1.50 (4H, m), 1.90–2.15 (1H, m), 2.15–2.35 (1H, m), 2.40–2.60 (2H, m), 3.10–3.30 (1H, m), 3.51 (3H, s), 3.53 (3H, s), 3.70–4.00 (12H, m), 4.70–4.90 (1H, m), 5.18 (2H, s), 5.21 (2H, s), 5.97 (1H, m), 6.72 (1H, dd, J=2.0 Hz and 8.3 Hz), 6.90–7.15 (6H, m), 8.06 (1H, d, J=2.0 Hz).

IR (neat): cm$^{-1}$; 3350 (br.), 1670, 1599, 1550, 1510, 1155, 852, 750.

EXAMPLE 27

Erythro 3-(3-((3, 3-bis(dimethoxyphosphinoyl)-3-hydroxypropylamino)carbonylamino)-4-hydroxyphenyl)-4-(4-hydroxyphenyl)hexane

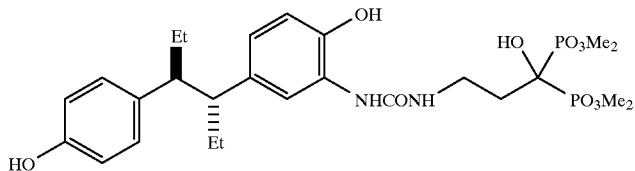

Erythro 3-(3-((3,3-bis(dimethoxyphosphinoyl)-3-hydroxypropylamino)carbonylamino)-4-hydroxyphenyl)-4-(4-hydroxyphenyl)hexane (0.35 g, yield 95%) was obtained in the same manner as in Example 7 except for using erythro 3-(3-((3,3-bis(dimethoxyphosphinoyl)-3-hydroxypropylamino)carbonylamino)-4-methoxymethoxyphenyl)-4-(4-methoxymethoxyphenyl)hexane (0.43 g) obtained by the process described in Example 26.

$^1$H-NMR (CDCl$_3$) δ: ppm; 0.54 (3H, t, J=7.6 Hz), 0.56 (3H, t, J=7.3 Hz), 1.10–1.55 (4H, m), 1.90–2.30 (2H, m), 2.30–2.50 (2H, m), 3.10–3.30 (1H, m), 3.70–4.00 (12H, m), 4.70–4.90 (1H, m), 6.16 (1H, br.s), 6.50 (1H, m), 6.75–7.15 (7H, m), 7.35 (1H, m), 9.70 (1H, m).

IR (neat): cm$^{-1}$; 3310 (br.), 1660, 1559, 1518, 858, 838, 750.

EXAMPLE 28

Erythro 3-(3-((3,3-diphosphono-3-hydroxypropylamino carbonylamino -4-hydroxyphenyl )-4-(4-hydroxyphenyl)hexane disodium salt

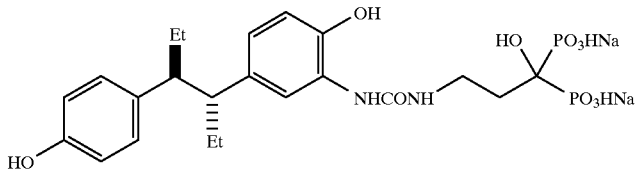

Erythro 3-(3-((3,3-diphosphono-3-hydroxypropylamino) carbonylamino)-4-hydroxyphenyl)-4-(4-hydroxyphenyl) hexane disodium salt (224 mg, yield 74%) was obtained in the same manner as in Example 8 except for using erythro 3-(3-((3,3-bis(dimethoxyphosphinoyl)-3-hydroxypropylamino)carbonylamino)-4-hydroxyphenyl)-4-(4-hydroxyphenyl)hexane (0.35 g) obtained by the process described in Example 27.

$^1$H-NMR (D$_2$O) δ: ppm; 0.41 (3H, t, J=7.3 Hz), 0.42 (3H, t, J=7.3 Hz), 1.06–1.41 (4H, m), 1.66–2.01 (2H, m), 2.36–2.51 (2H, m), 3.11–3.46 (2H, m), 6.66–6.91 (4H, m), 6.96–7.16 (3H, m).

IR (KBr): cm$^{-1}$; 3385 (br.), 1648, 1550, 1515, 907 (br.), 835.

EXAMPLE 29

Erythro 3-(3-(5,5-bis(dimethoxyphosphinoyl)-5-trimethylsilyloxyvalerylamino)-4-methoxymethoxyphenyl)-4-(4-methoxymethoxyphenyl)hexane

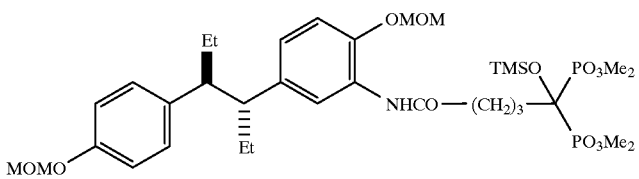

Erythro 3-(3-(5,5-bis(dimethoxyphosphinoyl)-5-trimethylsilyloxybutyrylamino)-4-methoxymethoxyphenyl)-4-(4-methoxymethoxyphenyl) hexane (1.17 g, quantitative yield) was obtained in the same manner as in Example 4 except for using erythro 3-(3-amino-4-methoxymethoxyphenyl)-4-(4-methoxymethoxyphenyl)hexane (560 mg) obtained by the process described in Reference Example 4 and 5,5-bis (dimethoxyphosphinoyl)-5-trimethylsilyloxyvaleric acid (1 equivalent per equivalent of the former) obtained by the process described in Reference Example 31.

$^1$H-NMR (CDCl$_3$) δ: ppm; 0.24 (9H, s), 0.51 (3H, t, J=7.3 Hz), 0.52 (3H, t, J=7.3 Hz), 1.14–1.46 (4H, m), 1.98–2.27 (4H, m), 2.43 (2H, t, J=7.3 Hz), 2.46–2.56 (2H, m), 3.51 (3H, s), 3.53 (3H, s), 3.79–3.91 (12H, m), 5.18 (2H, s), 5.23 (2H, s), 6.81 (1H, dd, J=2.0 Hz and 8.6 Hz), 6.94–7.02 (2H, m), 7.02–7.14 (3H, m), 7.83 (1H, br.s), 8.31 (1H, d, J=2.3 Hz).

EXAMPLE 30

Erythro 3-(3-(5,5-bis(dimethoxyphosphinoyl)-5-hydroxyvalerylamino)-4-hydroxyphenyl)-4-(4-hydroxyphenyl)hexane

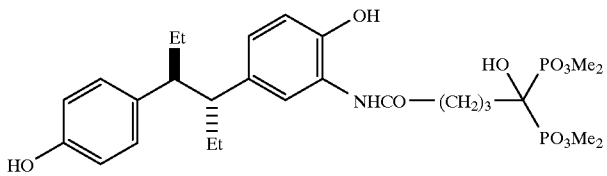

Erythro 3-(3-(5,5-bis(dimethoxyphosphinoyl)-5-hydroxyvalerylamino)-4-hydroxyphenyl)-4-(4-hydroxyphenyl)hexane (0.56 g, yield 61%) was obtained in the same manner as in Example 7 except for using erythro 3-(3-(5,5-bis(dimethoxyphosphinoyl)-5-trimethylsilyloxyvalerylamino)-4-methoxymethoxyphenyl)-4-(4-methoxymethoxyphenyl) hexane (1.17 g) obtained by the process described in Example 29.

$^1$H-NMR (CD$_3$OD) δ: ppm; 0.52 (3H, t, J=7.3 Hz), 0.53 (3H, t, J=7.4 Hz), 1.13–1.48 (4H, m), 1.95–2.23 (4H, m), 2.33–2.57 (4H, m), 3.81–3.91 (12H, m), 6.70–6.77 (2H, m), 6.79–6.85 (2H, m), 6.94–7.03 (2H, m), 7.46 (1H, s), 7.84–7.87 (1H, m).

EXAMPLE 31

Erythro 3-(3-(5,5-diphosphono-5-hydroxyvalerylamino)-4-hydroxyphenyl)-4-(4-hydroxyphenyl)hexane disodium salt

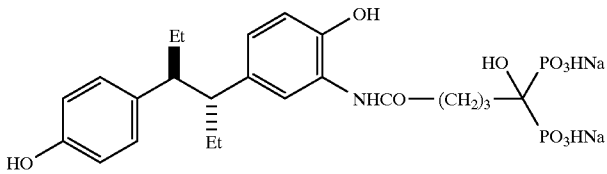

Erythro 3-(3-(5,5-diphosphono-5-hydroxyvalerylamino)-4-hydroxyphenyl)-4-(4-hydroxyphenyl)hexane disodium salt (206 mg, yield 38%) was obtained in the same manner as in Example 8 except for using erythro 3-(3-(5,5-bis(dimethoxyphosphinoyl)-5-hydroxyvalerylamino)-4-hydroxyphenyl)-4-(4-hydroxyphenyl)hexane (560 mg) obtained by the process described in Example 30.

$^1$H-NMR (D$_2$O) δ: ppm; 0.47 (6H, br.t, J=7.1 Hz), 1.10–1.44 (4H, m), 1.86–2.08 (4H, m), 2.36–2.58 (4H, m), 6.76–6.85 (2H, m), 6.89 (1H, d, J=8.6 Hz), 6.99 (1H, dd, J=2.0 Hz and 8.2 Hz), 7.03–7.12 (2H, m), 7.13 (1H, d, J=2.0 Hz).

IR (KBr): cm$^{-1}$; 3377 (br.), 1654, 1540, 1515, 1253, 835.

EXAMPLE 32

3-(3-(4,4-Bis(diethoxyphosphinoyl butyrylamino)-4-t-butyldimethylsilyloxyphenyl)-4-(4-t-butyldimethylsilyloxyphenyl)-3-hexene 3-(3-(4,4-Bis(diethoxyphosphinoyl)butyrylamino)-4-t-butyldimethylsilyloxyphenyl)-4-(4-t-butyldimethylsilyloxyphenyl)-3-hexene (0.79 g, yield 93%) was obtained in the same manner as in Example 4 except for using 3-(3-amino-4-t-butyldimethylsilyloxyphenyl)-4-(4-t-butyldimethylsilyloxyphenyl)-3-hexene (0.51 g) obtained by the process described in Reference Example 34.

$^1$H-NMR (CDCl$_3$) δ: ppm; 0.23 (6H, s), 0.30 (6H, s), 0.76 (3H, t, J=7.4 Hz), 0.77 (3H, t, J=7.4 Hz), 1.00 (9H, s), 1.05 (9H, s), 1.30–1.39 (12H, m), 2.06–2.19 (4H, m), 2.20–2.80 (5H, m), 4.12–4.27 (8H, m), 6.71–6.86 (4H, m), 6.98–7.07 (2H, m), 7.75 (1H, br.s), 8.21 (1H, d, J=2.0 Hz).

EXAMPLE 33

3-(3-(4,4-Bis(diethoxyphosphinoyl)butyrylamino)-4-hydroxyphenyl)-4-(4-hydroxyphenyl)-3-hexene

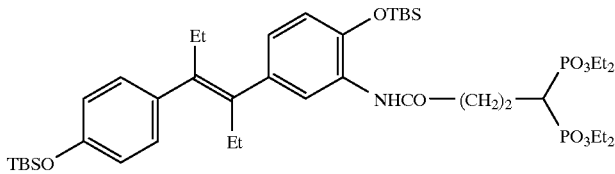

Under a nitrogen atmosphere, 3-(3-(4,4-bis(diethoxyphosphinoyl)butyrylamino)-4-t-butyldimethylsilyloxyphenyl)-4-(4-t-butyldimethylsilyloxyphenyl)-3-hexene (0.79 g, E-form) obtained by the process described in Example 32 was dissolved in tetrahydrofuran (2 ml), followed by adding thereto a solution of tetra-n-butylammonium fluoride (1.5 g) in tetrahydrofuran (1 ml). The resulting solution was stirred at 20° C. for 4 hours, and then ethyl acetate (100 ml) was added thereto and the organic layer was washed 4 times with water (50 ml), dried over anhydrous magnesium sulfate, and then concentrated under reduced pressure. The residue was purified by a silica gel column chromatography (methanol:chloroform =1:20) to obtain 3-(3-(4,4-bis (diethoxyphosphinoyl)butyrylamino)-4-hydroxyphenyl)-4-(4-hydroxyphenyl)-3-hexene (0.48 g, yield 83%).

$^1$H-NMR (CDCl$_3$) δ: ppm; 0.71 (3H×5/6, t, J=7.4 Hz; E-form), 0.73 (3H×5/6, t, J=7.4 Hz; E-form), 0.94 (3H×1/6, t, J=7.4 Hz; Z-form), 0.95 (3H×1/6, t, J=7.4 Hz;

Z-form), 1.30–1.43 (12H, m), 1.94–2.18 (4H, m), 2.20–2.63 (3H, m), 2.68 (2H×1/6, t, J=7.1 Hz; Z-form), 2.85 (2H×5/6, t, J=7.1 Hz; E-form), 4.10–4.30 (8H, m), 6.55–7.07 (7H, m), 7.50 (1H×1/6, br.s; Z-form), 7.98 (1H× 5/6, br.s; E-form), 8.68 (1H×1/6, br.s; Z-form), 9.02 (1H× 1/6, br.s; Z-form), 9.11 (1H×5/6, br.s; E-form), 9.30 (1H× 5/6, br.s; E-form).

EXAMPLE 34

3-(3-(4,4-Diphosphonobutyrylamino)-4-hydroxyphenyl)-4-(4-hydroxyphenyl)-3-hexene

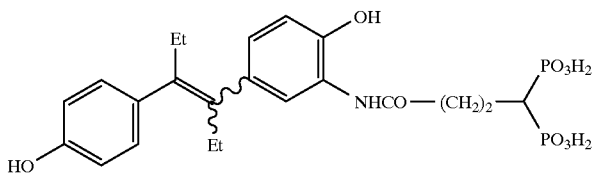

A crude product was obtained in the same manner as in Example 8 except for using 3-(3-(4,4-bis (diethoxyphosphinoyl)butyrylamino)-4-hydroxyphenyl)-4-(4-hydroxyphenyl)-3-hexene (0.48 g) obtained by the process described in Example 32, and then it was purified by a high-performance reversed phase column chromatography (a 0.1% aqueous trifluoroacetic acid solution:acetonitrile) to obtain 3-(3-(4,4-diphosphonobutyrylamino)-4-hydroxyphenyl)-4-(4-hydroxyphenyl)-3-hexene (74 mg, yield 19%).

$^1$H-NMR (D$_2$O) δ: ppm; 0.65 (6H×4/5, t, J=7.4 Hz; E-form), 0.82 (3H×1/5, t, J=7.3 Hz; Z-form), 0.83 (3H×1/5, t, J=7.3 Hz; Z-form), 1.83–2.49 (7H, m), 2.53–2.77 (2H, m), 6.51–7.26 (7H, m).

IR (KBr): cm$^{-1}$; 3442 (br.), 1684, 1654, 1209, 1144.

EXAMPLE 35

Erythro 3-(3-(3,3-bis(diisopropoxyphosphinoyl) propylsulfonylamino)-4-methoxymethoxyphenyl)-4-(4-methoxymethoxyphenyl)hexane

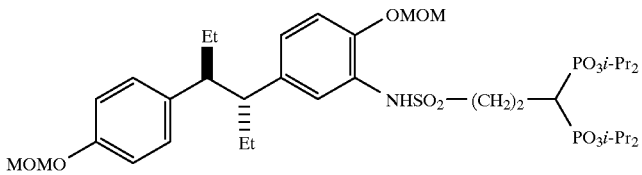

Under a nitrogen atmosphere, erythro 3-(3-amino-4-methoxymethoxyphenyl)-4-(4-methoxymethoxyphenyl) hexane (75 mg) obtained by the process described in Reference Example 4 and triethylamine (30 mg) were dissolved in dry methylene chloride (1 ml) and the resulting solution was cooled with ice. Then, a solution in dry methylene chloride (1 ml) of 3,3-bis(diisopropoxyphosphinoyl) propanesulfonyl chloride (1 equivalent per equivalent of the former) obtained by the process described in Reference Example 40 was added dropwise thereto. The reaction solution was washed with a cold aqueous sodium hydrogencarbonate solution, dried over anhydrous magnesium sulfate, and then concentrated under reduced pressure. The residue was purified by a silica gel thin-layer chromatography (acetone:chloroform=1:3) to obtain erythro 3-(3-(3,3-bis(diisopropoxyphosphinoyl)propylsulfonylamino)-4-methoxymethoxyphenyl)-4-(4-methoxymethoxyphenyl) hexane (70 mg, yield 43%).

$^1$H-NMR (CDCl$_3$) δ: ppm; 0.53 (6H, t, J=7.3 Hz), 1.31 (12H, d, J=6.3 Hz), 1.32 (12H, d, J=6.3 Hz), 2.26–2.60 (6H, m), 3.33–3.62 (3H, m), 3.51 (3H, s), 3.52 (3H, s), 4.65–4.90 (4H, m), 5.18 (2H, s), 5.23 (2H, s), 6.88 (1H, dd, J=2.0 Hz and 8.3 Hz), 6.93–7.14 (6H, m), 7.39 (1H, d, J=2.0 Hz).

EXAMPLE 36

Erythro 3-(3-(3,3-bis(diisopropoxyphosphinoyl) propylsulfonylamino)-4-hydroxyohenyl)-4-(4-hydroxyphenyl)hexane and erythro 3-(3-(3,3-bis (diisopropoxyphosphinoyl)propylsulfonylamino)-4-methoxymethoxyphenyl)-4-(4-hydroxyphenyl) hexane

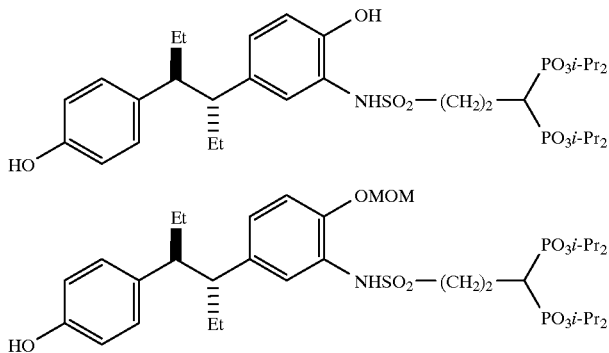

Erythro 3-(3-(3,3-bis(diisopropoxyphosphinoyl) propylsulfonylamino)-4-hydroxyphenyl)-4-(4-hydroxyphenyl)hexane (100 mg, yield 56%) and erythro 3-(3-(3,3-bis(diisopropoxyphosphinoyl) propylsulfonylamino)-4-methoxymethoxyphenyl)-4-(4-hydroxyphenyl)hexane (50 mg, yield 26%) were obtained in the same manner as in Example 7 except for using erythro 3-(3-(3,3-bis(diisopropoxyphosphinoyl) propylsulfonylamino)-4-methoxymethoxyphenyl)-4-(4-methoxymethoxyphenyl)hexane (0.20 g) obtained by the process described in Example 35.

Erythro 3-(3-(3,3-bis(diisopropoxyphosphinoyl) propylsulfonylamino)-4-hydroxyphenyl)-4-(4-hydroxyphenyl)hexane $^1$H-NMR (CDCl$_3$) δ: ppm; 0.60 (3H, t, J=7.3 Hz), 0.61 (3H, t, J=7.3 Hz), 1.2–1.6 (4H, m), 1.34 (12H, d, J=5.9 Hz), 1.35 (12H, d, J=5.9 Hz), 2.23–2.66 (5H, m), 3.20 (2H, t, J=7.3 Hz), 4.6–4.9 (4H, m), 6.53 (1H, s), 6.7–7.0 (7H, m), 7.25 (1H, s), 8.14 (1H, s).

Erythro 3-(3-(3,3-bis(diisopropoxyphosphinoyl) propylsulfonylamino)-4-methoxymethoxyphenyl)-4-(4-hydroxyphenyl)hexane $^1$H-NMR (CDCl$_3$) δ: ppm; 0.61 (3H, t, J=7.3 Hz), 0.62 (3H, t, J=7.3 Hz), 1.15–1.6 (28H, m), 2.24–2.66 (5H, m), 3.32 (2H, t, J=7.4 Hz), 3.50 (3H, s), 4.65–4.90 (4H, m), 5.20 (2H, s), 6.7–7.2 (9H, m).

EXAMPLE 37

Erythro 3-(3-(3,3-diphosphonopropylsulfonylamino)-4-hydroxyphenyl)-4-(4-hydroxyphenyl)hexane disodium salt

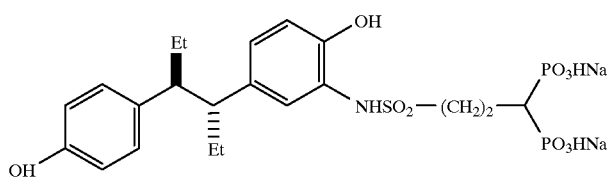

Erythro 3-(3-(3,3-diphosphonopropylsulfonylamino)-4-hydroxyphenyl)-4-(4-hydroxyphenyl)hexane disodium salt (44 mg, yield 35%) was obtained in the same manner as in Example 8 except for using erythro 3-(3-(3,3-bis (diisopropoxyphosphinoyl)propylsulfonylamino)-4-hydroxyphenyl)-4-(4-hydroxyphenyl)hexane (100 mg) and erythro 3-(3-(3,3-bis(diisopropoxyphosphinoyl) propylsulfonylamino)-4-methoxymethoxyphenyl)-4-(4-hydroxyphenyl)hexane (50 mg), which had been obtained by the process described in Example 36.

$^1$H-NMR (D$_2$O) δ: ppm; 0.46 (6H, t, J=5.4 Hz), 1.05–1.46 (4H, m), 2.1–2.9 (5H, m), 3.25–3.45 (2H, m), 6.7–7.1 (6H, s), 7.3 (1H, m).

IR (KBr): cm$^{-1}$; 3355 (br.), 1515, 1290, 1148.

REFERENCE EXAMPLE 1

Erythro 3-(3-amino-4-t-butyldimethylsilyloxypenyl)-4-(4-t-butyldimethylsilyloxyphenyl)hexane

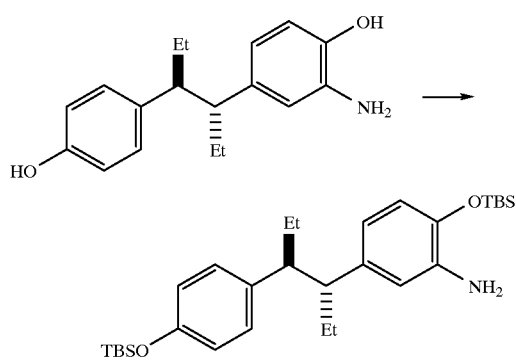

Under a nitrogen atmosphere, erythro 3-(3-amino-4-hydroxyphenyl)-4-(4-hydroxyphenyl)hexane (1.0 g) was dissolved in dry N,N-dimethylformamide (10 ml), and imidazole (978 mg) and t-butyldimethylsilyl chloride (2.2 g) were added thereto at room temperature and stirred for 1.5 hours. Water was added thereto, followed by extraction with diethyl ether, and the organic layer was washed successively with a 10% aqueous sodium hydrogencarbonate solution, water and a saturated aqueous sodium chloride solution, dried over anhydrous magnesium sulfate, and then concentrated under reduced pressure. The residue was purified by a silica gel column chromatography (chloroform) to obtain erythro 3-(3-amino-4-t-butyldimethylsilyloxyphenyl)-4-(4-t-butyldimethylsilyloxyphenyl)hexane (1.44 g, yield 80%).

$^1$H-NMR (CDCl$_3$) δ: ppm; 0.20 (6H, s), 0.25 (6H, s), 0.51 (3H, t, J=7.3 Hz), 0.52 (3H, t, J=7.3 Hz), 0.99 (9H, s), 1.03 (9H, s), 1.1–1.5 (4H, m), 2.2–2.5 (2H, m), 3.66 (2H, br.s), 6.40 (1H, dd, J=2.1 Hz and 8.1 Hz), 6.54 (1H, d, J=2.0 Hz), 6.66 (1H, d, J=8.3 Hz), 6.7–6.8 (2H, m), 6.9–7.05 (2H, m).

REFERENCE EXAMPLE 2

Erythro 3-(3-(3-chloropropionylamino)-4-t-butyldimethylsilyloxyphenl)-4-(4-t-butyldimethylsilyloxyphenyl)hexane

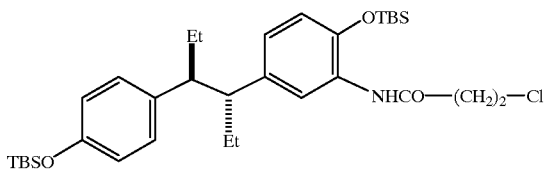

Under a nitrogen atmosphere, erythro 3-(3-amino-4-t-butyldimethylsilyloxyphenyl)-4-(4-t-butyldimethylsilyloxyphenyl)hexane (4.23 g) obtained by the process described in Reference Example 1 was dissolved in dry methylene chloride (30 ml) and the resulting solution was cooled to 0–5° C. Triethylamine (0.874 g) and then 3-chloropropionyl chloride (1.10 g) were added dropwise thereto. The resulting mixture was stirred at 0–5° C. for 2 hours, and then water was added thereto to effect extraction, and the organic layer was washed successively with a saturated aqueous sodium hydrogencarbonate solution, water, 1N hydrochloric acid, water and a saturated aqueous sodium chloride solution, dried over anhydrous magnesium sulfate, and then concentrated under reduced pressure. The residue was purified by recrystallization from isopropanol (30 ml) to obtain erythro 3-(3-(3-chloropropionylamino)-4-t-butyldimethylsilyloxyphenyl)-4-(4-t-butyldimethylsilyloxyphenyl)hexane (2.98 g, yield 60%).

$^1$H-NMR (CDCl$_3$) δ: ppm; 0.20 (6H, s), 0.29 (6H, s), 0.51 (3H, t, J=7.4 Hz), 0.52 (3H, t, J=7.3 Hz), 0.99 (9H, s), 1.05 (9H, s), 1.17–1.47 (4H, m), 2.37–2.57 (2H, m), 2.82 (2H, t, J=6.4 Hz), 3.91 (2H, t, J=6.4 Hz), 6.62–6.82 (4H, m), 6.92–7.07 (2H, m), 7.82 (1H, br.s), 8.24 (1H, br.s).

REFERENCE EXAMPLE 3

Erythro 3-(3-nitro-4-methoxymethxoyphenl)-4-(4-methoxymethoxyphenyl)hexane

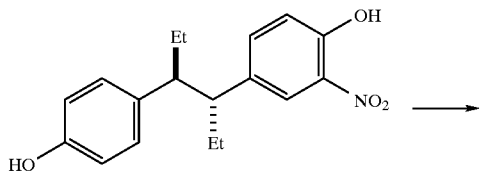

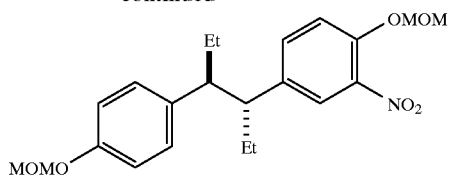

Under a nitrogen atmosphere, 60% sodium hydride (1.97 g) was suspended in dry N,N-dimethylformamide (50 ml), and the resulting suspension was cooled to 0–5° C. A solution of erythro 3-(3-nitro-4-hydroxyphenyl)-4-(4-hydroxyphenyl)hexane (6.22 g) in dry N,N-dimethylformamide (50 ml) was added dropwise thereto and the resulting mixture was stirred at the same temperature for 10 minutes, and then chloromethylmethyl ether (3.7 ml) was added thereto. The resulting mixture was heated to room temperature and stirred overnight, and water was added thereto, followed by extraction with methylene chloride. The organic layer was washed successively with water, 1N hydrochloric acid, water and a saturated aqueous sodium chloride solution, dried over anhydrous magnesium sulfate, and then concentrated under reduced pressure. The residue was purified by a silica gel column chromatography (ethyl acetate:hexane=1:20) to obtain erythro 3-(3-nitro-4-methoxymethoxyphenyl)-4-(4-methoxymethoxyphenyl)hexane (7.45 g, yield 94%).

$^1$H-NMR (CDCl$_3$) δ: ppm; 0.55 (3H, t, J=7.3 Hz), 0.56 (3H, t, J=7.3 Hz), 1.15–1.55 (4H, m), 2.40–2.65 (2H, m), 3.51 (3H, s), 3.56 (3H, s), 5.18 (2H, s), 5.29 (2H, s), 6.9–7.1 (4H, m), 7.2–7.35 (2H, m), 7.61 (1H, d, J=1.7 Hz).

REFERENCE EXAMPLE 4

Erythro 3-(3-amino-4-methoxymethoxyphenyl)-4-(4-methoxymethoxyphenyl)hexane

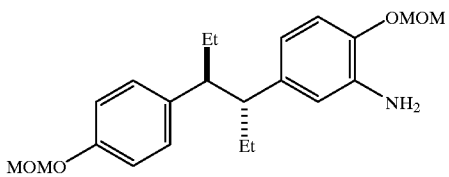

Under a nitrogen atmosphere, erythro 3-(3-nitro-4-methoxymethoxyphenyl)-4-(4-methoxymethoxyphenyl)hexane (1.95 g) obtained by the process described in Reference Example 3 was dissolved in acetic acid (20 ml), and then 10% palladium-carbon (0.186 g) was added thereto and hydrogenation was carried out at room temperature under atmospheric pressure. The catalyst was filtered off and the filtrate was concentrated under reduced pressure, and then the residue was dissolved in ethyl acetate and the resulting solution was neutralized with a aqueous sodium hydrogencarbonate solution. After extraction (twice) with ethyl acetate, the organic layer was washed with water and then a saturated aqueous sodium chloride solution, dried over anhydrous magnesium sulfate, and then concentrated under reduced pressure. The residue was purified by a silica gel column chromatography (ethyl acetate:hexane=1:10) to obtain erythro 3-(3-amino-4-methoxymethoxyphenyl)-4-(4-methoxymethoxyphenyl)hexane (1.81 g, quantitative yield).

$^1$H-NMR (CDCl$_3$) δ: ppm; 0.52 (3H, t, J=7.3 Hz), 0.53 (3H, t, J=7.3 Hz), 1.1–1.5 (4H, m), 2.3–2.5 (2H, m), 3.51

(3H, s), 3.53 (3H, s), 3.7–3.9 (2H, br.s), 5.18 (2H, s), 5.19 (2H, s), 6.51 (1H, dd, J=2.0 Hz and 8.3 Hz), 6.57 (1H, d, J=2.3 Hz), 6.90–7.13 (5H, m).

REFERENCE EXAMPLE 5

Ethyl 3,3-bis(diisopropoxyphosphinoyl)propionate

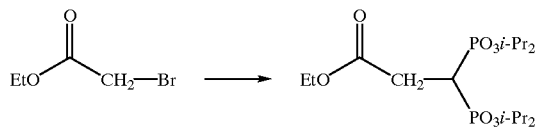

Under a nitrogen atmosphere, 60% sodium hydride (0.132 g) was suspended in dry tetrahydrofuran (4 ml), and tetraisopropyl methylenebisphosphonate (1.1 g) was added dropwise thereto at room temperature. After stirring for 10 minutes, ethyl bromoacetate (0.354 ml) was added dropwise thereto and the resulting mixture was stirred at the same temperature for 1 hour. Water was added thereto, followed by extraction (twice) with ethyl acetate, and the organic layer was dried over anhydrous magnesium sulfate and concentrated under reduced pressure. The residue was purified by a silica gel column chromatography (methanol:methylene chloride=2:98) to obtain ethyl 3,3-bis (diisopropoxyphosphinoyl)propionate (0.37 g, yield 27%).

$^1$H-NMR (CDCl$_3$) δ: ppm; 1.15–1.45 (27H, m), 2.7–3.1 (3H, m), 4.18 (2H, q, J=7.1 Hz), 4.7–4.9 (4H, m).

REFERENCE EXAMPLE 6

3,3-Bis(diisopropoxyphosphinoyl)propionic acid

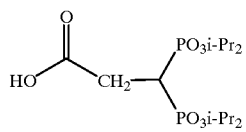

Under a nitrogen atmosphere, ethyl 3,3-bis (diisopropoxyphosphinoyl)propionate (0.37 g) obtained by the process described in Reference Example 5 was dissolved in ethanol (5 ml), followed by adding thereto a 2N aqueous sodium hydroxide solution (0.5 ml), and the resulting mixture was stirred overnight at room temperature. The mixture was stirred under reflux for another 1 hour. The mixture was acidified with 1N hydrochloric acid and extracted with ethyl acetate, and the organic layer was washed with a saturated aqueous sodium chloride solution, dried over anhydrous magnesium sulfate, and then concentrated under reduced pressure to obtain 3,3-bis(diisopropoxyphosphinoyl) propionic acid (0.323 g, yield 93%).

$^1$H-NMR (CDCl$_3$) δ: ppm; 1.2–1.4 (24H, m), 2.7–3.1 (3H, m), 4.7–4.9 (4H, m), 6.3 (1H, br.s).

REFERENCE EXAMPLE 7

5,5-Bis(diisopropoxyphosphinoyl)valeric acid

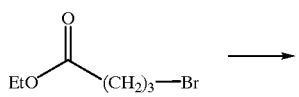

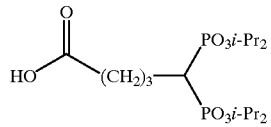

Under a nitrogen atmosphere, 60% sodium hydride (2.56 g) was suspended in dry N,N-dimethylformamide (20 ml), and tetraisopropyl methylenebisphosphonate (20.0 g) was added dropwise thereto at room temperature. After stirring for 10 minutes, ethyl bromobutyrate (8.4 ml) was added dropwise thereto and the resulting mixture was stirred at 100° C. for 1 hour. Then, sodium iodide (0.85 g) was added thereto and stirred for 4 hours. Water was added thereto, followed by extraction (twice) with ethyl acetate, and the organic layer was dried over anhydrous magnesium sulfate and concentrated under reduced pressure. The residue was dissolved in methanol (50 ml), followed by adding thereto a 2N aqueous sodium hydroxide solution (10 ml), and the resulting mixture was stirred with heating under reflux for 3 hours. The mixture was acidified with 1N hydrochloric acid and extracted with ethyl acetate, and the organic layer was washed with a saturated aqueous sodium chloride solution, dried over anhydrous magnesium sulfate, and then concentrated under reduced pressure, and then the residue was purified by a silica gel column chromatography to obtain 5,5-bis(diisopropoxyphosphinoyl)valeric acid (1.88 g, yield 8.7%). $^1$H-NMR (CDCl$_3$) δ: ppm; 1.34 (12H, d, J=6.3 Hz), 1.34 (12H, d, J=5.9 Hz), 1.8–2.4 (7H, m), 4.7–4.9 (4H, m).

REFERENCE EXAMPLE 8

4,4-Bis(diisopropoxyphosphinoyl)butyric acid

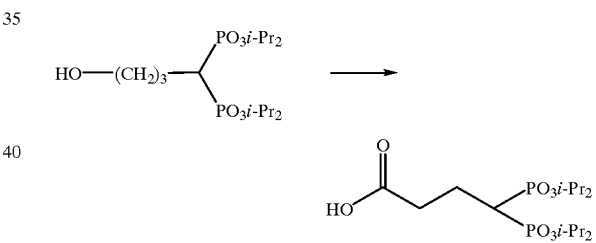

Under a nitrogen atmosphere, 4,4-bis (diisopropoxyphosphinoyl)-1-butanol (10.12 g) was dissolved in acetone (30 ml), and the resulting solution was cooled to 0–5° C. A solution of chromium trioxide (2.7 g) and concentrated sulfuric acid (2.3 ml) in water (8 ml) was added dropwise thereto, and the resulting mixture was stirred at 0–5° C. for 2 hours. The mixture was stirred at room temperature for another 10 hours, and then isopropanol (15 ml) was added dropwise thereto and stirred for 30 minutes. The resulting mixture was neutralized with a saturated aqueous sodium hydrogencarbonate solution and the insoluble materials were removed by filtration through Celite. The filtrate was acidified with hydrochloric acid and extracted three times with chloroform, and the organic layer was washed with water and then a saturated aqueous sodium chloride solution, dried over anhydrous magnesium sulfate, and then concentrated under reduced pressure to obtain 4,4-bis(diisopropoxyphosphinoyl)butyric acid (6.75 g, yield 64%).

$^1$H-NMR (CDCl$_3$) δ: ppm; 1.34 (12H, d, J=5.9 Hz), 1.35 (12H, d, J=5.9 Hz), 2.05–2.60 (3H, m), 2.68 (2H, t, J=7.4 Hz), 4.65–4.90 (4H, m).

IR (KBr): cm$^{-1}$; 2980 (br.), 1728, 1424, 1387, 1297, 887, 847, 824, 767, 688.

REFERENCE EXAMPLE 9

Benzyl 4,4-bis(diethoxyphosphinoyl)-2-benzyloxycarbonylbutyrate

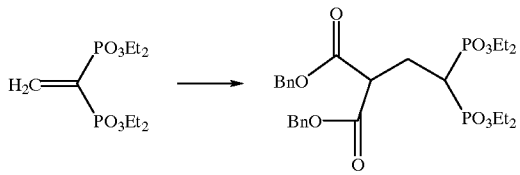

Under a nitrogen atmosphere, dibenzyl malonate (1.71 g) was dissolved in isopropanol (10 ml) and sodium methoxide (27 mg) was suspended therein. A solution of tetraethyl ethenylidenebisphosphonate (1.51 g) in isopropanol (5 ml) was added dropwise thereto at room temperature and stirred for 2 hours. A saturated aqueous ammonium chloride solution (2.5 ml) and a saturated aqueous sodium chloride solution were added to the reaction mixture, followed by extraction (twice) with ethyl acetate. The organic layer was dried over anhydrous magnesium sulfate and concentrated under reduced pressure, and the residue was purified by a silica gel column chromatography (chloroform:acetone=9:1 to 2:1) to obtain benzyl 4,4-bis(diethoxyphosphinoyl)-2-benzyloxycarbonylbutyrate (1.91 g, yield 65%).

$^1$H-NMR (CDCl$_3$) δ: ppm; 1.29 (6H, t, J=7.1 Hz), 1.30 (6H, t, J=7.1 Hz), 2.36–2.72 (3H, m), 4.05–4.22 (9H, m), 5.14 (4H, s), 7.23–7.35 (10H, m).

REFERENCE EXAMPLE 10

4,4-Bis(diethoxyphosphinoyl)-2-carboxybutyric acid

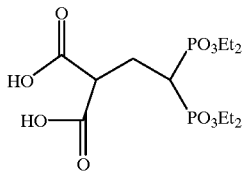

Benzyl 4,4-bis(diethoxyphosphinoyl)-2-benzyloxycarbonylbutyrate (1.90 g) obtained by the process described in Reference Example 9 was dissolved in methanol (50 ml), and hydrogenolysis was carried out for 3.5 hours in the presence of 10% palladium-carbon (0.3 g) at room temperature under atmospheric pressure. The catalyst was filtered off and the filtrate was concentrated under reduced pressure to obtain 4,4-bis(diethoxyphosphinoyl)-2-carboxybutyric acid (1.27 g, yield 96%).

IR (KBr): cm$^{-1}$; 2987 (br.), 2910 (br.), 1734, 1710, 1399, 1333, 1290, 859, 848, 814, 781, 738.

REFERENCE EXAMPLE 11

4,4-Bis(diethoxyphosphinoyl)butyric acid

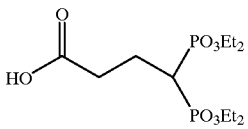

Under a nitrogen atmosphere, 4,4-bis(diethoxyphosphinoyl)-2-carboxybutyric acid (1.27 g) obtained by the process described in Reference Example 10 was heated at 130° C. for 3 hours to obtain 4,4-bis(diethoxyphosphinoyl)butyric acid (1.13 g, quantitative yield).

$^1$H-NMR (CDCl$_3$) δ: ppm; 1.34 (12H, t, J=7.1 Hz), 2.1–2.35 (2H, m), 2.45–2.75 (3H, m), 4.1–4.3 (8H, m).

REFERENCE EXAMPLE 12

6,6-Bis(diisopropoxyphosphinoyl)hexanoic acid

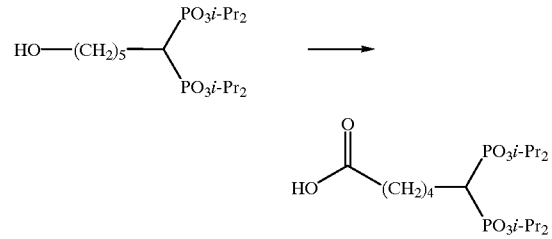

6,6-Bis (diisopropoxyphosphinoyl)hexanoic acid (6.08 g, yield 54%) was obtained in the same manner as in Reference Example 8 except for using 6,6-bis(diisopropoxyphosphinoyl)-1-hexanol (12.11 g).

$^1$H-NMR (CDCl$_3$) δ: ppm; 1.34 (24H, d, J=6.3 Hz), 1.51–1.72 (4H, m), 1.76–2.29 (3H, m), 2.29–2.41 (2H, m), 4.6–4.9 (4H, m).

REFERENCE EXAMPLE 13

Mono-p-nitrobenzyl succinate

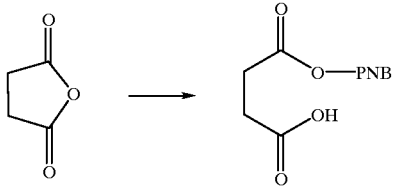

Succinic anhydride (3.6 g), p-nitrobenzyl alcohol (4.59 g) and N,N-dimethylaminopyridine (0.183 g) were suspended in toluene (60 ml)-pyridine (10 ml), and the resulting suspension was heated under reflux for 1.5 hours. The reaction mixture was poured into cold diluted sulfuric acid, and the precipitated crystals were collected by filtration, washed twice with water and then twice with cold toluene, and dried under reduced pressure to obtain mono-p-nitrobenzyl succinate (6.05 g, yield 80%).

IR (KBr): cm$^{-1}$; 3118 (br.), 1736, 1678, 1612, 1533, 1351, 863, 844, 736.

REFERENCE EXAMPLE 14 p-Nitrobenzyl 4,4-bis(dimethoxyphosphinoyl)-4-trimethylsilyloxybutyrate

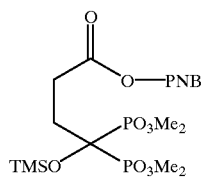

Under a nitrogen atmosphere, mono-p-nitrobenzyl succinate (2.53 g) obtained by the process described in Reference Example 13 was suspended in dry methylene chloride (25 ml), and a catalytic amount of dry N,N-dimethylformamide was added thereto, followed by adding dropwise thereto a solution of oxalic dichloride (1.52 g) in dry methylene chloride (5 ml). The resulting mixture was stirred at room temperature for 1 hour and then concentrated under reduced pressure, and the residue was redissolved in dry tetrahydrofuran (25 ml). A solution of trimethyl phosphite (1.24 g) in dry tetrahydrofuran (5 ml) was added thereto at room temperature and the resulting solution was heated under reflux for 1 hour. After this solution was cooled to room temperature, a solution of dimethyltrimethylsilyl phosphite (1.82 g) in dry tetrahydrofuran (5 ml) was added thereto, and the resulting solution was stirred at room temperature for 24 hours. The reaction solution was diluted with chloroform and ice water was added thereto to effect extraction (three times). The organic layer was dried over anhydrous magnesium sulfate and concentrated under reduced pressure, and the residue was purified by a silica gel column chromatography (chloroform:acetone =100:0 to 80:20) to obtain p-nitrobenzyl 4,4-bis(dimethoxyphosphinoyl)-4-trimethylsilyloxybutyrate (3.35 g, yield 64%).

$^1$H-NMR (CDCl$_3$) δ: ppm; 0.23 (9H, s), 2.3–2.55 (2H, m), 2.7–2.8 (2H, m), 3.75–3.95 (12H, m), 5.22 (2H, s), 7.53 (2H, d, J=8.9 Hz), 8.23 (2H, d, J=8.9 Hz).

IR (neat): cm$^{-1}$; 1742, 1522.

REFERENCE EXAMPLE 15

4,4-Bis(dimethoxyphosphinoyl)-4-trimethylsilyloxybutyric acid

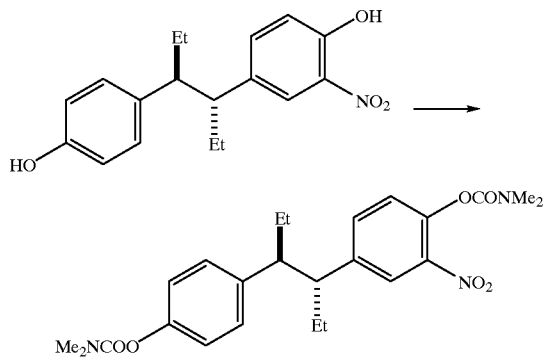

p-Nitrobenzyl 4,4-bis(dimethoxyphosphinoyl)-4-trimethylsilyloxybutyrate (1.68 g) obtained by the process described in Reference Example 14 was dissolved in tetrahydrofuran (40 ml), and hydrogenolysis was carried out for 3.3 hours in the presence of 10% palladium-carbon (1.68 g) at room temperature under atmospheric pressure. The catalyst was filtered off and the filtrate was concentrated under reduced pressure, and then the residue was purified by a silica gel column chromatography (chloroform:methanol= 95:5 to 85:15) to obtain 4,4-bis(dimethoxyphosphinoyl)-4-trimethylsilyloxybutyric acid (1.27 g, quantitative yield).

$^1$H-NMR (CDCl$_3$) δ: ppm; 0.24 (9H, s), 2.3–2.5 (2H, m), 2.6–2.8 (2H, m), 3.8–3.95 (12H, m).

REFERENCE EXAMPLE 16

Erythro 3-(3-nitro-4-dimethylcarbamoyloxyphenyl)-4-(4-dimethylcarbamoyloxyphenyl)hexane

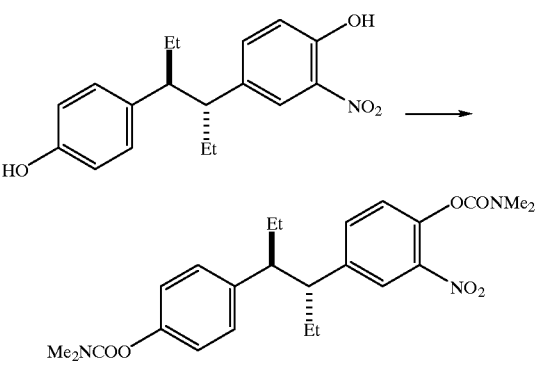

Under a nitrogen atmosphere, triethylamine (13.8 ml), dimethylcarbamoyl chloride (9 ml) and 4-dimethylaminopyridine (125 mg) were added in that order to a solution of erythro 3-(3-nitro-4-hydroxyphenyl)-4-(4-hydroxyphenyl)hexane (4.21 g) in dry N,N-dimethylformamide (90 ml) at 0–5° C., and the resulting mixture was heated to room temperature and stirred for 2 days. The reaction mixture was diluted with water and extracted twice with a mixed solvent of diethyl ether and ethyl acetate. The organic layer was washed with water and then a saturated aqueous sodium chloride solution, dried over anhydrous magnesium sulfate, and then concentrated under reduced pressure to obtain erythro 3-(3-nitro-4-dimethylcarbamoyloxyphenyl)-4-(4-dimethylcarbamoyloxyphenyl)hexane (5.14 g, quantitative yield).

$^1$H-NMR (CDCl$_3$) δ: ppm; 0.55 (3H, t, J=7.3 Hz), 0.55 (3H, t, J=7.3 Hz), 1.2–1.6 (4H, m), 2.50–2.75 (2H, in), 3.02 (3H, s), 3.04 (3H, s), 3.11 (3H, s), 3.15 (3H, s), 7.0–7.3 (5H, m), 7.40 (1H, dd, J=2.3 Hz and 8.2 Hz), 7.87 (1H, d, J=2.3 Hz).

REFERENCE EXAMPLE 17

Erythro 3-(3-amino-4-dimethylcarbamoyloxyphenyl)-4-(4-dimethylcarbamoyloxyphenyl)hexane

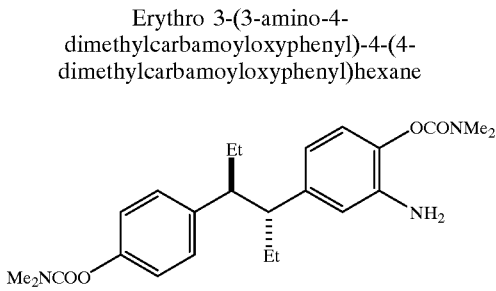

Erythro 3-(3-nitro-4-dimethylcarbamoyloxyphenyl)-4-(4-dimethylcarbamoyloxyphenyl)hexane (5.14 g) obtained by the process described in Reference Example 16 was dissolved in acetic acid (30 ml), and then 10% palladium-carbon (0.5 g) was added thereto and hydrogenation was carried out for 1 hour at room temperature under atmospheric pressure. Thereafter, erythro 3-(3-amino-4-dimethylcarbamoyloxyphenyl)-4-(4-dimethylcarbamoyloxyphenyl)hexane (1.17 g, yield 21%) was obtained in the same manner as in Reference Example 4.

$^1$H-NMR (CDCl$_3$) δ: ppm; 0.52 (3H, t, J=7.3 Hz), 0.53 (3H, t, J=7.3 Hz), 1.2–1.6 (4H, m), 2.4–2.6 (2H, m), 3.02 (3H, s), 3.02 (3H, s), 3.10 (3H, s), 3.13 (3H, s), 3.66 (2H, br.s), 6.5–6.65 (2H, m), 6.94 (1H, d, J=8.6 Hz), 7.0–7.2 (4H, m).

REFERENCE EXAMPLE 18

Erythro 3-(3-(1-p-nitrobenzyloxycarbonylamino-1-cyclohexylcarbonylamino)-4-methoxymethoxyphenyl)-4-(4-methoxymethoxyphenyl)hexane

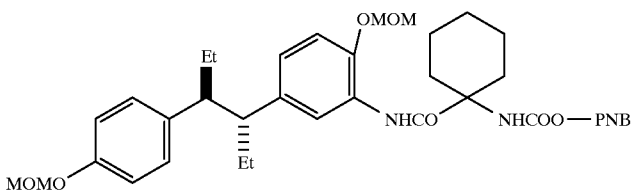

Erythro 3-(3-(1-p-nitrobenzyloxycarbonylamino-1-cyclohexylcarbonylamino)-4-methoxymethoxyphenyl)-4-(4-methoxymethoxyphenyl)hexane (0.87 g, yield 43%) was obtained in the same manner as in Example 4 except for using erythro 3-(3-amino-4-methoxymethoxyphenyl)-4-(4-methoxymethoxyphenyl)hexane (1.12 g) obtained by the process described in Reference Example 4 and 1-p-nitrobenzyloxycarbonylamino-1-cyclohexanecarboxylic acid (0.97 g).

$^1$H-NMR (CDCl$_3$) δ: ppm; 0.51 (3H, t, J=7.3 Hz), 0.53 (3H, t, J=7.3 Hz), 1.20–1.52 (6H, m), 1.64–1.81 (4H, m), 1.94–2.28 (4H, m), 2.45–2.55 (2H, m), 3.46 (3H, br.s), 3.51 (3H, s), 5.11 (2H, br.s), 5.18 (2H, s), 5.22 (2H, s), 6.82 (1H, br.d, J=8.6 Hz), 6.9–7.15 (5H, m), 7.4–7.6 (2H, m), 8.1–8.25 (2H, m), 8.29 (1H, d, J=1.7 Hz), 8.89 (1H, br.s).

REFERENCE EXAMPLE 19

Erythro 3-(3-(1-p-nitrobenzyloxycarbonylamino-1-cyclohexylcarbonylamino)-4-hydroxyphenyl)-4-(4-hydroxyphenyl)hexane

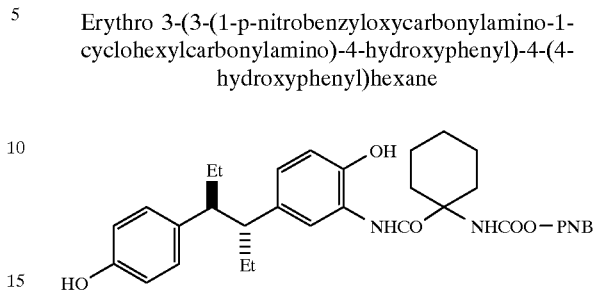

Erythro 3-(3-(1-p-nitrobenzyloxycarbonylamino-1-cyclohexylcarbonylamino)-4-methoxymethoxyphenyl)-4-(4-methoxymethoxyphenyl)hexane (0.87 g) obtained by the process described in Reference Example 18 was dissolved in methanol (6.5 ml), followed by adding dropwise thereto 6N hydrochloric acid (0.43 g) at 20° C. The resulting mixture was stirred at the same temperature for 1 hour. Thereafter, erythro 3-(3-(1-p-nitrobenzyloxycarbonylamino-1-cyclohexylcarbonylamino)-4-hydroxyphenyl)-4-(4-hydroxyphenyl)hexane (0.89 g, quantitative yield) was obtained in the same manner as in Example 7.

$^1$H-NMR (CDCl$_3$) δ: ppm; 0.45–0.65 (6H, m), 1.13–1.83 (10H, m), 1.95–2.26 (4H, m), 2.36–2.52 (2H, m), 5.26 (2H, s), 6.70–6.85 (2H, m), 6.85–7.06 (4H, m), 7.45–7.60 (2H, m), 8.02–8.30 (3H, m), 8.71 (1H, br.s).

REFERENCE EXAMPLE 20

Erythro 3-(3-(1-amino-1-cyclohexylcarbonylamino)-4-hydroxyphenyl)-4-(4-hydroxyphenyl)hexane

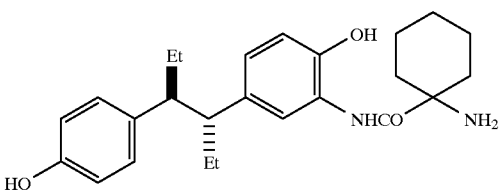

Erythro 3-(3-(1-p-nitrobenzyloxycarbonylamino-1-cyclohexylcarbonylamino)-4-hydroxyphenyl)-4-(4-hydroxyphenyl)hexane (0.76 g) obtained by the process described in Reference Example 19 was dissolved in methanol (7 ml), and then 10% palladium-carbon (0.15 g) was added thereto and hydrogenation was carried out for 6 hours at room temperature under atmospheric pressure. Thereafter, erythro 3-(3-(1-amino-1-cyclohexylcarbonylamino)-4-hydroxyphenyl)-4-(4-hydroxyphenyl)hexane (427 mg, yield 81%) was obtained in the same manner as in Reference Example 15.

$^{1}$H-NMR (CDCl$_{3}$) δ: ppm; 0.53 (3H, t, J=7.3 Hz), 0.54 (3H, t, J=7.4 Hz), 1.14–1.84 (12H, m), 2.03–2.20 (2H, m), 2.33–2.50 (2H, m), 4.7 (1H, br.s), 6.65 (1H, d, J=2.0 Hz), 6.75–6.81 (2H, m), 6.90 (1H, dd, J=2.0 Hz and 8.3 Hz), 6.93–7.03 (3H, m), 9.66 (1H, s), 10.31 (1H, s).

REFERENCE EXAMPLE 21

Benzyl 4 4-bis(diethoxyphosphinoyl)-2-benzyloxycarbonyl-2-methylbutyrate

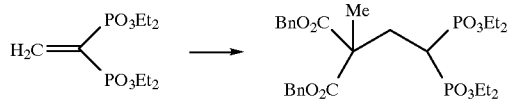

Benzyl 4,4-bis(diethoxyphosphinoyl)-2-benzyloxycarbonyl-2-methylbutyrate (2.0 2 g, yield 68%) was obtained in the same manner as in Reference Example 9 except for using dibenzyl methylmalonate (1.8 g) and tetraethyl ethenylidenebisphosphonate (1.5 g).

$^{1}$H-NMR (CDCl$_{3}$) δ: ppm; 1.25–1.40 (12H, m), 1.50 (3H, s), 2.45–2.75 (3H, m), 4.05–4.25 (8H, m),5.0–5.25 (4H, m) 7.20–7.33 (10H, m).

REFERENCE EXAMPLE 22

4,4-Bis(diethoxyphosphinoyl)-2-carboxyl-2-methylbutyric acid

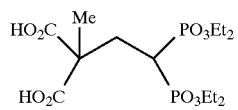

4, 4-Bis (diethoxyphosphinoyl)-2-carboxy-2-methylbutyric acid (0.33 g, yield 94%) was obtained in the same manner as in Reference Example 10 except for using benzyl 4,4-bis(diethoxyphosphinoyl)-2-benzyloxycarbonyl-2-methylbutyrate (0.50 g) obtained by the process described in Reference Example 21.

$^{1}$H-NMR (CD$_{3}$SOCD$_{3}$) δ: ppm; 20 1.24 (12H, t, J=7.1 Hz), 1.26 (3H, s), 2.21–2.46 (3H, m), 3.94–4.12 (8H, m), 12.70 (2H, br.s).

REFERENCE EXAMPLE 23

4,4-Bis(diethoxyphosphinoyl)-2-methylbutyric acid

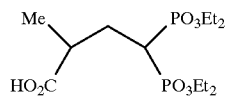

4,4-Bis(diethoxyphosphinoyl)-2-methylbutyric acid (quantitative yield) was obtained in the same manner as in Reference Example 11 except for using 4,4-bis (diethoxyphosphinoyl)-2-carboxy-2-methylbutyric acid (0.98 g) obtained by the process described in Reference Example 22.

$^{1}$H-NMR (CDCl$_{3}$) δ: ppm; 1.22 (3H, d, J=6.9 Hz), 1.34 (12H, t, J=7.1 Hz), 1.78–2.04 (1H, m), 2.13–2.43 (1H, m), 2.52–2.18 (1H, m), 2.84–3.02 (1H, m), 4.10–4.27 (8H, m).

REFERENCE EXAMPLE 24

Erythro 3-(3-ethoxycarbonylacetylamino-4-methoxymethoxyphenyl)-4-(4-methoxymethoxyphenyl)hexane

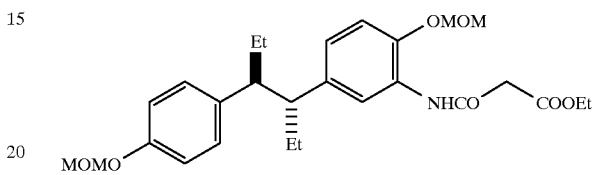

Erythro 3-(3-ethoxycarbonylacetylamino-4-methoxymethoxyphenyl)-4-(4-methoxymethoxyphenyl)hexane (0.86 g, yield 88%) was obtained in the same manner as in Reference Example 2 except for using erythro 3-(3-amino-4-methoxymethoxyphenyl)-4-(4-methoxymethoxyphenyl)hexane (0.75 g) obtained by the process described in Reference Example 4 and ethylmalonyl chloride (0.31 ml).

$^{1}$H-NMR (CDCl$_{3}$) δ: ppm; 0.51 (3H, t, J=7.4 Hz), 0.52 (3H, t, J=7.3 Hz), 1.21–1.42 (4H, m), 1.33 (3H, t, J=7.3 Hz), 2.45–2.54 (2H, m), 3.51 (3H, s), 3.52 (2H, s), 3.56 (3H, s), 4.27 (2H, q, J=7.2 Hz), 5.18 (2H, s), 5.27 (2H, s), 6.83 (1H, dd, J=2.0 Hz and 8.6 Hz), 6.94–7.02 (2H, m), 7.03–7.13 (3H, m), 8.28 (1H, d, J=2.0 Hz), 9.52 (1H, br.s).

REFERENCE EXAMPLE 25

Erythro 3-(3-carboxyacetylamino-4-methoxymethoxyphenyl)-4-(4-methoxymethoxyphenyl)hexane

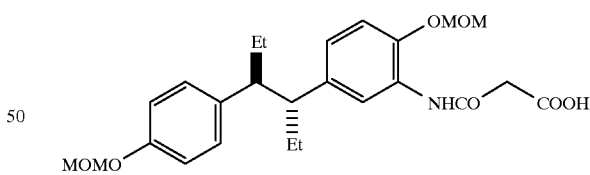

Erythro 3-(3-carboxyacetylamino-4-methoxymethoxyphenyl)-4-(4-methoxymethoxyphenyl)hexane (0.46 g, quantitative yield) was obtained in the same manner as in Reference Example 6 except for using erythro 3-(3-ethoxycarbonylacetylamino-4-methoxymethoxyphenyl)-4-(4-methoxymethoxyphenyl)hexane (0.47 g) obtained by the process described in Reference Example 24.

$^{1}$H-NMR (CDCl$_{3}$) δ: ppm; 0.53 (6H, t, J=7.3 Hz), 1.17–1.48 (4H, m), 2.43–2.55 (2H, m), 3.43–3.60 (8H, m), 5.18 (2H, s), 5.25 (2H, s), 6.87–6.93 (1H, m), 6.95–7.02 (2H, m), 7.05–7.13 (3H, m), 8.14 (1H, s), 8.53 (1H, br.s).

REFERENCE EXAMPLE 26

Erythro 3-(3-bromoacetylamino-4-methoxymethoxyphenyl)-4-(4-methoxymethoxyphenyl)hexane

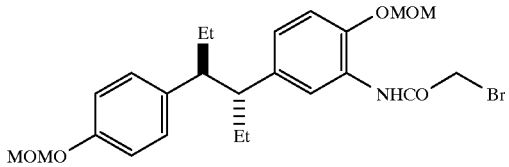

Erythro 3-(3-bromoacetylamino-4-methoxymethoxyphenyl)-4-(4-methoxymethoxyphenyl) hexane (0.87 g, yield 88%) was obtained in the same manner as in Reference Example 2 except for using erythro 3-(3-amino-4-methoxymethoxyphenyl)-4-(4-methoxymethoxyphenyl)hexane (0.75 g) obtained by the process described in Reference Example 4 and bromoacetyl chloride (0.20 ml).

$^1$H-NMR (CDCl$_3$) δ: ppm; 0.51 (3H, t, J=7.3 Hz), 0.52 (3H, t, J=7.4 Hz), 1.16–1.47 (4H, m), 2.43–2.57 (2H, m), 3.51 (3H, s), 3.55 (3H, s), 4.06 (2H, s), 5.18 (2H, s), 5.27 (2H, s), 6.87 (1H, dd, J=2.3 Hz and 8.3 Hz), 6.94–7.14 (5H, m), 8.23 (1H, d, J=2.0 Hz), 8.88 (1H, br.s).

REFERENCE EXAMPLE 27

N-p-Nitrobenzyloxycarbonyl-3-trimethylsilyloxy-3,3-bis(dimethoxyphosphinoyl)propylamine

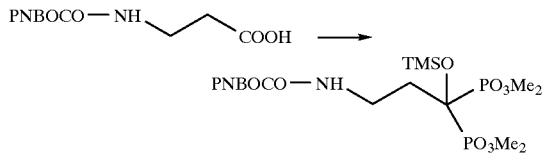

N-p-Nitrobenzyloxycarbonyl-3-trimethylsilyloxy-3,3-bis(dimethoxyphosphinoyl)propylamine (1.57 g, yield 58%) was obtained in the same manner as in Reference Example 14 except for using N-p-nitrobenzyloxycarbonyl β-alanine (1.34 g).

$^1$H-NMR (CDCl$_3$) δ: ppm; 0.23 (9H, s), 2.1–2.4 (2H, m), 3.4–3.6 (2H, m), 3.75–3.95 (12H, m), 5.19 (2H, s), 5.77 (1H, m), 7.50 (2H, d, J=8.9 Hz), 8.21 (2H, d, J=8.9 Hz).

IR (neat): cm$^{-1}$; 3300 (br.), 1727, 1528, 1349, 1255 (br.).

REFERENCE EXAMPLE 28

3,3-Bis(dimethoxyphosphinoyl)-3-hydroxypropylamine

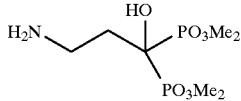

N-p-Nitrobenzyloxycarbonyl-3-trimethylsilyloxy-3,3-bis(dimethoxyphosphinoyl)propylamine (1.43 g) obtained by the process described in Reference Example 27 was dissolved in tetrahydrofuran (30 ml), and hydrogenolysis was carried out for 2 hours in the presence of 10% palladium-carbon (1.43 g) at room temperature under atmospheric pressure. The catalyst was filtered off and the precipitate on a filter was washed successively with tetrahydrofuran, methanol and chloroform. The filtrate and washings were concentrated together under reduced pressure, and the residue was dissolved in methanol, and then hexane was added thereto to carry out washing and separation (twice). The methanol layer was concentrated under reduced pressure to obtain 3,3-bis(dimethoxyphosphinoyl)-3-hydroxypropylamine (0.97 g, quantitative yield).

$^1$H-NMR (CDCl$_3$) δ: ppm; 2.2–2.7 (5H, m), 3.1–3.5 (2H, m), 3.75–4.0 (12H, m).

REFERENCE EXAMPLE 29

Mono-p-nitrobenzyl glutarate

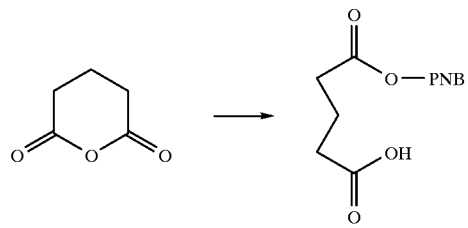

Mono-p-nitrobenzyl glutarate (4.2 g, yield 53%) was obtained according to the process described in Reference Example 13, except for using glutaric anhydride (4.1 g).

$^1$H-NMR (CDCl$_3$) δ: ppm; 1.90–2.10 (2H, m), 2.46 (2H, t, J=7.1 Hz), 2.51 (2H, t, J=7.3 Hz), 5.22 (2H, s), 7.52 (2H, d, J=8.9 Hz), 8.23 (2H, d, J=8.9 Hz).

REFERENCE EXAMPLE 30 p-Nitrobenzyl 5,5-bis(dimethoxyphosphinoyl)-5-trimethylsilyloxyvalerate

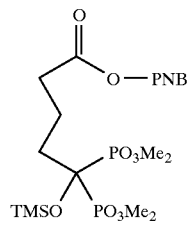

p-Nitrobenzyl 5,5-bis(dimethoxyphosphinoyl)-5-trimethylsilyloxyvalerate (4.9 g, yield 89%) was obtained according to the process described in Reference Example 14, except for using mono-p-nitrobenzyl glutarate (2.7 g) obtained by the process described in Reference Example 29.

$^1$H-NMR (CDCl$_3$) δ: ppm; 0.22 (9H, s), 1.90–2.20 (4H, m), 2.42 (2H, t, J=7.1 Hz), 3.80–3.88 (12H, m), 5.22 (2H, s), 7.53 (2H, d, J=8.9 Hz), 8.23 (2H, d, J=8.9 Hz).

REFERENCE EXAMPLE 31

5,5-Bis(dimethoxyphosphinoyl)-5-trimethylsilyloxyvaleric acid

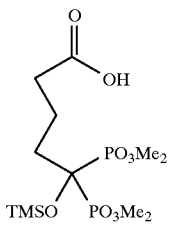

5,5-Bis(dimethoxyphosphinoyl)-5-trimethylsilyloxyvaleric acid (1.7 g, yield 46%) was obtained according to the process described in Reference Example 15, except for using p-nitrobenzyl 5,5-bis(dimethoxyphosphinoyl)-5-trimethylsilyloxyvalerate (4.9 g) obtained by the process described in Reference Example 30.

$^1$H-NMR (CDCl$_3$) δ: ppm; 0.22 (9H, s), 1.84–2.21 (4H, m), 2.34 (2H, t, J=7.1 Hz), 3.81–3.88 (12H, m).

REFERENCE EXAMPLE 32

3-(4-Hydroxy-3-nitrophenyl)-4-(4-hydroxyphenyl)-3-hexene

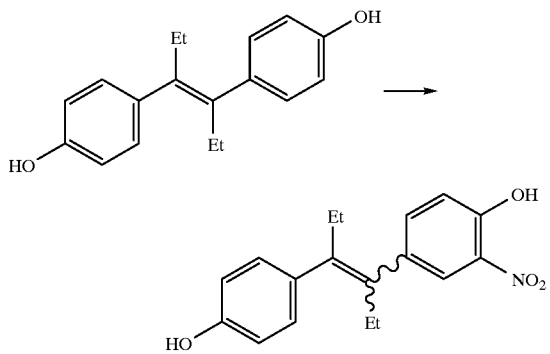

Under a nitrogen atmosphere, a suspension of diethylstilbestrol (1.0 g) in acetic acid (160 ml)-water (16 ml) was cooled to 5° C., and 70% nitric acid (0.34 g) was added dropwise thereto. Then, the resulting mixture was heated to 20° C. and stirred for 5 hours. The solvent was distilled off under reduced pressure and an aqueous sodium hydrogencarbonate solution was added to the residue, followed by two runs of extraction with ethyl acetate (150 ml). The combined organic layer was washed with water (200 ml), dried over anhydrous magnesium sulfate, and then concentrated under reduced pressure. The residue was purified by a silica gel column chromatography (n-hexane:ethyl acetate=9:1) to obtain 3-(4-hydroxy-3-nitrophenyl)-4-(4-hydroxyphenyl)-3-hexene (0.22 g, yield 19%).

$^1$H-NMR (CDCl$_3$) δ: ppm; 0.77 (3H×2/3, d, J=7.4 Hz; E-form), 0.78 (3H×2/3, d, J=7.6 Hz; E-form), 0.96 (3H×1/3, d, J=7.6 Hz; Z-form), 0.96 (3H×1/3, d, J=7.6 Hz; Z-form), 2.05–2.20 (4H×2/3, m; E-form), 2.46–2,59 (4H×1/3, m; Z-form), 4.74 (1H×1/3, br.s; Z-form), 4.90 (1H×2/3, br.s; E-form), 6.50–7.50 (7H, m), 7.73 (1H×1/3, d, J=2.0 Hz; Z-form), 7.95 (1H×2/3, d, J=1.7 Hz; E-form), 10.4 (1H×1/3, br.s; Z-form), 10.6 (1H×2/3, br.s; E-form).

REFERENCE EXAMPLE 33

3-(3-Amino-4-hydroxyphenyl)-4-(4-hydroxyphenyl)-3-hexene

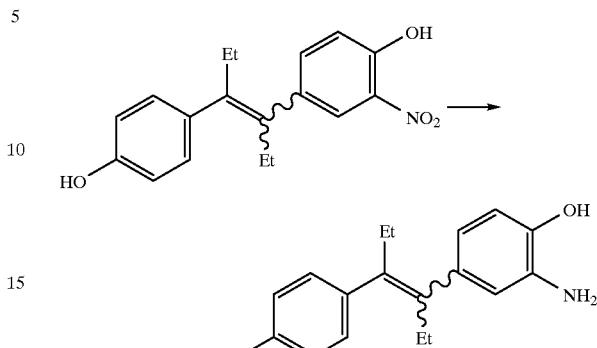

Under a nitrogen atmosphere, 3-(4-hydroxy-3-nitrophenyl)-4-(4-hydroxyphenyl)-3-hexene (1.87 g) obtained by the process described in Reference Example 32 was dissolved in an acetone (490 ml)-1N sodium hydroxide (46 ml) mixed solution, and sodium hydrosulfite (9.2 g) was added thereto under reflux and stirred for 30 minutes. Sodium hydrosulfite was added thereto with the lapse of time until the red color of the reaction mixture was discharged, while adding 1N sodium hydroxide so that the reaction mixture might be always kept alkaline. After a large portion of the acetone was distilled off under reduced pressure, the residue was neutralized with a 10% aqueous acetic acid solution. The precipitated crystals were collected by filtration, washed with chloroform, and then dried under reduced pressure (to obtain E-form). The filtrate was concentrated and the residue was separately purified by a silica gel column chromatography (chloroform:acetone=10:1) (to obtain a mixture of E-form and Z-form). The products were combined to obtain 3-(3-amino-4-hydroxyphenyl)-4-(4-hydroxyphenyl)-3-hexene (1.52 g, yield 90%).

$^1$H-NMR (CD$_3$OD) δ of E-form: ppm; 0.75 (3H, t, J=7.4 Hz), 0.75 (3H, t, J=7.4 Hz), 2.09 (2H, q, J=7.3 Hz), 2.14 (2H, q, J=7.4 Hz), 6.42 (1H, dd, J=2.1 Hz and 8.1 Hz), 6.61 (1H, d, J=1.7 Hz), 6.68 (1H, d, J=7.9 Hz), 6.76 (2H, d, J=8.9 Hz), 6.97 (2H, d, J=8.9 Hz).

REFERENCE EXAMPLE 34

3-(3-Amino-4-t-butyldimethylsilyloxyphenyl)-4-(4-t-butyldimethylsilyloxyphenyl)-3-hexene

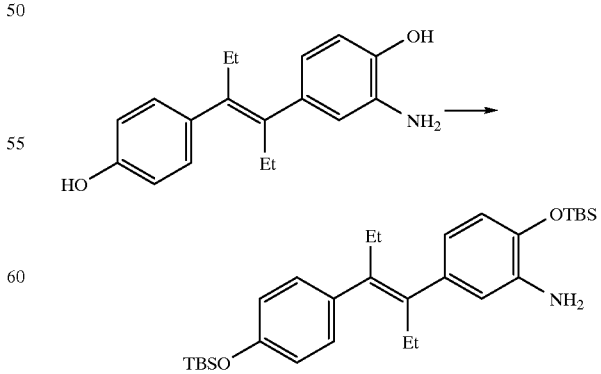

3-(3-Amino-4-t-butyldimethylsilyloxyphenyl)-4-(4-t-butyldimethylsilyloxyphenyl)-3-hexene (1.13 g, E-form, yield 41%) was obtained according to the process described in Reference Example 1, except for using 3-(3-amino-4-hydroxyphenyl)-4-(4-hydroxyphenyl)-3-hexene (1.52 g, E-form) obtained by the process described in Reference Example 33.

$^1$H-NMR (CDCl$_3$) δ: ppm; 0.22 (6H, s), 0.27 (6H, s), 0.75 (3H, t, J=7.4 Hz), 0.76 (3H, t, J=7.3 Hz), 1.00 (9H, s), 1.03 (9H, s), 2.02–2.21 (4H, m), 3.69 (2H, br.s), 6.45 (1H, dd, J=2.2 Hz and 8.1 Hz), 6.58 (1H, d, J=2.3 Hz), 6.71 (1H, d, J=7.9 Hz), 6.77–6.85 (2H, m), 6.98–7.06 (2H, m).

REFERENCE EXAMPLE 35

1,1-Bis(diisopropoxyphosphinoyl)-3-triphenylmethoxypropane

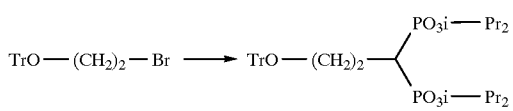

Under a nitrogen atmosphere, 60% sodium hydride (200 mg), 1-bromo-2-triphenylmethoxyethane (1.84 g) and tetraisopropyl methylenebisphosphonate (1.72 g) were suspended in toluene (5 ml), and the resulting suspension was stirred at 120° C. for 7 hours. The reaction mixture was diluted with toluene, and then a saturated aqueous ammonium chloride solution was added thereto to decompose the excess sodium hydride. Then, ethyl acetate was added thereto to effect separation, and the organic layer was dried over anhydrous magnesium sulfate and concentrated under reduced pressure. The residue was purified by a silica gel column chromatography (chloroform:acetone) to obtain 1,1-bis(diisopropoxyphosphinoyl)-3-triphenylmethoxypropane (2.44 g, yield 77%).

$^1$H-NMR (CDCl$_3$) δ: ppm; 1.27 (24H, d, J=6.3 Hz), 2.12–2.52 (3H, m), 3.25 (2H, t, J=6.9 Hz), 4.64–4.85 (4H, m), 7.2–7.6 (15H, m).

REFERENCE EXAMPLE 36

1,1-Bis(diisopropoxyphosphinoyl)-3-propanol

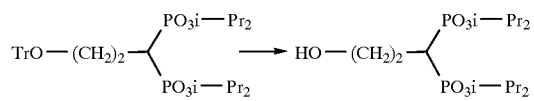

Under a nitrogen atmosphere, 1,1-bis(diisopropoxyphosphinoyl)-3-triphenylmethoxypropane (2.42 g) obtained by the process described in Reference Example 35 was dissolved in methanol (25 ml), followed by adding thereto concentrated hydrochloric acid (1 ml), and the resulting mixture was stirred at 60–70° C. for 2 hours. The reaction mixture was concentrated under reduced pressure, and then the residue was dissolved in chloroform and the resulting solution was dried over anhydrous magnesium sulfate and concentrated under reduced pressure. The residue was purified by a silica gel column chromatography (chloroform-acetone and then chloroform-methanol) to obtain 1,1-bis(diisopropoxyphosphinoyl)-3-propanol (1.12 g, yield 75%).

$^1$H-NMR (CDCl$_3$) δ: ppm; 1.35 (12H, d, J=6.3 Hz), 1.36 (6H, d, J=6.3 Hz), 1.36 (6H, d, J=5.9 Hz), 2.04–2.51 (3H, m), 3.60–3.87 (3H, m), 4.65–4.90 (4H, m).

REFERENCE EXAMPLE 37

3,3-Bis(diisopropoxyphosphinoyl)-1-iodopropane

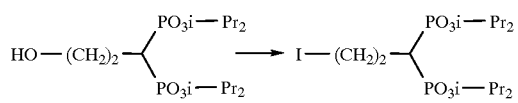

Under a nitrogen atmosphere, a solution in dry chloroform (15 ml) of 1,1-bis(diisopropoxyphosphinoyl)-3-propanol (1.16 g) obtained by the process described in Reference Example 36 and triethylamine (606 mg) was cooled with ice, and methanesulfonyl chloride (515 mg) was added dropwise thereto. After stirring for 1 hour, the reaction mixture was washed with water, dry over anhydrous magnesium sulfate, and then concentrated under reduced pressure to obtain a mesylate, which was dissolved in acetone (50 ml). Sodium iodide (4.50 g) was added thereto, and the resulting mixture was stirred under reflux for 3 hours, cooled to room temperature, diluted with ethyl acetate, and then washed with an aqueous sodim thiosulfate solution and an aqueous sodium chloride solution. The organic layer was dried over anhydrous magnesium sulfate and concentrated under reduced pressure to obtain 3,3-bis (diisopropoxyphosphinoyl)-1-iodopropane (1.26 g, yield 85%).

REFERENCE EXAMPLE 38

1,1-Bis(diixopropoxyphosphinoyl)-3-acetylthiopropane

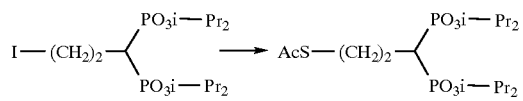

3,3-Bis(diisopropoxyphosphinoyl)-1-iodopropane (1.26 g) obtained by the process described in Reference Example 37 was dissolved in dry N,N-dimethylformamide (2.5 ml)-dry toluene (2.5 ml) under ice-cooling and a nitrogen atmosphere. Thereto was added dropwise a sodium thioacetate solution [previously prepared by adding dropwise thioacetic acid (0.46 g) to a suspension of 60% sodium hydride (160 mg) in dry N,N-dimethylformamide (2.5 ml)-dry toluene (2.5 ml)], and the resulting mixture was heated to room temperature and stirred for 2.5 hours. Toluene was added to the reaction mixture and the resulting mixture was washed 5 times with an aqueous sodium chloride solution, dried over anhydrous magnesium sulfate, and then concentrated under reduced pressure. The residue was purified by a silica gel column chromatography (ethyl acetate acetone= 100:0 to 50:50) to obtain 1,1-bis(diisopropoxyphosphinoyl)-3-acetylthiopropane (0.93 g, yield 81%).

$^1$H-NMR (CDCl$_3$) δ: ppm; 1.34 (12H, d, J=5.9 Hz), 1.35 (12H, d, J=6.3 Hz), 2.00–2.46 (3H, m), 2.32 (3H, s), 3.15 (2H, t, J=7.4 Hz), 4.65–4.90 (4H, m).

REFERENCE EXAMPLE 39

Sodium 3,3-bis(diisopropoxyphosphinoyl)propanesulfonate

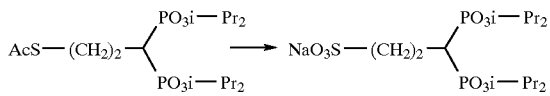

Under ice-cooling and a nitrogen atmosphere, 1,1-bis(diisopropoxyphosphinoyl)- 3-acetylthiopropane (0.81 g) obtained by the process described in Reference Example 38 was dissolved in acetone (14 ml), followed by adding thereto 5N sodium hydroxide (0.72 ml), a 31% aqueous hydrogen peroxide solution (3.6 ml) and sodium tungstate (a catalytic amount) in that order, and the resulting mixture was slowly heated to room temperature and stirred for 2.5 hours. The mixture was concentrated under reduced pressure and the residue was dissolved in water (50 ml), and then the resulting solution was washed three times with chloroform, and the aqueous layer was freeze-dried to obtain sodium 3,3-bis(diisopropoxyphosphinoyl)propanesulfonate (0.96 g).

REFERENCE EXAMPLE 40

3,3-Bis(diisopropoxyphosphinoyl)propanesulfonyl chloride

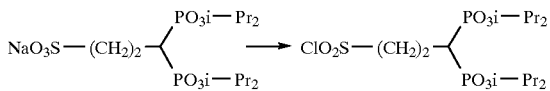

Sodium 3,3-bis(diisopropoxyphosphinoyl)propanesulfonate (100 mg) obtained by the process described in Reference Example 38 was suspended in dry monochlorobenzene (1 ml), and dry N,N-dimethylformamide (a catalytic amount) was added thereto, and then thionyl chloride (27 mg) was added dropwise thereto. The resulting mixture was stirred with heating at 75° C. for 0.5 hour, followed by adding thereto thionyl chloride (27 mg), and the resulting mixture was stirred with heating for another 2 hours. The reaction mixture was concentrated under reduced pressure to obtain 3,3-bis(diisopropoxyphosphinoyl)propanesulfonyl chloride (0.11 g).

EXAMPLE 38

Erythro 3-(3-(4,4-bis(diethoxyphosphinoyl)butyrylamino)-4-propionyloxyphenyl)-4-(4-propionyloxyphenyl)hexane

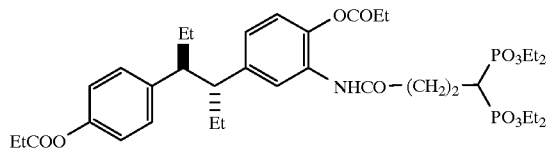

Under a nitrogen atmosphere, erythro 3-(3-(4,4-bis(diethoxyphosphinoyl)butyrylamino)-4-hydroxyphenyl)-4-(4-hydroxyphenyl)hexane (0.27 g) obtained by the process described in Example 7 and diisopropylethylamine (222 mg) were dissolved in dry methylene chloride (3.5 ml), and the resulting solution was cooled with ice. Then, a solution of propionyl chloride (119 mg) in dry methylene chloride (0.5 ml) was added dropwise thereto, and the resulting mixture was stirred under ice-cooling for 2.5 hours. The reaction mixture was diluted with chloroform, washed with a saturated aqueous sodium chloride solution, dried over anhydrous magnesium sulfate, and then concentrated under reduced pressure. The residue was purified by a silica gel thin-layer chromatography (chloroform:acetone=3:1) to obtain erythro 3-(3-(4,4-bis(diethoxyphosphinoyl)butyrylamino)-4-propionyloxyphenyl)-4-(4-propionyloxyphenyl)hexane (0.32 g, quantitative yield).

$^1$H-NMR (CDCl$_3$) δ: ppm; 0.53 (3H, t, J=7.3 Hz), 0.54 (3H, t, J=7.3 Hz), 1.17–1.47 (22H, m), 2.23–2.83 (11H, m), 4.10–4.30 (8H, m), 6.85–6.94 (1H, m), 6.99–7.10 (3H, m), 7.13–7.22 (2H, m), 8.19 (1H, br.s).

EXAMPLE 39

Erythro 3-(3-(4,4-diphosphonobutyrylamino)-4-propionyloxyphenyl)-4-(4-propionyloxyphenyl)hexane

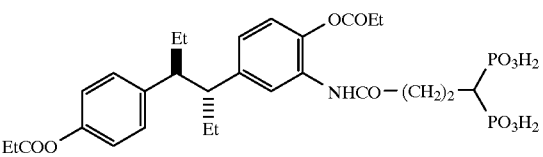

Under a nitrogen atmosphere, erythro 3-( 3-(4,4-bis(diethoxyphosphinoyl)butyrylamino)-4-propionyloxyphenyl)-4-(4-propionyloxyphenyl)hexane (0.37 g) obtained by the process described in Example 38 was dissolved in dry chloroform (3.7 ml), followed by adding dropwise thereto bromotrimethylsilane (0.66 ml). After stirring at room temperature for 43 hours, the reaction mixture was concentrated under reduced pressure. The residue was redissolved in chloroform and water was added to the resulting solution to carry out washing and separation. The chloroform layer was dried over anhydrous magnesium sulfate and concentrated under reduced pressure to obtain erythro 3-(3-(4,4-diphosphonobutyrylamino)-4-propionyloxyphenyl)-4-(4-propionyloxyphenyl)hexane (0.17 g, yield 54%).

IR (neat): cm$^{-1}$; 3350 (br.), 1762, 1650 (br.), 1600, 1540, 1502 730.

The effects of the present invention are explained in further detail with the following test examples, but the test examples are not intended in any way to limit the scope of the present invention.

Test compounds used in the test examples are as follows:

EXAMPLE 3

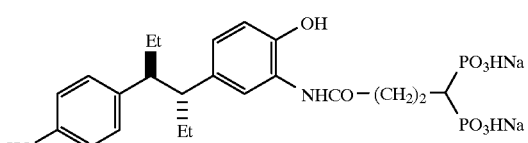

EXAMPLE 10

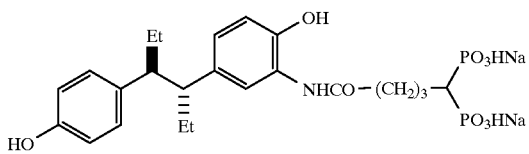

EXAMPLE 25

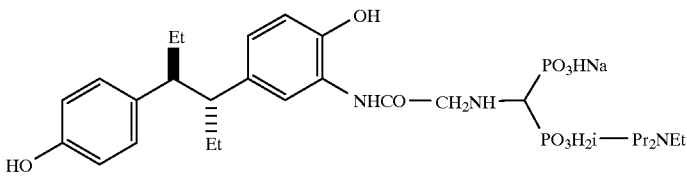

COMPARATIVE EXAMPLE 1

Hexestrol

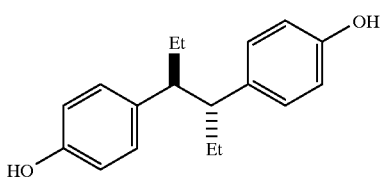

COMPARATIVE EXAMPLE 2

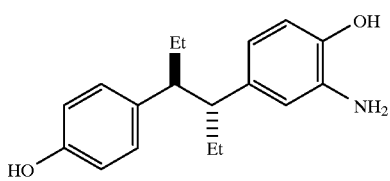

COMPARATIVE EXAMPLE 3

Etidronate

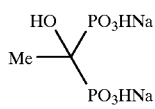

COMPARATIVE EXAMPLE 4

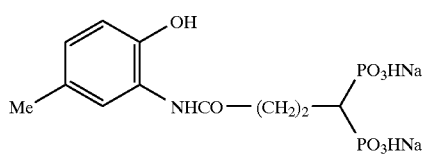

COMPARATIVE EXAMPLE 5

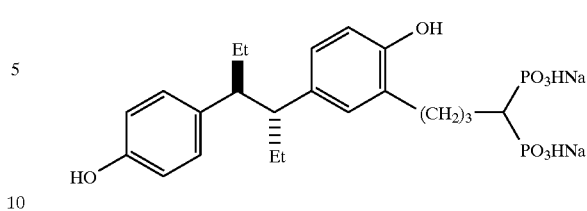

Comparative Example 2 is the synthetic estrogen described in J. Org. Chem., 38, 3525–3533 (1973), and Comparative Example 5 is the compound disclosed in Japanese Patent Unexamine Publication No. 5-222073.

TEST EXAMPLE 1

UMR-106 cells derived from rat osteosarcoma and COS-1 cells derived from monkey kidney were cultured in Dulbecco's minimal essential medium without Phenol Red (DMEM medium; available from COSMO BIO Co., Ltd.) containing 5% fetal bovine serum (availabale from GIBCO) stripped with dextran-coated charcoal. When 40–60% confluent state was brought about in each 90-mm Petri dish, 20 μg in total of DNA, i.e., 0.5 μg of an estrogen receptor expression vector, 1 μg of a chloramphenicol acetyltransferase (CAT) reporter plasmid containing a Xenopus vitellogenin estrogen responsive element and a rabbit β-globin promoter, 3 μg of β-galactosidase expression vector (pCH110, available from Pharmacia) and 15.5 μg of M13+ plasmid (available from Stratagene) were transfected into cells by means of calcium phosphate coprecipitation. After 1 hour, each test compound was dissolved in sterillized and distilled water or dimethyl sulfoxide (DMSO) (in the case of Comparative Example 1 and Comparative Example 2) and added to the medium to adjust the final concentration of the test compound in the medium to 1 μM or 10 nM (in the case of Comparative Example 1). If necessary, DMSO was added to the medium to adjust the final concentration of DMSO in the medium to 0.1% (10 μl/10 ml). After 24 hours of culture, the medium was replaced by fresh medium and the test compound was again added thereto in the same manner as above. After another 24 hours of culture, cells were scraped off and their β-galactosidase activity was measured by a conventional method to confirm the efficiency of DNA transfection into cells. Then, the activity of CAT enzyme due to the activation of the estrogen receptor was investigated. In detail, according to the method of Kato et al. [Cell, 68, 731–743 (1992)], acetyl CoA (available from Sigma Chemical Co.) and $^{14}$C-chloramphenicol (available from Amersham) were reacted using 1 unit (UMR-106 cells) or 40 units (COS-1 cells) of cell extract, followed by a silica gel thin-layer chromatography, and the radio-activity of each of spots corresponding to acetyl $^{14}$C-chloramphenicol and $^{14}$C-chloramphenicol, respectively, which had been separated on the thin layer was determined with an image analyzer (BAS-2000, mfd. by Fuji Photo Film Co., Ltd.), after which the production rate (%) of acetyl $^{14}$C-chloramphenicol was calculated. The result of an experiment carried out in the same manner as above except for using medium containing only 0.1% DMSO was used as a control value, and the test compounds were compared in estrogen activity on the basis of the ratio of the calculated value obtained from each of them to the control value.

The results are shown in Table 1.

TABLE 1

Comparison in estrogen activity[1])

| Test compound | UMR-106 cells | COS-1 cells |
|---|---|---|
| Control (Compound of the invention) | 1.0 | 1.0 |
| Example 3 | 4.5 | 10 |
| Example 10 | 1.2 | 7.2 |
| Example 25 (Reference compound) | 5.6 | 10 |
| Comparative Example 1 | 20 | 6.9 |
| Comparative Example 2 | 14 | 7.7 |
| Comparative Example 3 | 1.1 | 1.0 |
| Comparative Example 4 | 0.8 | 1.3 |
| Comparative Example 5 | 1.1 | 0.9 |

[1])Expressed as the ratio of the average of duplicates to the control value.
[2])The test was carried out at a concentration of 10 nM only in the case of Comparative Example 1 or 1 μM in the case of other test compounds.

TEST EXAMPLE 2

The ovaries including oviductus of each Wistar strain female rat aged 7 weeks were removed from the back side under ether anesthesia. After 1 week, each test compound was began to be administered to a group of five of the thus treated rats. The test compound was subcutaneously administered in a dose of 0.01 to 3 mg/kg per day in one portion five times a week for 3 consecutive weeks in the form of a solution prepared as follows: each of the compounds of Comparative Example 1 and Comparative Example 2 were dissolved in a 5% ethanol-95% middle chain triacylglycerol (MCT) mixed solution, and each of other test compounds were dissolved in phosphate-buffered saline (pH 7.4). The rats were sacrified 24 hours after the final administration day, and the bone mineral density in proximal tibia and the wet weight of the uterus were measured. A group subjected to ovariectomy but not to administration of a test compound (a control group) and a group subjected to neither ovariectomy nor administration of a test compound (a sham-operation group) were also subjected to autopsy, and the bone mineral density and the wet weight of the uterus were measured. The above measurement of the bone mineral density was carried out by means of a bone mineral density measuring apparatus (DCS-600, mfd. by Aloka) applying dual energy X-ray absorptiometry (DXA method). The average of measured values for 5 rats in each group was calculated, and the restoration rate of each of the bone mineral density and the uterus weight was calculated by the following equation:

Restoration rate(%) =
(average for compound-treated group - average for control group) / (average for sham-operation group - average for control group) × 100

The results are shown in Table 2.

TABLE 2

Restoration rates (%) in rats subjected to ovaricetomy

| Test compound | Bone mineral density | Uterus weight |
|---|---|---|
| Control (Compound of the invention) | 0 | 0 |
| Example 3 | 165 | 48 |
| Example 10 | 114 | 39 |
| Example 25 (Reference compound) | 240 | 89 |
| Comparative Example 1 | 83 | 132 |
| Comparative Example 2 | 158 | 101 |
| Comparative Example 3 | 55 | 0 |
| Comparative Example 4 | 95 | 0 |
| Comparative Example 5 | 170 | 15 |

The doses of the test compounds; Comparative Example 1: 0.01 mg/Kg, Comparative Example 3: 2 mg/Kg, Comparative Example 5: 3 mg/Kg, other test compounds: 1 mg/Kg.

From the results of Test Example 1 and Test Example 2, the following was found: the compounds of Comparative Example 1 and Comparative Example 2 are clearly estrogen compounds and strongly inhibit the decrease caused by the ovariectomy of not only the bone mineral density but also the uterus weight, while the compounds of the present invention exhibit a much larger effect on the restoration rate of the bone mineral density than on the restoration rate of the uterus weight, namely, they have pharmacological effect selectively on bone, though they retain estrogen activity.

On the other hand, none of Comparative Example 3 (etidronate) which is an inhibitor of bone resorption, Comparative Example 4 obtained by combining a non-estrogen compound and a bisphosphonic acid derivative, and Comparative Example 5 obtained by combining bisphosphonic acid and an estrogen compound through an alkylene chain have estrogen activity, and hence they are clearly distinguished from the compounds of the present invention.

INDUSTRIAL APPLICABILITY

The estrogen derivatives (I) having carriers to bone of the present invention exhibit a more selective and lasting pharmacological effect on bone tissue than on other organs such as geniral organs, etc., and increase bone mineral density as estrogen. Therefore, they are useful as a therapeutic or prophylactic agent for osteroporosis, in particular, postmenopausal osteroporosis which has less adverse side effect.

Furthermore, the compounds of the present inventions are useful as a prophylactic or therapeutic agent for medical symptoms caused by estrogen deficiency, such as menopausal disorders, lipid metabolism abnormality and vasomotor syndrome associated with menopause, atrophic vaginitis, kraurosis vulvae, premenstrual tension syndrome, female hypogonadism, or coronary cardiopathy in post-menopausal women or as a contraceptive.

We claim:

1. A compound represented by the general formula (I):

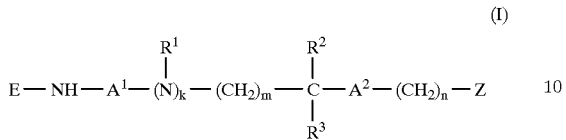

(I)

wherein $A^1$ is —CO— or —SO$_2$—; $A^2$ is a single bond, —S—, —O—, a group of the formula —NR$^4$— wherein $R^4$ is a hydrogen atom or an alkyl group of 1 to 6 carbon atoms, or a group of the formula —CO—NR$^4$— wherein $R^4$ is as defined above; $R^1$ is a hydrogen atom or an alkyl group of 1 to 6 carbon atoms; $R^2$ and $R^3$, which may be the same or different, are independently a hydrogen atom, an alkyl group of 1 to 6 carbon atoms, an alkenyl group of 3 to 6 carbon atoms, a cycloalkyl group of 3 to 7 carbon atoms, an aralkyl group, a substituted aralkyl group, a phenyl group or a substituted phenyl group, or $R^2$ and $R^3$, when taken together with the carbon atom to which they are bonded, form a saturated or unsaturated 3- to 7-membered alicyclic hydrocarbon group; k is 0 or 1 in the case of $A^1$ being —CO—, and k is 0 in the case of $A^1$ being —SO$_2$—; m and n are independently an integer of 0 to 5;

Z is a group represented by any of the following general formulas (IIa) to (IIc):

(IIa)

wherein $R^5$ is a hydrogen atom, a halogen atom, a methyl group, a hydroxyl group or a protected hydroxyl group, and $R^6$, $R^7$, $R^8$ and $R^9$ are independently a hydrogen atom, an alkyl group of 1 to 6 carbon atoms, a haloalkyl group of 2 to 6 carbon atoms, an allyl group, a benzyl group or a group of the formula —CH$_2$—O—CO—R$^{10}$ wherein $R^{10}$ is an alkyl group of 1 to 6 carbon atoms,

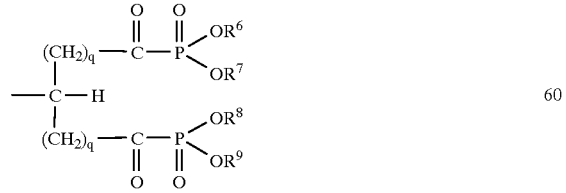

(IIb)

wherein $R^6$, $R^7$, $R^8$ and $R^9$ are as defined above, and q is 0 or 1, and

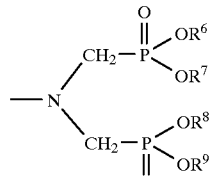

(IIc)

wherein $R^6$, $R^7$, $R^8$ and $R^9$ are as defined above; and E is a group of the general formula (III):

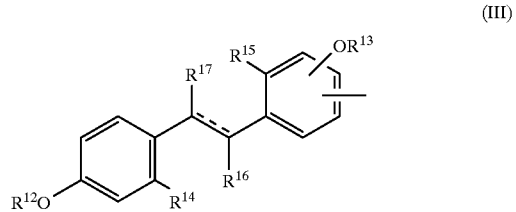

(III)

wherein $R^{12}$ and $R^{13}$, which may be the same or different, are independently a hydrogen atom, a hydroxyl-protecting group, a group of the formula —CO—NR$^{18}$R$^{19}$ wherein $R^{18}$ and $R^{19}$, which may be the same or different, are independently a hydrogen atom, an alkyl group of 1 to 10 carbon atoms, a hydroxyalkyl group of 2 to 6 carbon atoms, a haloalkyl group of 2 to 6 carbon atoms, a phenyl-substituted or unsubstituted carboxyalkyl group of 2 to 6 carbon atoms, a cycloalkyl group of 3 to 7 carbon atoms, an aralkyl group, a substituted aralkyl group, a phenyl group or a substituted phenyl group; a group of the formula —CO—R$^{20}$ wherein $R^{20}$ is an alkyl group of 1 to 19 carbon atoms, an alkenyl group of 3 to 19 carbon atoms, a cycloalkyl group of 3 to 7 carbon atoms, an alkyl group of 1 to 6 carbon atoms substituted by a cycloalkyl group of 3 to 7 carbon atoms, an aralkyl group, a substituted aralkyl group, a phenyl group, a substituted phenyl group, or a 5- or 6-membered hetero-cyclic group; or a group of the general formula (IV):

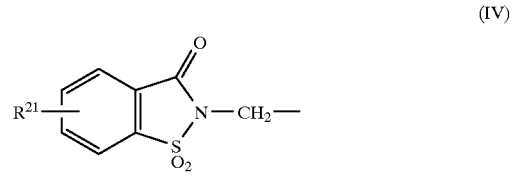

(IV)

wherein $R^{21}$ is a hydrogen atom, a halogen atom, an alkyl group of 1 to 6 carbon atoms, or an alkoxy group of 1 to 6 carbon atoms; $R^{14}$ and $R^{15}$, which may be the same or different, are independently a hydrogen atom, a halogen atom, a methyl group, a hydroxyl group or a protected hydroxyl group; $R^{16}$ is an alkyl group of 1 to 6 carbon atoms, a hydroxyalkyl group of 2 to 6 carbon atoms, a haloalkyl group of 2 to 6 carbon atoms, a phenyl group, or a phenyl group substituted by a hydroxyl group or a protected hydroxyl group; $R^{17}$ is an alkyl group of 1 to 6 carbon atoms, a hydroxyalkyl group of 2 to 6 carbon atoms, or a haloalkyl group of 2 to 6 carbon atoms; $R^{14}$ and $R^{16}$, when taken together, may form —O—, —CH$_2$— or —CH$_2$CH$_2$—, and $R^{15}$ and $R^{17}$, when taken together as —$R^{17}$—$R^{15}$—, may form —O—, —S—, —COO—, —OCO—, a group of the formula —NR$^{22}$— wherein $R^{22}$ is an alkyl group of 1 to 6 carbon atoms, a hydroxyalkyl group of 2 to 6 carbon atoms, or a haloalkyl group of 2 to 6 carbon atoms; a group of the formula —CHR$^{22}$—A$^3$— or a group of the formula —A$^3$—CHR$^{22}$— wherein $R^{22}$ is as defined above, and A$^3$ is a single bond, —O— or —CH$_2$—; and the combination of the broken line and solid line between the carbon atoms to which $R^{16}$ and $R^{17}$, respectively, are bonded represents a single bond or a double bond, or a pharmaceutically acceptable salt thereof.

2. A compound or a pharmaceutically acceptable salt thereof according to claim 1, wherein Z is a group represented by the general formula (IIa).

3. A compound or a pharmaceutically acceptable salt thereof according to claim 2, wherein A$^1$ is —CO— and A$^2$ is a single bond or a group represented by the formula —NR$^4$— wherein R$^4$ is a hydrogen atom or an alkyl group of 1 to 6 carbon atoms.

4. A compound or a pharmaceutically acceptable salt thereof according to claim 3, wherein E is a group represented by the general formula (IIIa):

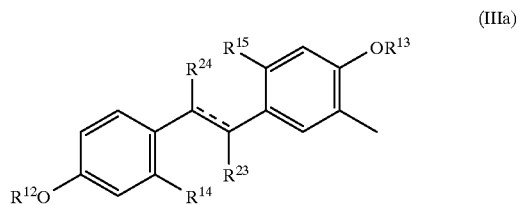

(IIIa)

wherein $R^{12}$ and $R^{13}$, which may be the same or different, are independently a hydrogen atom, a hydroxyl-protecting group, a group of the formula —CO—NR$^{18}$R$^{19}$ wherein $R^{18}$ and $R^{19}$, which may be the same or different, are independently a hydrogen atom, an alkyl group of 1 to 10 carbon atoms, a hydroxyalkyl group of 2 to 6 carbon atoms, a haloalkyl group of 2 to 6 carbon atoms, a phenyl-substituted or unsubstituted carboxyalkyl group of 2 to 6 carbon atoms, a cycloalkyl group of 3 to 7 carbon atoms, an aralkyl group, a substituted aralkyl group, a phenyl group or a substituted phenyl group; a group of the formula —CO—R$^{20}$ wherein R$^{20}$ is an alkyl group of 1 to 19 carbon atoms, an alkenyl group of 3 to 19 carbon atoms, a cycloalkyl group of 3 to 7 carbon atoms, an alkyl group of 1 to 6 carbon atoms substituted by a cycloalkyl group of 3 to 7 carbon atoms, an aralkyl group, a substituted aralkyl group, a phenyl group, a substituted phenyl group, or a 5- or 6-membered heterocyclic group; or a group of the general formula (IV):

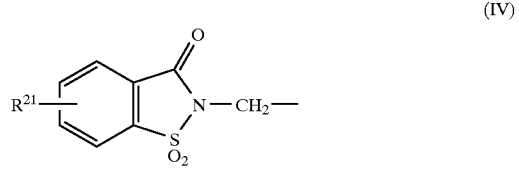

(IV)

wherein $R^{21}$ is a hydrogen atom, a halogen atom, an alkyl group of 1 to 6 carbon atoms, or an alkoxy group of 1 to 6 carbon atoms, $R^{14}$ and $R^{15}$, which may be the same or different, are independently a hydrogen atom, a halogen atom, a methyl group, a hydroxyl group or a protected hydroxyl group, $R^{23}$ and $R^{24}$, which may be the same or different, are independently an alkyl group of 1 to 6 carbon atoms, a hydroxyalkyl group of 2 to 6 carbon atoms or a haloalkyl group of 2 to 6 carbon atoms, and the combination of the broken line and solid line between the carbon atoms to which $R^{23}$ and $R^{24}$, respectively, are bonded represents a single bond or a double bond.

5. A compound or a pharmaceutically acceptable salt thereof according to claim 4, wherein E is a group represented by the general formula (IIIb):

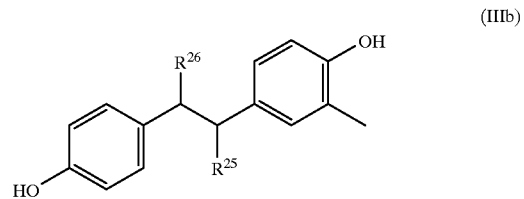

(IIIb)

wherein $R^{25}$ and $R^{26}$, which may be the same or different, are independently an alkyl group of 1 to 6 carbon atoms.

6. A compound or a pharmaceutically acceptable salt thereof according to claim 3, wherein E is a group represented by the general formula (IIIc):

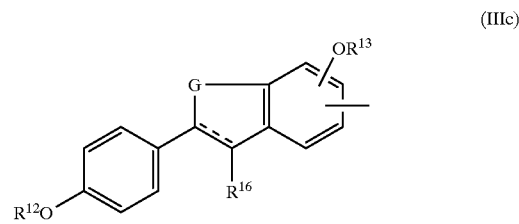

(IIIc)

wherein $R^{12}$ and $R^{13}$, which may be the same or different, are independently a hydrogen atom, a hydroxyl-protecting group, a group of the formula —CO—NR$^{18}$R$^{19}$ wherein $R^{18}$ and $R^{19}$, which may be the same or different, are independently a hydrogen atom, an alkyl group of 1 to 10 carbon atoms, a hydroxyalkyl group of 2 to 6 carbon atoms, a haloalkyl group of 2 to 6 carbon atoms, a phenyl-substituted or unsubstituted carboxyalkyl group of 2 to 6 carbon atoms, a cycloalkyl group of 3 to 7 carbon atoms, an aralkyl group, a substituted aralkyl group, a phenyl group or a substituted phenyl group; a group of the formula —CO—R$^{20}$ wherein R$^{20}$ is an alkyl group of 1 to 19 carbon atoms, an alkenyl group of 3 to 19 carbon atoms, a cycloalkyl group of 3 to 7 carbon atoms, an alkyl group of 1 to 6 carbon atoms substituted by a cycloalkyl group of 3 to 7 carbon atoms, an aralkyl group, a substituted aralkyl group, a phenyl group, a substituted phenyl group, or a 5- or 6-membered heterocyclic group; or a group of the general formula (IV):

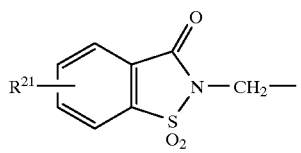
(IV)

wherein $R^{21}$ is a hydrogen atom, a halogen atom, an alkyl group of 1 to 6 carbon atoms, or an alkoxy group of 1 to 6 carbon atoms, and $R^{16}$ is an alkyl group of 1 to 6 carbon atoms, a hydroxyalkyl group of 2 to 6 carbon atoms, a haloalkyl group of 2 to 6 carbon atoms, a phenyl group or a phenyl group substituted by a hydroxyl group or a protected hydroxyl group, G is —O—, —S—, —COO—, —OCO—, a group of the formula —NR$^{22}$— wherein $R^{22}$ is an alkyl group of 1 to 6 carbon atoms, a hydroxyalkyl group of 2 to 6 carbon atoms, or a haloalkyl group of 2 to 6 carbon atoms, a group of the formula —CHR$^{22}$—A$^3$— or a group of —A$^3$—CHR$^{22}$— wherein $R^{22}$ is as defined above and $A^3$ is a single bond, —O— or —CH$_2$—, and the combination of the broken line and solid line between the carbon atom to which $R^{16}$ is bonded and the carbon atom adjacent thereto represents a single bond or a double bond.

7. A compound or a pharmaceutically acceptable salt thereof according to claim 6, wherein E is a group represented by the general formula (IIId):

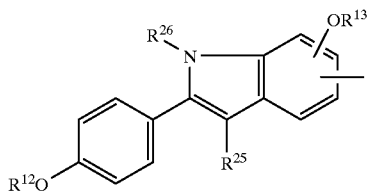
(IIId)

wherein $R^{12}$ and $R^{13}$, which may be the same or different, are independently a hydrogen atom, a hydroxyl-protecting group, a group of the formula —CO—NR$^{18}$R$^{19}$ wherein $R^{18}$ and $R^{19}$, which may be the same or different, are independently a hydrogen atom, an alkyl group of 1 to 10 carbon atoms, a hydroxyalkyl group of 2 to 6 carbon atoms, a haloalkyl group of 2 to 6 carbon atoms, a phenyl-substituted or unsubstituted carboxyalkyl group of 2 to 6 carbon atoms, a cycloalkyl group of 3 to 7 carbon atoms, an aralkyl group, substituted aralkyl group, a phenyl group or a substituted phenyl group; a group, of the formula —CO—R$^{20}$ wherein $R^{20}$ is an alkyl group of 1 to 19 carbon atoms, an alkenyl group of 3 to 19 carbon atoms, a cycloalkyl group of 3 to 7 carbon atoms, an alkyl group of 1 to 6 carbon atoms substituted by a cycloalkyl group of 3 to 7 carbon atoms, an aralkyl group, a substituted aralkyl group, a phenyl group, a substituted phenyl group, or a 5- or 6-membered heterocyclic group; or a group of the general formula (IV):

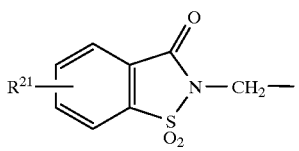
(IV)

wherein $R^{21}$ is a hydrogen atom, a halogen atom, an alkyl group of 1 to 6 carbon atoms, or an alkoxy group of 1 to 6 carbon atoms, and $R^{25}$ and $R^{26}$, which may be the same or different, are independently an alkyl group of 1 to 6 carbon atoms.

8. Erythro 3-(3-(4,4-diphosphonobutyrylamino)-4-hydroxyphenyl)-4-(4-hydroxyphenyl)hexane which is represented by the formula:

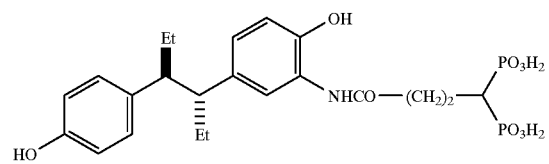

or a pharmaceutically acceptable salt thereof.

9. Erythro 3-(3-(5,5-diphosphonovalerylamino)-4-hydroxyphenyl)-4-(4-hydroxyphenyl)hexane, which is represented by the formula:

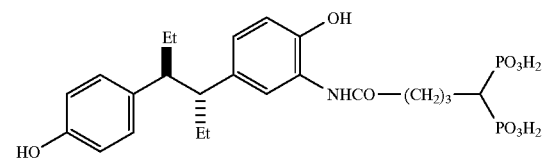

or a pharmaceutically acceptable salt thereof.

10. Erythro 3-(3-((diphosphonomethylamino)acetylamino)-4-hydroxyphenyl)-4-(4-hydroxyphenyl)hexane, which is represented by the formula:

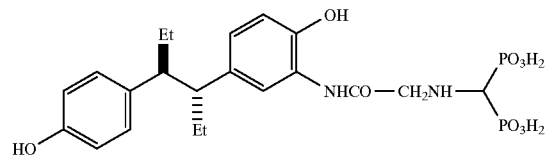

or a pharmaceutically acceptable salt thereof.

11. A pharmaceutical composition comprising a compound or a pharmaceutically acceptable salt thereof according to any one of claims 1 to 10.

12. A pharmaceutical composition for the treatment or prophylaxis of osteoporosis, menopausal disorders, lipid metabolism abnormality and vasomotor syndrome associated with menopause, atrophic vaginitis, kraurosis vulvae, premenstrual tension syndrome, female hypogonadism, or coronary cardiopathy in postmenopausal women or for contraception, which comprises a compound or a pharmaceutically acceptable salt thereof according to any one of claims 1 to 10 as an active ingredient.

13. A method for treating osteoporosis, menopausal disorders, lipid metabolism abnormality and vasomotor syndrome associated with menopause, atrophic vaginitis, kraurosis vulvae, premenstrual tension syndrome, female hypogonadism, or coronary cardiopathy in postmenopausal women or for contraception, which comprises administering an effective amount of a compound or a pharmaceutically acceptable salt thereof according to any one of claims 1 to 10 to a human being.

* * * * *